US008071738B2

(12) United States Patent
Collisson et al.

(10) Patent No.: US 8,071,738 B2
(45) Date of Patent: *Dec. 6, 2011

(54) FELINE CD86 POLYPEPTIDES AND NUCLEIC ACIDS

(75) Inventors: Ellen W. Collisson, Upland, CA (US); In-Soo Choi, Seoul (KR); Barbara J. Winslow, San Rafael, CA (US); Mark D. Cochran, Carlsbad, CA (US)

(73) Assignees: Texas A&M University System, College Station, TX (US); Intervet Inc., Summit, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/794,422

(22) Filed: Jun. 4, 2010

(65) Prior Publication Data

US 2011/0008377 A1   Jan. 13, 2011

Related U.S. Application Data

(62) Division of application No. 11/414,707, filed on Apr. 27, 2006, now Pat. No. 7,745,593, which is a division of application No. 09/303,510, filed on Apr. 30, 1999, now Pat. No. 7,078,512.

(60) Provisional application No. 60/083,869, filed on May 1, 1998.

(51) Int. Cl.
*C07H 21/04* (2006.01)
*C12N 15/00* (2006.01)
*C07K 1/00* (2006.01)

(52) U.S. Cl. ............... 536/23.1; 435/320.1; 530/350

(58) Field of Classification Search ................ None
See application file for complete search history.

(56) References Cited

U.S. PATENT DOCUMENTS

| | | | |
|---|---|---|---|
| 5,525,714 A | 6/1996 | Van Broeckhoven et al. | |
| 5,942,607 A | 8/1999 | Freeman et al. | |

FOREIGN PATENT DOCUMENTS

| | | |
|---|---|---|
| JP | 09-291100 | 11/1997 |
| WO | WO 95/03408 | 2/1995 |
| WO | WO 95/06738 | 3/1995 |
| WO | WO 99/47558 | 9/1999 |
| WO | WO 99/57295 | 11/1999 |

OTHER PUBLICATIONS

Akeson, A.L., "A fluorometric assay for the quantitation of cell adherence to endothelial cells," *Journal of Immunological Methods*, vol. 163, pp. 181-185 (1993).
Allison, J.P. et al., "Structure, Function, and Serology of the T-cell Antigen Receptor Complex," *Annu. Rev. Immunol*, vol. 5, pp. 503-540 (1987).
Allison, J.P., "CD28-B7 interaction in T-cell activation," *Current Opinion in Immunology*, vol. 6, pp. 414-419 (1994).
Anderson, P. et al., "Regulatory interactions between members of the immunoglobulin superfamily," *Immunology Today*, vol. 9, Nos. 7 and 8, pp. 199-203 (1988).
Antonia, S.J. et al., "B7-1 Expression by a Non-Antigen Presenting Cell-derived Tumor," *Cancer Research*, vol. 55, pp. 2253-2256 (1995).
Argyle, D.J. et al., "Nucleotide and predicted peptide sequence of feline interferon-gamma (IFN-γ)," *DNA Sequence—The Journal of Sequencing and Mapping*, vol. 5, pp. 169-171 (1995).
Arima, T. et al., "Inhibition by CTLA4Ig of Experimental Allergic Encephalomyelitis," *The Journal of Immunology*, vol. 156, pp. 4916-4924 (1996).
Arruffo, A., et al., "Molecular cloning of a CD28 cDNA by a high-efficiency COS cell expression system," *Proc. Natl. Acad. Sci. USA*, vol. 84, pp. 8573-8577 (1987).
Asjo, B. et al., "A Novel Mode of Human Immunodeficiency Virus Type 1 (HIV-1) Activation: Ligation of CD28 Alone Induces HIV-1 Replication in Naturally Infected Lymphocytes," *Journal of Virology*, vol. 67, No. 7, pp. 4395-4398 (1993).
Azuma, M. et al., "Functional Expression of B7/BB1 on Activated T Lymphocytes," *J. Exp. Med.*, vol. 177, pp. 845-850 (1993).
Azuma, M. et al., "Involvement of CD28 in MHC-Unrestricted Cytotoxicity Mediated by a Human Natural Killer Leukemia Cell Line," *The Journal of Immunology*, vol. 149, No. 4, pp. 1115-1123 (1992).
Azuma, M. et al., "Requirements for CD28-Dependent T Cell-Mediated Cytotoxicity," *The Journal of Immunology*, vol. 150, No. 6, pp. 2091-2101 (1993).
Azuma, M. et al., "B70 antigen is a second ligand for CTLA-4 and CD28," *Nature*, vol. 366, pp. 76-79 (1993).
Bajorath, J. et al., "Immunoglobulin fold characteristics of B7-1 (CD80) and B7-2 (CD86)," *Protein Science*, vol. 3, pp. 2148-2150(1994).
Bajorath, J. et al., "Knowledge-based model building of proteins: Concepts and examples," Protein Science, vol. 2, pp. 1798-1810(1993).
Balzano, C. et al., "CTLA-4 and CD28: Similar Proteins, Neighbouring Genes," *Int. J. Cancer: Supplement*, vol. 7, pp. 28-32 (1992).
Barcy, S. et al., "FcR cross-linking on monocytes results in impaired T cell stimulatory capacity," *International Immunology*, vol. 7, No. 2, pp. 179-189 (1995).

(Continued)

*Primary Examiner* — Bo Peng
(74) *Attorney, Agent, or Firm* — Loeb & Loeb LLP

(57) ABSTRACT

The present invention provides isolated and purified DNA encoding feline CD80 (B7-1) ligand, feline CD86 (B7-2) ligand, feline CD28 receptor, or feline CTLA-4 (CD152) receptor, as well as vectors comprising nucleic acid encoding feline CD80, feline CD86, feline CD28, or feline CTLA-4. The present invention provides a host cells transformed with CD80-encoding vectors, CD86-encoding vectors, CD28-encoding vectors, or CTLA-4-encoding vectors. The invention provides polypeptides encoded by the nucleic acid of feline CD80, feline CD86, feline CD28, or feline CTLA-4. The present invention provides a vaccine comprising an effective amount of polypeptides encoded by the nucleic acid of feline CD80, feline CD86, feline CD28, or feline CTLA-4. The present invention also provides vaccines which further comprise immunogens derived from pathogens. The invention provides for vaccines capable of enhancing an immune response. The invention also provides for vaccines capable of suppressing and immune response.

9 Claims, 13 Drawing Sheets

OTHER PUBLICATIONS

Beale, D., "A Comparison of the Amino Acid Sequences of the Extracellular Domains of the Immunoglobulin Superfamily. Possible Correlations Between Conservancy and Conformation," *Comp. Biochem. Physiol*, vol. 80B, No. 2, pp. 181-194 (1985).

Bellone, M. et al., "In vitro priming of cytotoxic T lymphocytes against poorly immunogenic epitopes by engineered antigen presenting cells," *Eur. J. Immunol*, vol. 24, pp. 2691-2698 (1994).

Berke, G., "The Binding and Lysis of Target Cells by Cytotoxic Lymphocytes: Molecular and Cellular Aspects," *Annu. Rev. Immunol*, vol. 12, pp. 735-773 (1994).

Berke, G., "The Functions and Mechanisms of Action of Cytolytic Lymphocytes," *Fundamental Immunology*. (W. Paul), New York: Raven Publ. 3d ed., pp. 965-1014 (1993).

Boise, L.H. et al., "CD28 Costimulation Can Promote T Cell Survival by Enhancing the Expression of Bcl-xL," *Immunity*, vol. 3, pp. 87-98 (1995).

Brinchmann, J.E. et al., "Expression of Costimulatory Molecule CD28 on T Cells in Human Immunodeficiency Virus Type 1 Infection: Functional and Clinical Correlations," *The Journal of Infectious Diseases*, vol. 169, pp. 730-738 (1994).

Brown, W.C. et al., "Feline Immunodeficiency Virus Infects Both $CD4_+$ and $CD8^+$ T Lymphocytes," *Journal of Virology*, vol. 65, No. 6, pp. 3359-3364 (1991).

Buck, C.A., "Immunoglobulin superfamily: structure, function and relationship to other receptor molecules," *Seminars in Cell Biology*, vol. 3, pp. 179-188 (1992).

Buelens, C. et al., "Interleukin 10 differentially regulates B7-1 (CD80) and B7-2 (CD86) expression on human peripheral blood dendritic cells," *Eur. J. Immunol.*, vol. 25, pp. 2668-2672 (1995).

Caruso, A. et al., "Expression of CD28 on CD8+ and CD4+. Lymphocytes During HIV Infection," *Scand. J. Immunol*, vol. 40, pp. 485-490 (1994).

Cerdan, C. et al., IL-1a is Produced by T Lymphocytes Activated Via the CD2 Plus CD28 Pathways, *The Journal of Immunology*, vol. 146, No. 2, pp. 560-564 (1991).

Chambers, C.A., et al., "Co-stimulation in T cell responses," *Current Opinion in Immunology*, vol. 9, pp. 396-404 (1997).

Chen, L. et al., "Costimulation of Antitumor Immunity by the B7 Counterreceptor for the T Lymphocyte Molecules CD28 and CTLA-4," *Cell*, vol. 71, pp. 1093-1102 (1992).

Chen, L. et al., "Costimulation of T cells for tumor immunity," *Immunology Today*, vol. 14, No. 10, pp. 483-486 (1993).

Chen, L. et al., "Induction of Cytotoxic T Lymphocytes Specific for a Syngeneic Tumor Expressing the E6 Oncoprotein of Human Papillomavirus Type 16," *The Journal of Immunology*, vol. 148, No. 8, pp. 2617-2621 (1992).

Chesnut, R.W. et al., "Antigen Presentation by B Cells and its Significance in T-B Interactions," *Advances in Immunology*, vol. 39, pp. 51-94 (1986).

Choi, I-S et al., "Mechanisms of Interaction between FIV infected and FIV effector T. Lymphocytes," Dissertation, Texas A&M University, pp. 1-119 Dec. 1998.

Choi, I-S et al. "Sequence analyses of feline B7 costimulatory molecules" *Veterinary Immunology and Immunopathology*, vol. 73, No. 3-4, pp. 219-231, Mar. 15, 2000.

Clark, S.J. et al., "High Titers of Cytopathic Virus in Plasma of Patients With Symptomatic of Primary HIV-1 Infection," *The New England Journal of Medicine*, vol. 324, No. 14, pp. 954-960 (1991).

Clayberger, C. et al., "Peptides Corresponding to the CD8 and CD4 Binding Domains of HLA Molecules Block T Lymphocyte Immune Responses In Vitro," *The Journal of Immunology*, vol. 153, pp. 946-951 (1994).

Clevers, H. et al., "The T Cell Receptor/CD3 Complex: A Dynamic Protein Ensemble," *Annu. Rev. Immunol*, vol. 6, pp. 629-662 (1988).

Connor, R.I. et al., "Increased Viral Burden and Cytopathicity Correlate Temporarily With CD4+ T-Lymphocyte Decline and Clinical Progression in Human Immunodeficiency Virus Type 1-Infected Individuals," *Journal of Virology*, vol. 67, No. 4, pp. 1772-1777 (1993).

Cooper, D.A. et al., "Characterization of T Lymphocyte Responses During Primary Infection With Human Immunodeficiency Virus," *Journal of Infectious Diseases*, vol. 157, No. 5, pp. 889-896 (1988).

Damle, N.K. et al., "Costimulation of T Lymphocytes with Integrin Ligands Intercellular Adhesion Molecule-1 or Vascular Cell Adhesion Molecule-1 Induces Functional Expression of CTLA-4, a Second Receptor for B7," *Journal of Immunology*, vol. 152, pp. 2686-2697 (1994).

Damle, N.K. et al., "Differential Regulatory Signals Delivered by Antibody Binding to the CD28 Molecule (Tp44) During the Activation of Human T Lymphocytes," *The Journal of Immunology*, vol. 140, No. 6, pp. 1753-1761 (1988).

Davis, MM. et al., "T-cell antigen receptor genes and T-cell recognition," *Nature*, vol. 334, pp. 395-402 (1988).

de Boer, M. et al., "Ligation of B7 with CD28/CTLA-4 on T-cells results in CD40 ligand expression, interleukin-4 secretion and efficient help for antibody production by B cells," *Eur. J. Immunol.*, vol. 23, pp. 3120-3125 (1993).

deWaal, M. et al., "Direct Effects of IL-10 on Subsets of Human CD4+ T Cell Clones and Resting T Cells. Specific Inhibition of IL-2 Production and Proliferation," *The Journal of Immunology*, vol. 150, No. 11, pp. 4754-4765 (1993).

Ding, L. et al., "IL-10 Inhibits Macrophage Costimulatory Activity by Selectively Inhibiting Up-Regulation of B7 Expression," *The Journal of Immunology*, vol. 151, No. 3, pp. 1224-1234 (1993).

Donnelly, J.J. et al., "DNA Vaccines," *Annu. Rev. Immunol.*, vol. 15, pp. 617-648 (1997).

Driscoll, P.C. et al., "Structure of domain 1 of rat T-lymphocyte CD2 antigen," *Nature*, vol. 353, pp. 762-765 (1991).

Ellis. J.H. et al.. "Interactions of CD80 and CD86 with CD28 and CTLA4," *The Journal of Immunology*, vol. 56, pp. 2700-2709 (1996).

Englehard, V.H., "Structure of peptides associated with MHC class I molecules," *Current Opinion in Immunology*, vol. 6, pp. 13-21 (1994).

English, R.V. et al., "Development of Clinical Disease in Cats Experimentally Infected With Feline Immunodeficiency Virus," *The Journal of Infectious Diseases*, vol. 170, pp. 545-555: (1994).

Fauci, A., et al., "Acquired Immunodeficiency Syndrome: Epidemiologic, Clinical, Immunologic, and Therapeutic Considerations," *Annals of Internal Medicine*, vol. 100, pp. 92-106 (1984).

Fauci, A.S. et al., "The Effect of Hydrocortisone on the Kinetics of Normal Human Lymphocytes," *Blood*, vol. 46, No. 2, pp. 235-243 (1975).

Ferrari, F.A. et al., "Sequence Analysis of the spo0B Locus Reveals a Polycistronic Transcription Unit," *Journal of Bacteriology*, vol. 161, No. 2, pp. 556-562 (1985).

Fong, T.A.T. et al., "Alloreactive Murine CD8+ T Cell Clones Secrete the Thl Pattern of Cytokines," *The Journal of Immunology*, vol. 144, No. 5, pp. 1744-1752(1990).

Fouchier, R.A. et al., "Broader Tropism and Higher Cytopathicity for CD4+ T Cells of a Syncytium-Inducing Compared to a Non-Syncytium-Inducing HIV-1 Isolate as a Mechanism for Accelerated CD4+ T Cell Decline in Vivo," *Virology*, vol. 219, pp. 87-95 (1996).

Freedman, A.S. et at, "B7, A B-Cell-Restricted Antigen That Identifies Preactivated B Cells," *The Journal of Immunology*, vol. 139, No. 10, pp. 3260-3267 (1987).

Freeman et al., "Structure, Expression, and T Cell Costimulatory Activity of the Murine Homologue of the Human B Lymphocyte Activation Antigen B7," *J. Exp. Med.*, vol. 174, pp. 625-631 (1991).

Freeman, G.J. et al., "B7, A New Member of the Ig Superfamily With Unique Expression or Activated and Neoplastic B Cells," *The Journal of Immunology*, vol. 143, No. 8, pp. 2714-2722 (1989).

Freeman, G.J. et al., "Uncovering a Functional Alternative CTLA-4 Counter-Receptor in B7-Deficient Mice," *Science*, vol. 262, pp. 907-909 (1993).

Freeman, G.J. et al., "Murine B7-2, an Alternative CTLA4 Counter-receptor that Costimulates T Cell Proliferation and Interleukin 2 Production", *Journal of Experimental Medicine*, vol. 178(6), pp. 2185-2192 (1993).

Gajewski, T.F. et al., "Regulation of T-Cell Activation: Differences among T-Cell Subsets," *Immunological Reviews*, vol. 111, pp. 79-110 (1989).

Germain R.N., "The Biochemistry and Cell Biology of Antigen Processing and Presentation," *Annu. Rev. Immunol*, vol. 11, pp. 403-450 (1993).

Gimmi, C.D. et al., "B-cell surface antigen B7 provides a costimulatory signal that induce: T cells to proliferate and secrete interleukin 2," *Proc. Natl. Acad. Sci. USA*, vol. 88, pp. 6575-6579 (1991).

Haffar, O.K. et al., "Costimulation of T-cell activation and virus production by B7 antigen on activated CD4+ T cells from human immunodeficiency virus type 1-infected donors," *Proc. Natl. Acad. Sci. USA*, vol. 90, pp. 11094-11098 (1993).

Harlan, D.M. et al., "Potential Roles of the B7 and CD28 Receptor Families in Autoimmunity and Immune Evasion," *Clinical Immunology and Immunopatholgy*, vol. 75, No. 2, pp. 99-111 (1995).

Hash, S.M., "Cloning, Sequencing, Expression and Characterization of the Feline CD28/CD80 Accessory Signaling Complex," Ph.D. Dissertation, Texas A&M University, U.S.A. (1997).

Hassett, D.E. et al., "DNA immunization," *Trends in Microbiology*, vol. 4, No. 8, pp. 307-312 (1996).

Hathcock, K.S. et al., Comparative Analysis of B7-1 and B7-2 Costimulatory Ligands: Expression and Function, *The Jounral of Experimental Medicine*, vol. 180, 631-640 (1994).

Hodge, J.W. et al., "Induction of Antitumor Immunity by Recombinant Vaccinia Viruses Expressing B7-1 or B7-2 Costimulatory Molecules," *Cancer Research*, vol. 54, pp. 5552-5555 (1994).

Hutchcroft, J.E. et al., "Signaling Through CD28/CTLA-4 Family Receptors: Puzzling Participation of Phosphatidylinosito1-3 Kinase," *The Journal of Immunology*, vol. 155, pp. 4071-4074 (1996).

Isono, T. and Seto, A., "Cloning and Sequencing of the Rabbit Gene Encoding T-Cell Costimulatory Molecules", *Immunogenetics*, vol. 42(3), 1995, p. 217-220.

Jenkins, M.K. et al., "CD28 Delivers a Costimulatory Signal Involved in Antigen-Specific IL-2 Production by Human T Cells," *The Journal of Immunology*, vol. 147, No. 8, pp. 2461-2466 (1991).

Jenkins, M.K. et al., "T-Cell Unresponsiveness in vivo and in vitro: Fine Specificity of Induction and Molecular Characterization of the Unresponsive State," *Immunological Reviews*, vol. 95, pp. 113-135 (1987).

June, C.H. et al., "Role of the CD28 receptor in T-cell activiation," *Immunology Today*, vol. 11, No. 6, pp. 211-216 (1990).

June, C.H. et al., "The B7 and CD28 receptor families," *Immunology Today*, vol. 15, No. 7, pp. 321-333 (1994). Knight, J.C. et al., *Virology*, vol. 190, pp. 423-433 (1992).

Kozbor, D. et al., "Tp44 Molecules Involved in Antigen-Independent T Cell Activation are Expressed on Human Plasma Cells," *The Journal of Immunology*, vol. 138, No. 12, pp. 4128-4132 (1987).

Kupfer, A. et al., "Cell Biology of Cytotoxic and Helper T Cell Functions: Immunofluorescence Microscopic Studies of Single Cells and Cell Couples," *Annu. Rev. Immunol.*, vol. 7, pp. 309-337 (1989).

Landay, A.L. et al., "An Activated CD8+ 3T Cell Phenotype Correlates with Anti-HIV Activity and Asymptomatic Clinical Status," *Clinical Immunology and Immunopathology*, vol. 69, No. 1, pp. 106-116 (1993).

Lane, P. et al., "B Cell Function in Mice Transgenic for mCTLA4-Hγ1: Lack of Germinal Centers Correlated with Poor Affinity Maturation and Class Switching Despite Normal Priming of CD4+ T Cells," *J. Exp. Med.*, vol. 179, pp. 819-830 (1994).

Lanier, L.L. et al., "CD80 (B7) and CD86 (B70) Provide Similar Costimulatory Signals for T Cell Proliferation, Cytokine Production, and Generation of CTL," *The Journal of Immunology*, vol. 154, pp. 97-105 (1995).

Larsen, C.P. et al., "Functional Expression of the Costimulatory Molecule, B7/BB1, on Murine Dendritic Cell Populations," *J. Exp. Med.*, vol. 176, pp. 1215-1220 (1992).

Leahy, D. J. et al., "Crystal Structure of a Soluble Form of the Human T Cell Coreceptor CD8 at 2.6 A Resolution," *Cell*, vol. 68, pp. 1145-1162 (1992).

Lechler, R.I. et al., "The molecular basis of alloreactivity," *Immunology Today*, vol. 11, No. 3, pp. 83-88 (1990).

Lenschow, D.J. et al., "CD28/B7 System of T Cell Costimulation," *Annu. Rev. Immunol.*, vol. 14, pp. 233-258 (1996).

Lenschow, D.J. et al., "Expression and functional significance of an additional ligand for CTLA-4," *Proc. Nat. Acad. Sci. USA*, vol. 90, pp. 11054-11058 (1993).

Leung, H.T. et al., "The CD28 costimulatory pathway," *Therapeutic Immunology*, vol. 1, pp. 217-228 (1994).

Lewis, D.E. et al., "Anergy and Apoptosis in CD8+ T Cells from HIV Infected Persons," *The Journal of Inmninology*, vol. 153, pp. 412-420 (1994).

Li, Y. et al., "Costimulation of Tumor Reactive CD4+ and CD8+ T Lymphocytes by B7, a Natural Ligand for CD28, Can Be Used to Treat Established Mouse Melanoma," *The Journal of Immunology*, vol. 153, pp. 421-428 (1994).

Lindsten, T. et al., "Characterization of CTLA-4 Structure and Expression on Human T Cells," *The Journal of Immunology*, vol. 151, pp. 3489-3499 (1993).

Linsley, P. S. et al., "T-cell antigen CD28 mediates adhesion with B cells by interacting with activation antigen B7IBB-1," *Proc. Natl. Acad. Sci. USA*, vol. 87, pp. 5031-5035 (1990).

Linsley, P.S. et al., "Binding of the B Cell Activation Antigen B7 to CD28 Costimulates T Cell Proliferation and Interleukin 2 mRNA Accumulation," *J. Exp. Med.*, vol. 173, pp. 721-730 (1991).

Linsley, P.S. et al., "Binding Stoichiometry of the Cytotoxic T Lymphocyte-associated Molecule-4 (CTLA-4)," *The Journal of Biological Chemistry*, vol. 270, No. 25, 15417-15424 (1995).

Linsley, P.S. et al., "CD28 Engagement by B7/BB-1 Induces Transient Down-Regulation of CD28 Synthesis and Prolonged Unresponsiveness to CD28 Signaling," *The Journal of Immunology*, vol. 150, No. 8, pp. 3161-3169 (1993).

Linsley, P.S. et al., "CD28/CTLA-4 receptor structure, binding stoichiometry and aggregation during T-cell activation," *Res. Immunol*, vol. 146, pp. 130-140 (1995).

Linsley, P.S. et al., "Coexpression and Functional Cooperation of CTLA-4 and CD28 on Activated T Lymphocytes," *J. Exp. Med.*, vol. 176, pp. 1595-1604 (1992).

Linsley, P.S. et al., "CTLA-4 is a Second Receptor for the B Cell Activation Antigen B7," *J. Exp. Med.*, vol. 174, pp. 561-569 (1991).

Linsley, P.S. et al., "Extending the B7 (CD80) gene family," *Protein Science*, vol. 3, pp. 1341-1343 (1994).

Linsley, P.S. et al., "Human B7-1 (CD80) and B7-2 (CD86) Bind with Similar Avidities but Distinct Kinetics to CD28 and CTLA-4 Receptors," *Immunity*, vol. 1, pp. 793-801 (1994).

Linsley, P.S. et al., "Immunosuppression in Vivo by a Soluble Form of the CTLA-4 T Cell Activation Molecule," *Science*, vol. 257, pp. 792-795 (1992).

Linsley, P.S. et al., "The Role of CD28 Receptor During T Cell Responses to Antigen," *Annu. Rev. Immunol.*, vol. 11, pp. 191-212 (1993).

Littman, D.R, "The Structure of the CD4 and CD8 Genes," *Ann. Rev. Immunol*, vol. 5, pp. 561-584 (1987).

Liu, C.C. et al., "Perforin: structure and function," *Immunology Today*, vol. 16, No. 4, pp. 194-201 (1995).

Liu, Y. et al., "Co-stimulation of murine CD4 T cell growth: cooperation between B7 and heat-stable antigen," *Eur. J. Immunol*, vol. 22, pp. 2855-2859 (1992).

Lombardi, S. et al., "A Neutralizing Antibody-Inducing Peptide of the V3 Domain of Feline Immunodeficiency Virus Envelope Glycoprotein Does Not Induce Protective Immunity," *The Journal of Virology*, vol. 68, No. 12, pp. 8374-8379 (1994).

Lu, Y. et al., "CD28-Induced T Cell Activation. Evidence for a Protein-Tyrosine Kinase Signal Transduction Pathway," *The Journal of Immunology*, vol. 149, No. 1, pp. 24-29 (1992).

Lwoff, A., "The Concept of Virus," *The Journal of General Microbiology*, vol. 17, No. 1, pp. 239-253 (1957).

Maeda, K. et al., "Characterization of Rat CD80 and CD86 by Molecular Cloning and mAb", *International Immunology*, vol. 9(7), 1997, p. 993-1000.

Maher, S. E. "Porcine Endothelial CD86 Is a Major Costimulator of Xenogeneic Human T Cells," Journal of Immunology, vol. 157, No. 9, pp. 3828-3844, Nov. 1, 1996.

Martin, P.J. et al., "A 44 Kilodalton Cell Surface Homodimer Regulates Interleukin 2 Production by Activated Human T Lymphocytes," *The Journal of Immunology*, vol. 136, No. 9, pp. 3282-3287 (1986).

Matasumura, M. et al., Emerging Principles for the Recognition of Peptide Antigens by MHC Class I Molecules, *Science*, vol. 257, pp. 927-934 (1992).

Mescher, M.F., "Surface Contact Requirements for Activation of Cytotoxic T Lymphocytes," *The Journal of Immunology*, vol. 149, No. 7, pp. 2402-2405 (1992).

Minty, A. et al., "Interleukin-13 is a new human lymphokine regulating inflammatory and immune responses," *Nature*, vol. 362, pp. 248-250 (1993).

Moffett, C.W. et al., "Microglia in the rat neurohypophysis increase expression of class I major histocompatibility antigens following central nervous system injury," *Journal of Neuroimmunology*, vol. 50, pp. 139-151 (1994).

Mosmann, T. R. et al., "TH1 and TH2 Cells: Different Patterns of Lymphokine Secretion Lead to Different Functional Properties," *Ann. Rev. Immunol*, vol. 7, pp. 145-173 (1989).

Nabavi, N. et al., "Signaling through the MHC Class II cytoplasmic domain is required for antigen presentation and induces B7 expression," *Nature*, vol. 360, pp. 266-268 (1992).

Nagata, S. et al., "The Fas Death Factor," *Science*, vol. 267, pp. 1449-1456 (1995).

Nickoloff, B.J. et al., "Discordant Expression of CD28 Ligands, BB-1 and B7 on Keratinocytes in Vitro and Psoriatic Cells in Vivo," *American Journal of Pathology*, vol. 142, No. 4, pp. 1029-1040(1993).

Nishimura, Y. et al., "Molecular cloning of the cDNAs encoding the feline B-lymphocyte activation antigen B7-1 (CD80) and B7-2 (CD86) homologues which interact with human CTLA4-Ig," *European Journal of Immunogenetics*, vol. 27, No. 5-6, pp. 427-430, Oct. 2000.

Novotney, C. et al., "Lymphocyte population changes in cats naturally infected with feline immunodeficiency virus," AIDS, vol. 4, pp. 1213-1218 (1990).

O'Doherty, U. et al., "Dendritic cells freshly isolate from human blood express CD4 and mature into typical immunostimulatory dendritic cells after culture in monocyte conditioned media," *J. Exp, Med.*, vol. 178, pp. 1067-1076 (1993).

Ozawa, H. et al., "Interferon gamma and interleukin 10 inhibit antigen presentation by Langerhans cells for T helper type 1 cells by suppressing their CD80 (B7-1) expression," *Eur. J. Immunol.*, vol. 26, pp. 648-652 (1996).

Page, C. et al., "Human endothelial stimulation of allogenic T cells via a CTLA-4 independent pathway," *Transplant Immunology*, vol. 2, pp. 342-347 (1994).

Peach, R. J. et al., "Both Extracellular Immunoglobulin-like Domains of CD80 Contain Residues Critical for Binding T Cell Surface Receptors CTLA-4 and CD28," *The Journal of Biological Chemistry*, vol. 26, pp. 648-652 (1995).

Peach, R.J. et al., "Complementarity Determining Region 1 (CDR1)- and CDR3-analogous Regions in CTLA-4 and CD28 Determine the Binding to B7-1," *J. Exp. Med.*, vol. 180, pp. 2049-2058 (1994).

Pedersen, N.C. et al., "Isolation of a T-Lymphotropic Virus from Domestic Cats with an Immunodeficiency-Like Syndrome," *Science*, vol. 235, pp. 790-793 (1987).

Prasad, K.V.S et al., "T-cell antigen CD28 interacts with the lipid kinase phosphatidylinositol 3-kinase by a cytoplasmic Tyr(P)-Met-Xaa-Met motif," *Proc. Natl. Acad. Sci. USA*, vol. 91, pp. 2834-2838 (1994).

Radvanyi, L.G. et al., "CD28 Costimulation Inhibits TCR-Induced Apoptosis During a Primary T-Cell Response," *The Journal of Immunology*, vol. 156, pp. 1788-1798 (1996).

Ranheim, E.A. et al., "Tumor Necrosis Factor-alpha. Facilitates Induction of CD80 (B7-1) and CD54 on Human B Cells By Activated T Cells: Complex Regulation by IL-4, IL-10, and CD40L," *Cellular Immunology*, vol. 161, pp. 226-235 (1995).

Razi-Wolf, Z. et al., "Expression and function of the murine B7 antigen, the major costimulatory molecule expressed by peritoneal exudate cells," *Proc. Natl. Acad. Sci USA*, vol. 89, pp. 4210-4214 (1992).

Riley, J.L. et al., "Intrinsic Resistance to T Cell Infection with HIV Type 1 Induced by CD28 Costimulation," *The Journal of Immunology*, vol. 158, pp. 5545-5553 (1997).

Ronchese, F. et al., "Mice Transgenic for a Soluble Form of Murine CTLA-4 Show Enchanced Expansion of Antigen-Specific CDA+ T Cells and Defective Antibody Production In Vivo," *J. Exp. Med.*, vol. 179, pp. 809-817 (1994).

Rotzschke, O. et al., "Origin, structure and motifs of naturally processed MHC class II ligands," *Current Opinion in Immunology*, vol. 6, pp. 45-51 (1994).

Russel, J.H., "Internal Disintegration Model of Cytotoxic Lymphocyte-Induced Target Damage," *Immunological Rev.*, vol. 72, pp. 97-118 (1983).

Sands, et al., "Biodistribution and metabolism of internally 3H-labeled oligonucleotides. I. Comparison of a phosphodiester and a phosphorothioate," *Molecular Pharmacology*, vol. 45, pp. 932-943 (1994).

Saukkonen, J.J. et al., "Expansion of a CD8+ CD28- Cell Population in the Blood and Lung of HIV-Positive Patients," *Journal of Acquired Immune Deficiency Syndromes*, vol. 6, pp. 1194-1204 (1993).

Schattner, E. et al., "HIV-Induced T-Lymphocyte Depletion," *Clinics in Laboratory Medicine*, vol. 14, No. 2, pp. 221-238 (1994).

Schmittel, A. et al., "Lipopolysacchaaride Effectively Up-Regulates B7-1 (CD80) Expression and Costimulatory Function of Human Monocytes," *Scand. J. Immunol*, vol. 42, pp. 701-704 (1995).

Schwartz, R.H., "Costimulation of T Lymphocytes: The Role of CD28, CTLA-4 and B7/BB1 in Interleukin-2 Production and Immunotherapy," *Cell*, vol. 71, pp. 1065-1068 (1992).

Seder, R.A. et al., "CD28-mediated Costimulation of Interleukin 2 (IL-2) Production Plays a Critical Role in T Cell Priming for IL-4 and Interferon γ Production," *The Journal of Experimental Medicine*, vol. 179, pp. 299-304 (1994).

Shahinian, A. et al., "Differential T Cell Costimulatory Requirements in CD28-Deficient Mice," *Science*, vol. 261, pp. 609-612 (1993).

Sher, A. et al., "Role of T-Cell Derived Cytokines in the Downregulation of Immune Responses in Parasitic and Retroviral Infection," *Immunological Reviews*, No. 127, pp. 183-204 (1992).

Siebelink, K.H.J. et al., "Enhancement of Feline Immunodeficiency Virus Infection after Immunization with Envelope Glycoprotein Subunit Vaccines," *Journal of Virology*, vol. 69, No. 6, pp. 3704-3711 (1995).

Siebelink, K.H.J. et al., "Feline Immunodeficiency Virus (FIV) Infection in the Cat as a Model for HIV Infection *in Man*: FIV-Induced Impairment of Immune Function," *AIDS Research and Human Retroviruses*, vol. 6, No. 12, pp. 1373-1378 (1990).

Singer, S.J., "Intercellular Communication and Cell-Cell Adhesion," *Science*, vol. 255, pp. 1671-1674 (1992).

Smithgall, M.D. et al., "Costimulation of CD4+ T Cells via CD28 Modulates Human Immunodeficiency Virus Type I Infection and Replication in Vitro," *AIDS Research and Human Retroviruses*, vol. 11, No. 8, pp. 885-892 (1995).

Springer, T.A. et al., "The Lymphocyte Function-Associated LFA-1, CD2, and LFA-3 Molecules: Cell Adhesion Receptors of the Immune System," *Annu. Rev. Immunol.*, vol. 5, pp. 223-252 (1987).

Springer, T.A., "Adhesion receptors of the immune system," *Nature*, vol. 346, pp. 425-434 (1990).

Stack, R.M. et al., "IL-4 Treatment of Small Splenic B Cells Induces Costimulatory Molecules B7-1 and B7-2," *Journal of Immunology*, vol. 152, pp. 5723-5733 (1994).

Symington, F.W. et al., "Expression and Function of B7 on Human Epidermal Langerhans Cells," *The Journal of immunology*, vol. 150, No. 4, pp. 1286-1295 (1993).

Taylor, M.K. et al., "Cell-mediated cytotoxicity," *Current Opinion in Immunology*, vol. 4, pp. 338-343 (1992).

Thomas, R. et al., "Rheumatoid Synovium is Enriched in Mature Antigen-Presenting Dendritic Cells," *Journal of Immunology*, vol. 152, pp. 2613-2623 (1994).

Townsend, S.E. et al., "Tumor Rejection After Direct Costimulation of CD8+ T Cells by B7-Transfected Melanoma Cells," *Science*, vol. 259, pp. 368-370 (1993).

Tsuji, T. et al., "Immunomodulatory effects of a plasmid expressing B7-2 on human immunodeficiency virus-1-specific cell-mediated immunity induced by a plasmid encoding the viral antigen," *Eur. J Immunol.*, vol. 27, pp. 782-787 (1997).

Turka, L.A. et al., "CD28 is an Inducible T Cell Surface Antigen That Transduces a Proliferative Signal in CD3+ Mature Thymocytes," *The Journal of Immunology*, vol. 144, No. 5, pp. 1646-1653 (1990).

Turka, L.A. et al., "Signal Transduction Via CD4, CD8, and CD28 in Mature and Immature Thymocytes," *The Journal of Immunology*, vol. 146, No. 5, pp. 1428-1436 (1991).

Unanue, E.R., "Antigen-Presenting Function of the Macrophage," *Annu. Rev. Immunol*, vol. 2, pp. 395-428 (1984).

van Kooten, C. et al., "Monokine Production by Human T Cells: IL-1α Production Restricted to Memory T Cells," *The Journal of Immunology*, vol. 146, No. 8, pp. 2654-2658 (1991).

van Seventer, G.A. et al., "Roles of multiple accessory molecules in T-cell activation," *Current Opinion in Immunology*, vol. 3, pp. 294-303 (1991).

Wang, R. et al., "Differential Activation of Antigen-Stimulated Suicide and Cytokine Production Pathways in CD4+T Cells is Regulated by the Antigen-Presenting Cell," *The Journal of Immunology*, vol. 150, No. 9, pp. 3832-3842 (1993).

Weiss, A. et al., "Signal Transduction by Lymphocyte Antigen Receptors," *Cell*, vol. 76, pp. 263-274 (1994).

Williams, A.F. et a/., The Immunoglobulin Superfamily-Domains for Cell Surface Recognition, *Annu. Rev. Immunol.*, vol. 6, pp. 381-405 (1988).

Windhagen, A. et al., "Expression of Costimulatory Molecules B7-1 (CD80), B7-2 (CD86) and Interleukin 12 Cytokine in Multiple Sclerosis Lesions," *J. Exp. Med.*, vol. 182, pp. 1985-1996 (1995).

Yamamoto, J.K. et al., "Epidemiologic and clinical aspects of feline immunodeficiency virus infection in cats from the continental United States and Canada and possible mode of transmission," *JAVMA*, vol. 194, No. 2, pp. 213-220 (1989).

Yasukawa, M. et al., "Differential in Vitro activation of CD4+CD8- and CD8+CD4- Herpes Simplex Virus-Specific Human Cytotoxic T Cells," *The Journal of Immunology*, vol. 143, No. 6, pp. 2051-2057 (1989).

Yssel, et al., "Interleukin-7 specifically induces the B7/BB1 antigen on human cord blood and peripheral blood T cells and T cell clones," *Int. Immunol*, vol. 5, No. 7, pp. 753-759 (1993).

Zanussi, S. et al., "CD8+ lymphocyte phenotype and cytokine production in long-term non-progressor and in progressor patients with HIV-1 infection," *Clin. Exp. Immunol.*, vol. 105, pp. 220-224 (1996).

Zhou, T. et al., "T cells of staphylococcal enterotoxin B-tolerized autoimmune MRL-lpr/lpr mice require co-stimulation through the B7-CD28/CTLA-4 pathway for activation and can be reanergized in vivo by stimulation of the T cell receptor in the absence of costimulatory signal," *Eur. J. Immunol.*, vol. 24, pp. 1019-1025 (1994).

Database WP1 Section Ch, Week 199804, Derwent Publications Ltd., London, GB; AN 1998-037055, XP00226603.

English Patent Abstract to Japanese Publication No. 09-291100 (Database WP1 Accession No. 1998-037055).

FIG. 1A-1

FeB71.TAMU

```
ATGGGTCACGCAGCAAAGTGGAAAACACCACTACTGAAGCACCCATATCCCAAGCTCTTT   60
 Met Gly His Ala Ala Lys Trp Lys Thr Pro Leu Leu Lys His Pro Tyr Pro Lys Leu Phe

CCGCTCTTGATGCTAGCTAGTCTTTTTTACTTCTGTTCAGGTATCATCCAGGTGAACAAG   120
 Pro Leu Leu Met Leu Ala Ser Leu Phe Tyr Phe Cys Ser Gly Ile Ile Gln Val Asn Lys

ACAGTGGAAGAAGTAGCAGTACTATCCTGTGATTACAACATTTCCACCAAAGAACTGACG   180
 Thr Val Glu Glu Val Ala Val Leu Ser Cys Asp Tyr Asn Ile Ser Thr Lys Glu Leu Thr

GAAATTCGAATCTATTGGCAAAAGGATGATGAAATGGTGTTGGCTGTCATGTCTGGCAAA   240
 Glu Ile Arg Ile Tyr Trp Gln Lys Asp Asp Glu Met Val Leu Ala Val Met Ser Gly Lys

GTACAAGTGTGGCCCAAGTACAAGAACCGCACATTCACTGACGTCACCGATAACCACTCC   300
 Val Gln Val Trp Pro Lys Tyr Lys Asn Arg Thr Phe Thr Asp Val Thr Asp Asn His Ser

ATTGTGATCATGGCTCTGCGCCTGTCAGACAATGGCAAATACACTTGTATTATTCAAAAG   360
 Ile Val Ile Met Ala Leu Arg Leu Ser Asp Asn Gly Lys Tyr Thr Cys Ile Ile Gln Lys

ATTGAAAAAGGGTCTTACAAAGTGAAACACCTGACTTCGGTGATGTTATTGGTCAGAGCT   420
 Ile Glu Lys Gly Ser Tyr Lys Val Lys His Leu Thr Ser Val Met Leu Leu Val Arg Ala

GACTTCCCTGTCCCTAGTATAACTGATCTTGGAAATCCATCTCATAACATCAAAAGGATA   480
 Asp Phe Pro Val Pro Ser Ile Thr Asp Leu Gly Asn Pro Ser His Asn Ile Lys Arg Ile

ATGTGCTTAACTTCTGGAGGTTTTCCAAAGCCTCACCTCTCCTGGCTGGAAAATGAAGAA   540
 Met Cys Leu Thr Ser Gly Gly Phe Pro Lys Pro His Leu Ser Trp Leu Glu Asn Glu Glu

GAATTAAATGCCATCAACACAACAGTTTCCCAAGATCCTGAAACTGAGCTCTACACTATT   600
 Glu Leu Asn Ala Ile Asn Thr Thr Val Ser Gln Asp Pro Glu Thr Glu Leu Tyr Thr Ile

AGCAGTGAACTGGATTTCAATATGACAAACAACCATAGCTTCCTGTGTCTTGTCAAGTAT   660
 Ser Ser Glu Leu Asp Phe Asn Met Thr Asn Asn His Ser Phe Leu Cys Leu Val Lys Tyr
```

FIG. 1A-2

GGAAACTTACTAGTATCACAGATCTTCAACTGGCAAAAATCAGAGCCACAGCCTTCTAAT 720
Gly Asn Leu Leu Val Ser Gln Ile Phe Asn Trp Gln Lys Ser Glu Pro Gln Pro Ser Asn

AATCAGCTCTGGATCATTATCCTGAGCTCAGTAGTAAGTGGGATTGTTGTGATCACTGCA 780
Asn Gln Leu Trp Ile Ile Ile Leu Ser Ser Val Val Ser Gly Ile Val Val Ile Thr Ala

CTTACCTTAAGATGCCTAGTCCACAGACCTGCTGCAAGGTGGAGACAAAGAGAAATGGGG 840
Leu Thr Leu Arg Cys Leu Val His Arg Pro Ala Ala Arg Trp Arg Gln Arg Glu Met Gly

AGAGCGCGGAAATGGAAAAGATCTCACCTGTCTACATAGATTCTGCAGAACCACTGTATG 900
Arg Ala Arg Lys Trp Lys Arg Ser His Leu Ser Thr

CAGAGCATCTGGAGGTAGCCTCTTTAGCTCTTCTCTACTAG 941

FIG. 2A-1

FeB71-SYNTRO

ATGGGTCACGCAGCAAAGTGGAAAACACCACTACTGAAGCACCCATATCCCAAGCTCTTT 60
Met Gly His Ala Ala Lys Trp Lys Thr Pro Leu Leu Lys His Pro Tyr Pro Lys Leu Phe

CCGCTCTTGATGCTAGCTAGTCTTTTTTACTTCTGTTCAGGTATCATCCAGGTGAACAAG 120
Pro Leu Leu Met Leu Ala Ser Leu Phe Tyr Phe Cys Ser Gly Ile Ile Gln Val Asn Lys

ACAGTGGAAGAAGTAGCAGTACTATCCTGTGATTACAACATTTCCACCAAAGAACTGACG 180
Thr Val Glu Glu Val Ala Val Leu Ser Cys Asp Tyr Asn Ile Ser Thr Lys Glu Leu Thr

GAAATTCGAATCTATTGGCAAAAGGATGATGAAATGGTGTTGGCTGTCATGTCTGGCAAA 240
Glu Ile Arg Ile Tyr Trp Gln Lys Asp Asp Glu Met Val Leu Ala Val Met Ser Gly Lys

GTACAAGTGTGGCCCAAGTACAAGAACCGCACATTCACTGACGTCACCGATAACCACTCC 300
Val Gln Val Trp Pro Lys Tyr Lys Asn Arg Thr Phe Thr Asp Val Thr Asp Asn His Ser

ATTGTGATCATGGCTCTGCGCCTGTCAGACAATGGCAAATACACTTGTATCATTCAAAAG 360
Ile Val Ile Met Ala Leu Arg Leu Ser Asp Asn Gly Lys Tyr Thr Cys Ile Ile Gln Lys

ATTGAAAAAGGGTCTTACAAAGTGAAACACCTGACTTCGGTGATGTTATTGGTCAGAGCT 420
Ile Glu Lys Gly Ser Tyr Lys Val Lys His Leu Thr Ser Val Met Leu Leu Val Arg Ala

GACTTCCCTGTCCCTAGTATAACTGATCTTGGAAATCCATCTCATAACATCAAAAGGATA 480
Asp Phe Pro Val Pro Ser Ile Thr Asp Leu Gly Asn Pro Ser His Asn Ile Lys Arg Ile

ATGTGCTTAACTTCTGGAGGTTTTCCAAAGCCTCACCTCTCCTGGCTGGAAAATGAAGAA 540
Met Cys Leu Thr Ser Gly Gly Phe Pro Lys Pro His Leu Ser Trp Leu Glu Asn Glu Glu

GAATTAAATGCCATCAACACAACAGTTTCCCAAGATCCTGAAACTGAGCTCTACACTATT 600
Glu Leu Asn Ala Ile Asn Thr Thr Val Ser Gln Asp Pro Glu Thr Glu Leu Tyr Thr Ile

AGCAGTGAACTGGATTTCAATATGACAAACAACCATAGCTTCCTGTGTCTTGTCAAGTAT 660
Ser Ser Glu Leu Asp Phe Asn Met Thr Asn Asn His Ser Phe Leu Cys Leu Val Lys Tyr

FIG. 2A-2

```
GGAAACTTAATAGTATCACAGATCTTCAACTGGCAAAAATCAGAGCCACAGCCTTCTAAT 720
Gly Asn Leu Ile Val Ser Gln Ile Phe Asn Trp Gln Lys Ser Glu Pro Gln Pro Ser Asn

AATCAGCTCTGGATCATTATCCTGAGCTCAGTAGTAAGTGGGATTGTTGTGATCACTGCA 780
Asn Gln Leu Trp Ile Ile Ile Leu Ser Ser Val Val Ser Gly Ile Val Val Ile Thr Ala

CTTACCTTAAGATGCCTAGTCCACAGACCTGCTGCAAGGTGGAGACAAAGAGAAATGGGG 840
Leu Thr Leu Arg Cys Leu Val His Arg Pro Ala Ala Arg Trp Arg Gln Arg Glu Met Gly

AGAGCGCGGAAATGGAAAAGATCTCACCTGTCTACATAG 879
Arg Ala Arg Lys Trp Lys Arg Ser His Leu Ser Thr
```

FIG. 3A-1

FeB72

```
GTTTCTGTGTTCCTCGGGAATGTCACTGAGCTTATACATCTGGTCTCTGGGAGCTGCAGT    60
GGATGGGCATTTGTGACAGCACTATGGGACTGAGTCACACTCTCCTTGTGATGGCCCTCC
     Met Gly Ile Cys Asp Ser Thr Met Gly Leu Ser His Thr Leu Leu Val Met Ala Leu   120
```

```
TGCTCTCTGGTGTTTCTTCCATGAAGAGTCAAGCATATTTCAACAAGACTGGAGAACTGC
Leu Leu Ser Gly Val Ser Ser Met Lys Ser Gln Ala Tyr Phe Asn Lys Thr Gly Glu Leu   180
```

```
CATGCCATTTTACAAACTCTCAAAACATAAGCCTGGATGAGCTGGTAGTATTTTGGCAGG
Pro Cys His Phe Thr Asn Ser Gln Asn Ile Ser Leu Asp Glu Leu Val Val Phe Trp Gln   240
```

```
ACCAGGATAAGCTGGTTCTGTATGAGATATTCAGAGGCAAAGAGAACCCTCAAAATGTTC
Asp Gln Asp Lys Leu Val Leu Tyr Glu Ile Phe Arg Gly Lys Glu Asn Pro Gln Asn Val   300
```

```
ATCTCAAATATAAGGGCCGTACAAGCTTTGACAAGGACAACTGGACCCTGAGACTCCACA
His Leu Lys Tyr Lys Gly Arg Thr Ser Phe Asp Lys Asp Asn Trp Thr Leu Arg Leu His   360
```

```
ATGTTCAGATCAAGGACAAGGGCACATATCACTGTTTCATTCATTATAAAGGGCCCAAAG
Asn Val Gln Ile Lys Asp Lys Gly Thr Tyr His Cys Phe Ile His Tyr Lys Gly Pro Lys   420
```

```
GACTAGTTCCCATGCACCAAATGAGTTCTGACCTATCAGTGCTTGCTAACTTCAGTCAAC
Gly Leu Val Pro Met His Gln Met Ser Ser Asp Leu Ser Val Leu Ala Asn Phe Ser Gln   480
```

```
CTGAAATAACAGTAACTTCTAATAGAACAGAAAATTCTGGCATCATAAATTTGACCTGCT
Pro Glu Ile Thr Val Thr Ser Asn Arg Thr Glu Asn Ser Gly Ile Ile Asn Leu Thr Cys   540
```

```
CATCTATACAAGGTTACCCAGAACCTAAGGAGATGTATTTTCAGCTAAACACTGAGAATT
Ser Ser Ile Gln Gly Tyr Pro Glu Pro Lys Glu Met Tyr Phe Gln Leu Asn Thr Glu Asn   600
```

```
CAACTACTAAGTATGATACTGTCATGAAGAAATCTCAAAATAATGTGACAGAACTGTACA
Ser Thr Thr Lys Tyr Asp Thr Val Met Lys Lys Ser Gln Asn Asn Val Thr Glu Leu Tyr   660
```

```
ACGTTTCTATCAGCTTGCCTTTTTCAGTCCCTGAAGCACACAATGTGAGCGTCTTTTGTG
Asn Val Ser Ile Ser Leu Pro Phe Ser Val Pro Glu Ala His Asn Val Ser Val Phe Cys   720
```

```
CCCTGAAACTGGAGACACTGGAGATGCTGCTCTCCCTACCTTTCAATATAGATGCACAAC
Ala Leu Lys Leu Glu Thr Leu Glu Met Leu Leu Ser Leu Pro Phe Asn Ile Asp Ala Gln   780
```

```
CTAAGGATAAAGACCCTGAACAAGGCCACTTCCTCTGGATTGCGGCTGTACTTGTAATGT
Pro Lys Asp Lys Asp Pro Glu Gln Gly His Phe Leu Trp Ile Ala Ala Val Leu Val Met   840
```

```
TTGTTGTTTTTTGTGGGATGGTGTCCTTTAAAACACTAAGGAAAAGGAAGAAGAAGCAGC
Phe Val Val Phe Cys Gly Met Val Ser Phe Lys Thr Leu Arg Lys Arg Lys Lys Lys Gln   900
```

FIG. 3A-2

```
CTGGCCCCTCTCATGAATGTGAAACCATCAAAAGGGAGAGAAAAGAGAGCAAACAGACCA    960
Pro Gly Pro Ser His Glu Cys Glu Thr Ile Lys Arg Glu Arg Lys Glu Ser Lys Gln Thr

ACGAAAGAGTACCATACCACGTACCTGAGAGATCTGATGAAGCCCAGTGTGTTAACATTT
Asn Glu Arg Val Pro Tyr His Val Pro Glu Arg Ser Asp Glu Ala Gln Cys Val Asn Ile    1020

TGAAGACAGCCTCAGGGGACAAAAATCAGTAGGAAAATGGTGGCTTGGCGTGCTGACAAT
Leu Lys Thr Ala Ser Gly Asp Lys Asn Gln  •                                          1080
```

FIG. 4A

FeCD28

```
ATGATCCTCAGGCTGCTTCTGGCTCTCAACTTCTTCCCCTCAATTCAAGTAACAGAAAAC
Met Ile Leu Arg Leu Leu Leu Ala Leu Asn Phe Phe Pro Ser Ile Gln Val Thr Glu Asn  60

AAGATTTTGGTGAAGCAGTTGCCCAGGCTTGTGGTGTACAACAATGAGGTCAACCTTAGC  120
Lys Ile Leu Val Lys Gln Leu Pro Arg Leu Val Val Tyr Asn Asn Glu Val Asn Leu Ser

TGCAAGTACACTCACAACTTCTTCTCAAAGGAGTTCCGGGCATCCCTTTATAAGGGAGTA  180
Cys Lys Tyr Thr His Asn Phe Phe Ser Lys Glu Phe Arg Ala Ser Leu Tyr Lys Gly Val

GATAGTGCTGTGGAAGTCTGCGTTGTGAATGGAAATTACTCCCATCAGCCTCAGTTCTAC  240
Asp Ser Ala Val Glu Val Cys Val Val Asn Gly Asn Tyr Ser His Gln Pro Gln Phe Tyr

TCAAGTACAGGATTCGACTGTGATGGGAAATTGGGCAATGAAACAGTGACATTCTACCTC  300
Ser Ser Thr Gly Phe Asp Cys Asp Gly Lys Leu Gly Asn Glu Thr Val Thr Phe Tyr Leu

CGAAATTTGTTTGTTAACCAAACGGATATTTACTTCTGCAAAATTGAAGTCATGTATCCA  360
Arg Asn Leu Phe Val Asn Gln Thr Asp Ile Tyr Phe Cys Lys Ile Glu Val Met Tyr Pro

CCTCCTTACATAGACAATGAGAAGAGCAATGGGACCATTATCCACGTGAAAGAGAAACAT  420
Pro Pro Tyr Ile Asp Asn Glu Lys Ser Asn Gly Thr Ile Ile His Val Lys Glu Lys His

CTTTGTCCAGCTCAGCTGTCTCCTGAATCTTCCAAGCCATTTTGGGCACTGGTGGTGGTT  480
Leu Cys Pro Ala Gln Leu Ser Pro Glu Ser Ser Lys Pro Phe Trp Ala Leu Val Val Val

GGTGGAATCCTAGGTTTCTACAGCTTGCTAGCAACAGTGGCTCTTGGTGCTTGCTGGATG  540
Gly Gly Ile Leu Gly Phe Tyr Ser Leu Leu Ala Thr Val Ala Leu Gly Ala Cys Trp Met

AAGACCAAGAGGAGTAGGATCCTTCAGAGTGACTATATGAACATGACCCCCCGGAGGCCA  600
Lys Thr Lys Arg Ser Arg Ile Leu Gln Ser Asp Tyr Met Asn Met Thr Pro Arg Arg Pro

GGGCCCACCCGAAGGCACTACCAACCTTACGCCCCAGCACGCGACTTTGCGGCATACCGT  660
Gly Pro Thr Arg Arg His Tyr Gln Pro Tyr Ala Pro Ala Arg Asp Phe Ala Ala Tyr Arg

TCCTGACATGGACCCCTATCCAGAAGCC  688
Ser
```

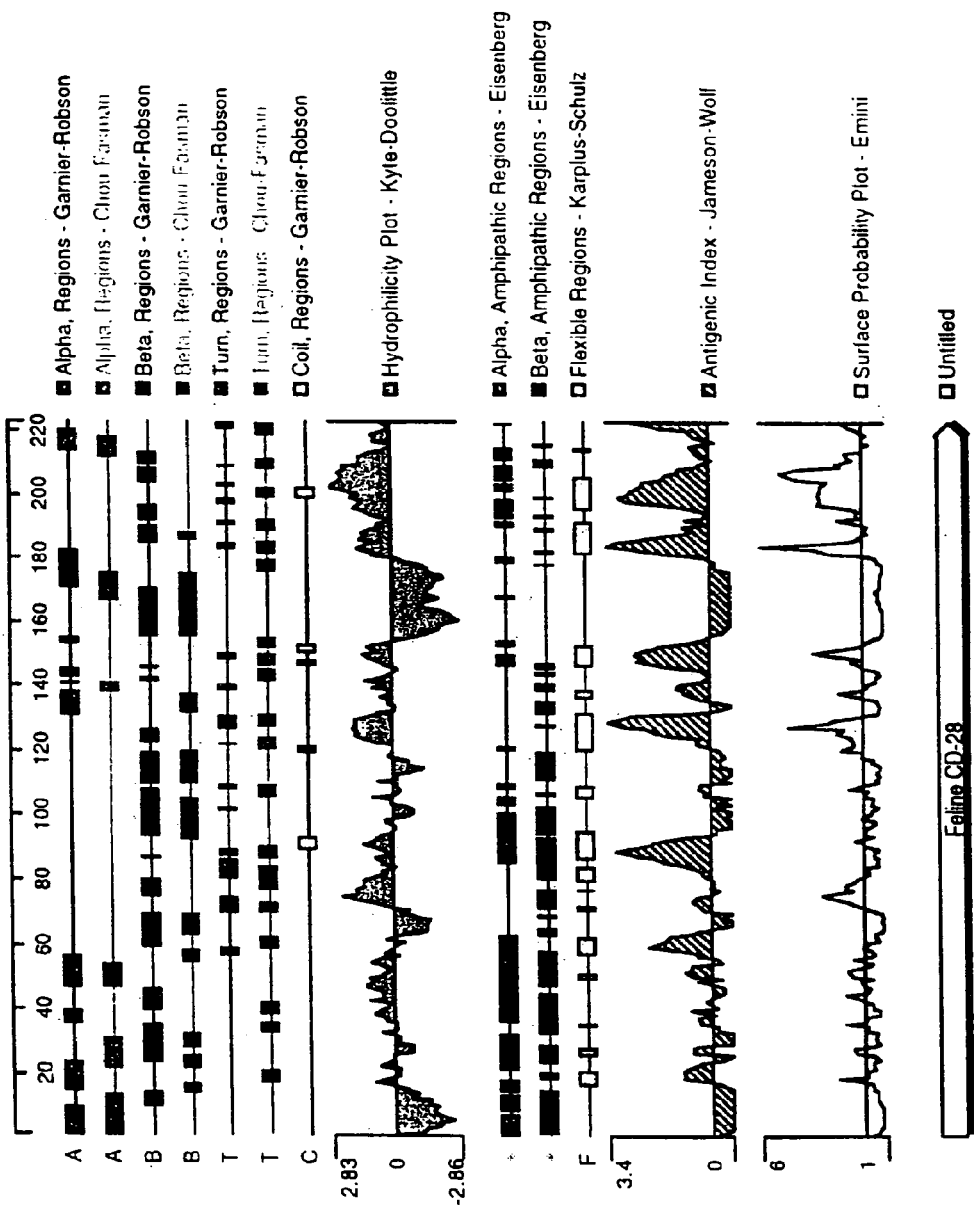
FIG. 4B  Hydrophobicity Plot: CD28

FIG. 5A

Fe CTLA4

```
AACCTGAACACTGCTCCCATAAAGCCATGGCTTGCTTTGGATTCCGGAGGCATGGGGCTC  60
                              Met Ala Cys Phe Gly Phe Arg Arg His Gly Ala

AGCTGGACCTGGCTTCTAGGACCTGGCCCTGCACTGCTCTGTTTTCTCTTCTCTTTATCC  120
Gln Leu Asp Leu Ala Ser Arg Thr Trp Pro Cys Thr Ala Leu Phe Ser Leu Leu Phe Ile

CCGTCTTCTCCAAAGGGATGCATGTGGCCCACCCTGCAGTGGTGCTGGCCAGCAGCCGAG  180
Pro Val Phe Ser Lys Gly Met His Val Ala His Pro Ala Val Val Leu Ala Ser Ser Arg

GTGTCGCCAGCTTCGTGTGTGAATATGGGTCTTCAGGCAATGCCGCCAAATTCCGAGTGA  240
Gly Val Ala Ser Phe Val Cys Glu Tyr Gly Ser Ser Gly Asn Ala Ala Lys Phe Arg Val

CTGTGCTGAGGCAAACTGGCAGCCAAATGACTGAAGTCTGTGCTGCGACATACACAGTGG  300
Thr Val Leu Arg Gln Thr Gly Ser Gln Met Thr Glu Val Cys Ala Ala Thr Tyr Thr Val

AGAATGAGTTGGCCTTCCTAAATGATTCCACCTGCACTGGCATCTCCAGCGGAAACAAAG  360
Glu Asn Glu Leu Ala Phe Leu Asn Asp Ser Thr Cys Thr Gly Ile Ser Ser Gly Asn Lys

TGAACCTCACCATCCAAGGGTTGAGGGCCATGGACACGGGACTCTACATCTGCAAGGTGG  420
Val Asn Leu Thr Ile Gln Gly Leu Arg Ala Met Asp Thr Gly Leu Tyr Ile Cys Lys Val

AGCTCATGTACCCACCACCCTACTATGCAGGCATGGGCAATGGAACCCAGATTTATGTCA  480
Glu Leu Met Tyr Pro Pro Pro Tyr Tyr Ala Gly Met Gly Asn Gly Thr Gln Ile Tyr Val

TCGATCCTGAACCTTGCCCAGATTCTGACTTCCTCCTCTGGATCCTCGCAGCAGTCAGTT  540
Ile Asp Pro Glu Pro Cys Pro Asp Ser Asp Phe Leu Leu Trp Ile Leu Ala Ala Val Ser

CAGGATTGTTTTTTTATAGCTTCCTTATCACAGCTGTTTCTTTGAGCAAAATGCTAAAGA  600
Ser Gly Leu Phe Phe Tyr Ser Phe Leu Ile Thr Ala Val Ser Leu Ser Lys Met Leu Lys

AAAGAAGCCCTCTTACTACAGGGGTCTATGTGAAAATGCCCCCAACAGAGCCAGAATGTG  660
Lys Arg Ser Pro Leu Thr Thr Gly Val Tyr Val Lys Met Pro Pro Thr Glu Pro Glu Cys

AAAAGCAATTTCAGCCTTATTTTATTCCCATCAATTGACACACCGTTATGAAGAAGGAAG  720
Glu Lys Gln Phe Gln Pro Tyr Phe Ile Pro Ile Asn  •

AACACTGTCCAATTTCTAAGAGCTGAGGC  749
```

FELINE CD86 POLYPEPTIDES AND NUCLEIC ACIDS

This application claims the benefit of and is a divisional application under 35 U.S.C. §120 of U.S. application Ser. No. 11/414,707, filed Apr. 27, 2006, now U.S Pat. No. 7,745,593, which is a divisional application under 35 U.S.C. §120 of U.S. application Ser. No. 09/303,510, filed Apr. 30, 1999, now U.S. Patent No. 7,078,512, which claims the benefit of U.S. Provisional Application No. 60/083,869, filed May 1, 1998 under 35 U.S.C. §119(e), the content of all of which are hereby incorporated into this application by reference. Throughout this application various publications are referenced in parentheses. Full citations for these publications may be found at the end of the specification immediately preceding the sequence listing section. The disclosures of these publications are in their entirety hereby incorporated by reference into this application to more fully describe the state of the art to which this invention pertains.

BACKGROUND

Currently there are no successful vaccines for the prevention of feline immunodeficiency disease and feline infectious peritonitis disease in cats. Current feline leukemia virus vaccines are available, but their level of efficacy remains questionable and in some cases may cause the disease. Therefore, there is a need in the art for agents and compositions that provide protection from these and other diseases where there is not yet an existing vaccine or that improve the efficacy of existing and commonly used vaccines. In addition, vaccination of kittens is difficult due to inability to overcome maternal antibodies in kittens. Safe and effective agents to help overcome these barriers are also needed.

The stimulation of T-cell activation and proliferation in response to disease in the host is believed to be dependent on two interactions: the recognition of the T-cell receptor (TCR) with immunogenic peptides in the context of the MHC class I molecules and the secondary interaction of accessory ligands, such as CD80 and CD86, with their coreceptors, CD-28 and/or CTLA-4 on the T-cell. The successful interaction of these two pathways leads to activation and proliferation of both CD4+ and CD8+ T-cells and the increased production of Th1 and Th2 type immune regulating cytokines In the absence of adequate co-stimulation of T-cells, an anergic state may develop, whereby T cells fail to proliferate and secrete cytokines Over the years, two molecules have emerged as key regulators of T cell responses, CD28 and its ligands, CD80 and CD86, it enhances T-cell proliferation and cytokine synthesis, preventing T-cell death. CTLA-4 (also called CD152), a CD-28 homologue, also plays an important role in co-stimulation. Although, not completely understood, it appears to inhibit T-cell costimulatory responses. The interaction and interplay among CD28, CTLA-4 and their ligands CD80 and CD86 in co-stimulatory processes is key to the overall induction and suppression of immune responses to disease in the host. By manipulating the expression of these 4 costimulatory molecules, it may be possible to regulate T-cell responses, through augmentation, suppression or redirection, to raise a desired immune response towards a particular pathogen or disease condition. In particular, they may be useful for vaccination against infectious diseases, treatment of infectious diseases, and treatment of neoplastic, degenerative, autoimmune, and immunodeficiency conditions.

T-lymphocytes of the mammalian immune system display both control and effector functions. T cell progenitors arise in the bone marrow from stem cells and migrate to the thymus. In the thymus, maturation and selection take place to produce a naive population of immune cells that is able to recognize antigen in the context of major histocompatibility complex (MHC) presentation but is not autoreactive. Following thymic maturation, each T cell possesses a clonally distributed T cell receptor (TCR) which determines its antigen specificity. Further, CD4+ and CD8+ T-cells, the two major subsets found in most adult mammals, possess TCR composed of $\alpha$ and $\beta$ subunits (Allison and Lanier, 1987).

Protein and gene organization of the TCR protein is similar to that observed with immunoglobulin (Ig) molecules, and it shares many properties similar to membrane bound Ig on B cells (Allison and Lanier, 1987). Like the Ig molecule, the TCR must potentially recognize a vast number of potential antigen sequences. For this reason, TCR gene organization and rearrangement is similar in complexity with that observed in B cells (Davis and Bjorkman, 1988). As with antibody molecules produced by B cells, generation of idiotypic diversity in T-cells involves multiple copies of variable (V) genes in the germ line, random rearrangements of $\alpha$ and $\beta$ subunits, and variability generated by junctional and insertional events (Davis and Bjorkman, 1988). Unlike B cells however, T-cells do not appear to generate diversity through somatic mutation, though the potential repertoire of the TCR appears to be as great as that of the Ig molecule (Lechler et al., 1990).

The TCR, though responsible for antigen recognition, does not have signal delivery capabilities (Allison and Lanier, 1987). Conformational changes in the TCR, following binding to antigen presented in the context of MHC on the antigen presenting cell (APC), result in signal delivery through a noncovalently associated complex of surface molecules including CD3 and the $\zeta$ chains (Clevers et al., 1988). TCR binding results in the phosphorylation of the CD3 complex, which indirectly leads to a $Ca^+$ influx into the cell, initiating IL-2 and IL-2R production (Weiss and Littman, 1994). This cascade is considered an initial event in T cell activation.

The TCR recognizes antigen only when it is presented in association with the MHC. There are two subsets of MHC proteins associated with antigen presentation to the T cell. MHC class I is found on almost all nucleated cells within the body and functions to surface express endogenously produced peptides (Matasumura et al., 1992). Peptide expressed in the context of MHC class I is recognized by T-cells expressing CD8 in association with the TCR (Littman, 1987). CD8+ T-cells function in immuno-surveillance for removal of virally infected cells and malignancies. Recognition of non-self molecules by the CD8+ T cell (peptides or altered self peptides that might indicate a malignancy) result in the cytotoxic T-lymphocyte (CTL) mediated destruction of the cell (Berke, 1994).

MHC class II molecules, the second major histocompatibility subset, are normally found only on professional antigen presenting cells including B cells, macrophages/monocytes and dendritic cells, though induction on some other cell populations in response to specific stimuli is possible (Germain, 1993). The MHC class II molecule is responsible for the presentation of exogenous antigen to the CD4+ T cell. Antigen that is phagocytosed, endocytosed or surface Ig bound and absorbed by antigen presenting cells is endogenously processed and bound to MHC class II (Unanue, 1987). The molecule is then surface expressed and available for recognition by CD4 expressing $\alpha\beta$ T-cells (Littman, 1987). Antigen recognition by CD4+ T-cells results in the production of cytokines and growth factors necessary for the initiation and promulgation of many facets of an active immune response (Mosmann and Coffman, 1987).

CD4 and CD8 differentiate the αβ T cell subsets and define the functional properties of each group. The presentation of CD4 or CD8 on a T cell is mutually exclusive (Littman, 1987). Thus, following thymic selection and maturation, αβ T-cells present only CD4 or CD8. The molecules act to stabilize the interaction between the TCR and antigen bound MHC and determine whether the T cell recognizes antigen presented in the context of MHC class I or class II (Littman, 1987). The binding domain of the CD4 or CD8 molecule recognizes respective non-polymorphic regions of the class I or class II molecule (Clayberger et al., 1994). Binding of CD4 or CD8 to these specific regions acts to stabilize the TCR/antigen bound MHC interaction, for the initiation of T cell activation (Littman, 1987). Thus, CD4+ T-cells only functionally interact with APC expressing antigen in the context of class II and initiating a T helper response, while CD8+ T-cells only recognize antigen presented in the context of class I, and upon binding initiate a cytotoxic response (Germain, 1993). The two distinct phenotypes of helper T-cells and CTL can be differentiated by the surface expression of either CD4 or CD8.

The majority of T-lymphocytes bearing CD4 are generally considered to be helper cells though there is a proposed CD4+ CTL subset (Yasukawa, et al., 1989). CD4+ helper T-cells are major regulators of the immune response through the production of a battery of stimulatory and suppressive cytokines (Mosmann and Coffman, 1987). The factors produced by these cells are important mediators in the initiation of both a humoral or antibody mediated response and a cellular or delayed type hypersensitivity (DTH) response (Mosmann and Coffman, 1987). For CD4+ T-cells to become activated and produce soluble growth factors, a complex cascade of events must occur. Antigen is detected and endocytosed by a professional APC, normally a macrophage (Unanue, 1984). The APC denatures the protein and breaks it down into smaller fragments, peptide fragments of between 15-18 amino acid residues are then bound with the MHC in the endoplasmic reticulum and subsequently transferred to the surface for expression (Rotzschke et al., 1994). Surface expressed antigen is thus visible to T-lymphocytes and can be recognized by the T cell subsets with the proper TCR idiotype and expressing CD4 (Germain, 1993). When the T cell recognizes the proper antigen, and the proper accessory signals are delivered, differentiation of the naive lymphocyte occurs and clonal expansion can proceed. As yet undetermined stimuli result in the preferential development of a type 1 (cellular) response versus a type 2 (humoral) response (Mosmann and Coffman, 1989).

T cell help is required for much of the activity of both a humoral and a cellular response. A T cell dependent B cell response, which is required for antibody to be made to most antigens, requires T cell help for proper B cell maturation to take place (Chesnut et al., 1986). Once the surface expressed Ig on the B cell has bound antigen, internalization, processing and MHC class II surface expression of these antigens occurs (Germain, 1993). Direct cell to cell contact between the CD4+ T cell with the proper TCR idiotype and the B cell, promotes the activation and proliferation of the T cell (Chesnut et al., 1986). The activated helper T cell may be capable of promoting a type II response by secreting factors necessary for B cell growth and differentiation (Mosmann and Coffman, 1989). These factors include, IL-4, IL-5 and IL-13 which can induce B cell activation and proliferation, and are important in isotypic switches for the Ig molecule, while IL-10 acts to prevent the initiation of a type I response which would in turn down-regulate humoral activity (Mosmann and Coffman, 1989).

Cellular responses (type I) do not mature in the same fashion as humoral responses (type II) (Sher et al., 1992). Upon T cell activation and maturation to a type 1 response, factors are produced by the T cell that favor cellular immunity. IL-2 is a T cell growth factor that also promotes CTL responses, while IFNγ acts to activate macrophages, CTL and neutrophils (Wang et al., 1993).

T helper cells are thus able to mediate two largely mutually exclusive responses. The cytokine secretion pattern that leads to the initiation of a humoral response contains factors that are suppressive of a cellular response and vice versa (Mosmann and Coffman, 1989). It is unclear what determines whether a T cell will produce a type 1 pattern (IL-2, IFNγ and lymphotoxin) or a type 2 pattern (IL-4, 5, 6, 10, and 13) although it is proposed that the type of APC that presents the antigen or soluble factors produced by the APC may influence the type of cytokine pattern that develops (Mosmann and Coffman, 1989). In addition to the type 1 and type 2 helper cells, T helper type 0 subsets exist in which secretion patterns are intermediate between type 1 and type 2 (Gajewski et al., 1989). While T helper subsets have mainly been demonstrated in in vitro experimentation, and may be artifacts of culture, they are important models for the role of the T helper cell in modulating the development of specific responses in an in vivo environment.

In addition to the CD4+ T helper lymphocyte subset, a second αβ T cell population consists of CD8 bearing cytotoxic lymphocytes. The CD8+ CTL appear to be a major component of the immune surveillance system whose primary function is to destroy virally and intracellular bacterially infected cells as well as malignancies (Berke, 1994). These cells are also able to produce cytokines, but generally only those associated with inducing cellular responses (IL-2, IFNγ and TNF) (Fong and Mosmann, 1990). The TCR of these cells, in association with CD8, recognize antigen presented in the context of MHC class I (Littman, 1987). In general, all nucleated cells have surface expression of class I presenting endogenously synthesized peptides (Matasumara, 1992). Specific, immuno-privileged sites, including the brain and the testes, have low level expression of the protein, though it is inducible in these areas with interferon exposure (Moffett and Paden, 1994).

Proteins produced in the endoplasmic reticulum through the normal metabolism of the cell are denatured, partially degraded and bound to MHC class I for surface expression (Engelhard, 1994). The polypeptides are proteolytically linearized and bound in 9-12 amino acid epitopes to class I which is then expressed on the surface of the cell (Engelhard, 1994). Theoretically all endogenously produced peptides are surface expressed in this fashion, and thymic selection ideally results in the elimination of all autoreactive T-cells, immune-surveillance can detect the presence of virally infected or transformed cells (Berke, 1993). The recognition of foreign peptides expressed by class I is facilitated by the antigen specific T cell receptors on CD8+ CTL (Lechler et al., 1990). Contact between the effector cell and the target is required for activation to proceed (Berke, 1994). When an antigen that is seen as foreign is detected by the TCR, the interaction between the molecules is stabilized by CD8 binding to the class I on the infected cell (Littman, 1987). Once recognition occurs and the T cell becomes activated, a conjugate forms between the target cell and the effector T cell, and the effector cell is dispatched (Taylor and Cohen, 1992). Thus, in this fashion, if self proteins are altered or if the cellular machinery is taken over by a pathogen, peptides will be available for recognition by immune surveillance and this arm of the immune system can eliminate the diseased cell (Berke, 1994).

Cellular cytotoxicity appears to result from one of two major pathways. Either the cell is induced to undergo apoptotic death or it is lysed through the release of cytotoxic granules by the CTL (Berke, 1993). Apoptosis is induced in target cells through the release of factors by the CTL which induce gene expression that result in cell death (Russel, 1983). An advantage of this mechanism is that cell lysis does not occur and the potential for the release of the potentially infectious contents of the cell is reduced (Nagata and Golstein, 1995). Cell lysis however may be the more common mechanism through which target elimination takes place. Perforin, which acts to perforate target cell membranes, is a major constituent of CTL cytotoxic granules (Liu et al., 1995). Although there are other cell types involved in this form of immuno-surveillance, CTL appear to be a major component of anti-viral and anti-tumor immunity and, against specific pathogens, are considered indispensable for protection (Kupfer and Singer, 1989).

Initially cell surface proteins were used to differentiate specific cell populations. More recently functional aspects of many of these molecules have been derived, and while they are still important in delineating cell populations, their critical role in the function of many cells is becoming more evident.

A variety of accessory and adhesion molecules that play a role in the development of a productive immune response are expressed on T-cells and antigen presenting cells (van Seventer et al., 1991). Adhesion molecules are expressed at some level on most cells of the immune system. They are important in retaining cells within an area and in the initiation and maintenance of cell to cell contact (Mescher, 1992).

CD-2/LFA 3 (CD58) and LFA-1/ICAM-1 are two adhesion molecule complexes involved in the stabilization of T cell/APC interactions and the enhancement of activity (Springer et al., 1987). CD2 is one of the first markers expressed on pre-T-cells and persists throughout the life of the cell, while LFA-1 is expressed later on T-cells and is up-regulated in memory cells or by induction (Springer et al., 1987).

Accessory molecule complexes also demonstrate adhesive properties, but their main function is probably the delivery of an intracellular signal upon ligand binding (Anderson et al., 1988). Upon establishment of an interaction between the receptor and its ligand, a conformational change in the molecules structure takes place that results in the delivery of a signal to the cytoplasm of one or both cells (Hutchcroft and Bierer, 1994). Signals delivered by these molecules play a variety of roles in promoting T cell development, but in the absence of signals mediated by these molecules, T-cells may become anergic (Leung and Linsley, 1994).

The CD28/CD80 interaction is a major component of a productive T cell mediated immune response (Linsley et al., 1993a). The interaction of the CD28 accessory molecule with its ligand CD80 is required for full activation and proliferation of naive T-cells (Linsley et al., 1991a). The interaction also appears to play a critical role in activated and memory CD4$^+$ T cell proliferation and prevention of apoptotic cell death (Linsley et al., 1991a). The discovery of the interaction and elucidation of its mechanisms has provided a critical link in the understanding T cell mediated immunity.

SUMMARY OF THE INVENTION

The present invention provides isolated and purified DNA encoding feline CD80 (B7-1) ligand, feline CD86 (B7-2) ligand, feline CD28 receptor, or feline CTLA-4 (CD152) receptor, as well as vectors comprising nucleic acid encoding feline CD80, feline CD86, feline CD28, or feline CTLA-4. The present invention provides a host cells transformed with CD80-encoding vectors, CD86-encoding vectors, CD28-encoding vectors, or CTLA-4-encoding vectors. The invention provides polypeptides encoded by the nucleic acid of feline CD80, feline CD86, feline CD28, or feline CTLA-4.

The present invention provides a vaccine comprising an effective amount of polypeptides encoded by the nucleic acid of feline CD80, feline CD86, feline CD28, or feline CTLA-4. The present invention also provides vaccines which further comprise immunogens derived from pathogens. The invention provides for vaccines capable of enhancing an immune response. The invention also provides for vaccines capable of suppressing and immune response.

BRIEF DESCRIPTION OF THE FIGURES

FIG. 1A: DNA and amino acid sequence of feline CD80 (B7-1)(TAMU). (SEQ ID NOS: 1 and 2)

FIG. 2A: DNA and amino acid sequence of feline CD80 (B7-1) (SYNTRO). (SEQ ID NOS: 3 and 4)

FIG. 3A: DNA and amino acid sequence of feline CD86 (B7-2). (SEQ ID NOS: 5 and 6)

FIG. 4A: DNA and amino acid sequence of feline CD28. (SEQ ID NOS: 7 and 8)

FIG. 4B: Hydrophobicity plot of amino acid sequence of feline CD28.

FIG. 5A: DNA and amino acid sequence of feline CTLA-4 (CD152). (SEQ ID NOS: 9 and 10)

DETAILED DESCRIPTION OF THE INVENTION

The present invention involves an isolated nucleic acid encoding a feline CD80 ligand or a feline soluble CD80 ligand. The present invention also involves an isolated nucleic acid encoding a feline CD86 ligand or a feline soluble CD86 ligand. The present invention involves an isolated nucleic acid encoding a feline CD28 receptor or a feline soluble CD28 receptor. The present invention involves an isolated nucleic acid encoding a feline CTLA-4 receptor or a feline soluble CTLA-4 receptor.

Figure 1B:
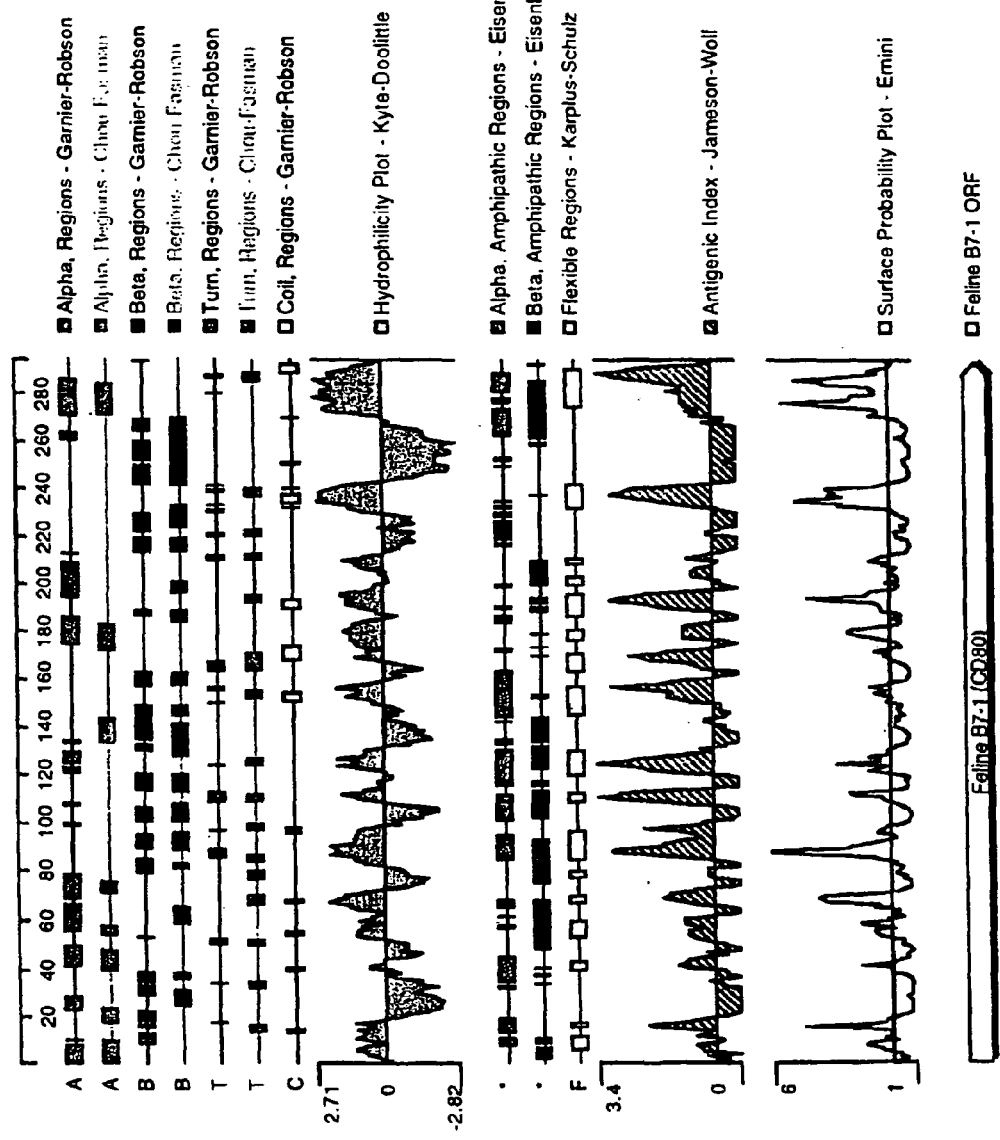
FIG. 1B: Hydrophobicity plot of amino acid sequence of feline CD80 (B7-1) (TAMU).

In one embodiment the present invention provides nucleic acid encoding feline CD80 ligand which has the sequence shown in FIG. 1A beginning with methionine and ending with threonine (SEQ ID NO: 1). In another embodiment the present invention provides nucleic acid encoding the feline CD86 ligand which has the sequence shown in FIG. 3A beginning with methionine and ending with glutamine (SEQ ID NO: 5). In one embodiment the present invention provides nucleic acid encoding a feline CD28 receptor shown in FIG. 4A which has the sequence beginning with methionine and ending with serine (SEQ ID NO: 7). In one embodiment the present invention provides nucleic acid encoding a feline CTLA-4 receptor which has the sequence shown in FIG. 5A beginning with methionine and ending with asparagines (SEQ ID NO: 9).

In an embodiment of the above-described invention, the nucleic acid is DNA or RNA. In another embodiment the DNA is cDNA or genomic DNA.

The invention provides an oligonucleotide of at least 12 nucleotides which has a sequence complementary to a sequence uniquely present in the nucleic acid encoding CD28, CD80, CD86, or CTLA-4 described above. Another embodiment of the invention provides an oligonucleotide which is at least 15 or 16 nucleotides in length which has a sequence complementary to a sequence uniquely present in the nucleic acid encoding CD28, CD80, CD86, or CTLA-4 described above.

Another embodiment of the above-described invention provides an oligonucleotide which is detectably labeled. In one embodiment the detectable label comprises a radioisotope, a fluorophor, or biotin. In another embodiment the oligonucleotide is selectively methylated.

The invention provides a vector comprising nucleic acid encoding a feline CD80 ligand or a feline soluble CD80 ligand. Another embodiment of the invention provides a plasmid vector designated PSI-B7-1/871-35 (ATCC Accession No. 209817). This plasmid was deposited on Apr. 29, 1998 with the American Type Culture Collection (ATCC), 10801 University Boulevard, Manassas, Va. 20108-0971, U.S.A. under the provisions of the Budapest Treaty for the International Recognition of the Deposit of Microorganisms for the Purposes of Patent Procedure.

The invention provides a vector comprising nucleic acid encoding a feline CD86 ligand or a feline soluble CD86 ligand. The invention provides a plasmid vector designated B7-2#19-2/011298 (ATCC Accession No. 209821). This plasmid was deposited on Apr. 29, 1998 with the American Type Culture Collection (ATCC), 10801 University Boulevard, Manassas, Va. 20108-0971, U.S.A. under the provisions of the Budapest Treaty for the International Recognition of the Deposit of Microorganisms for the Purposes of Patent Procedure.

The present invention provides a vector comprising the nucleic acid encoding a feline CD28 receptor or a feline soluble CD28 receptor. The present invention provides a plasmid vector designated PSI-CD28 #7/100296 (ATCC Accession No. 209819). This plasmid was deposited on Apr. 29, 1998 with the American Type Culture Collection (ATCC), 10801 University Boulevard, Manassas, Va. 20108-0971, U.S.A. under the provisions of the Budapest Treaty for the International Recognition of the Deposit of Microorganisms for the Purposes of Patent Procedure.

The present invention provides a vector comprising nucleic acid encoding a feline CTLA-4 receptor or a feline soluble CTLA-4 receptor. The present invention provides a plasmid vector designated CTLA-4#1/091997 (ATCC Accession No. 209820). This plasmid was deposited on Apr. 29, 1998 with the American Type Culture Collection (ATCC), 10801 University Boulevard, Manassas, Va. 20108-0971, U.S.A. under the provisions of the Budapest Treaty for the International Recognition of the Deposit of Microorganisms for the Purposes of Patent Procedure.

The invention provides a vector described above which further comprises a promoter operably linked to the nucleic acid. In another embodiment the invention provides a host cell which comprises any of the above-described vectors. In one embodiment the host cell comprising one of the above-described vectors is a eukaryotic or a prokaryotic cell. In another embodiment the host cell is either E. coli, yeast, COS cells, PC12 cells, CHO cells, or GH4C1 cells.

The invention provides a polypeptide encoded by the nucleic acid encoding a feline CD80 ligand or a feline soluble CD80 ligand. An embodiment of the invention provides a polypeptide encoded by nucleic acid encoding a feline CD86 ligand or a feline soluble CD86 ligand. Another embodiment of the invention provides a polypeptide encoded by nucleic acid encoding a feline CD28 receptor or a feline soluble CD28 receptor. The present invention provides a polypeptide encoded by nucleic acid encoding a feline CTLA-4 receptor or a feline soluble CTLA-4 receptor.

In another embodiment the invention provides method of producing the above-described polypeptides by culturing a host cell which expresses the polypeptides and recovering the polypeptides so produced.

The present invention provides a vaccine comprising an effective amount of the above-described polypeptides and a suitable carrier. In another embodiment the invention provides a vaccine wherein the effective amount of the above-described polypeptide and suitable carrier is an amount from about 0.01 mg to about 100 mg per dose. In another embodiment the invention provides a vaccine wherein the effective amount of the above-described polypeptide and suitable carrier is an amount from about 0.25 mg/kg weight body of a feline/day to about 25 mg/kb weight of a feline/day.

The present invention further provides an above-described vaccine which further comprises an immunogen derived from a pathogen. In another embodiment the immunogen within the vaccine is derived from a feline pathogen, a rabies virus, chlamydia, Toxoplasmosis gondii, Dirofilaria immitis, a flea, or a bacterial pathogen. In another embodiment, the invention provides a vaccine wherein the feline pathogen is feline immunodeficiency virus (FIV), feline leukemia virus (FeLV), feline infectious peritonitis virus (FIP), feline panleukopenia virus, feline calicivirus, feline reovirus type 3, feline rotavirus, feline coronavirus, feline syncytial virus, feline sarcoma virus, feline herpesvirus, feline Borna disease virus, or a feline parasite.

The invention also provides a method of inducing immunity in a feline which comprises administering to the feline a dose of a vaccine containing any of the above-described immunogens. The invention also provides a method of enhancing an immune response in a feline which comprises an effective dose of a polypeptide, an immunogen, and a suitable carrier. The invention provides a method of administering the above-described vaccine subcutaneously, intramuscularly, systemically, topically, or orally.

A further embodiment of the invention provides a method for suppressing an immune response in a feline which comprises administering to the feline an effective immune response suppressing amount of a polypeptide encoding feline CTLA-4 nucleic acid. In another embodiment the invention provides a method for suppressing an immune response in a feline which comprises administering to the feline an effective immune response suppressing amount of a soluble polypeptide encoding feline CD80, feline CD86, or feline CD28.

In another embodiment the present invention provides a method for suppressing an immune response in a feline by administering from about 0.25 mg/kg body weight/day to about 25 mg/kb body weight/day of a polypeptide encoding feline CTLA-4 nucleic acid. In another embodiment the present invention provides a method for suppressing an immune response in a feline by administering from about 0.25 mg/kg body weight/day to about 25 mg/kb body weight/day of a polypeptide encoding feline CD80, feline CD86, or feline CD28.

The present invention also provides a method of suppressing an immune response in a feline suffering from an autoimmune disease or is the recipient of a tissue or organ transplant by administering to the feline an effective immune response suppressing amount of a polypeptide encoding feline CTLA-4 nucleic acid.

The present invention also provides a method of suppressing an immune response in a feline suffering from an autoimmune disease or is the recipient of a tissue or organ transplant by administering to the feline an effective immune response suppressing amount of a polypeptide encoding feline CD80, feline CD86, or feline CD28.

The invention provides isolated and purified feline CD80 (B7-1) cDNA of approximately 941 nucleotides. The invention also provides isolated and purified feline CD80 polypeptide of approximately 292 amino acids, the native membrane bound or mature form which has a molecular mass of about 33,485 kDa, an isoelectric point of about 9.1, a net charge at pH 7.0 of 10. The coexpression of CD80, with the costimulatory molecule CD28, and a tumor antigen or an antigen from a pathogenic organism, has the ability to activate or enhance activation of T-lymphocytes, inducing the production of immune stimulating cytokines and to regulate the growth of other cell types. The coexpression of CD80, with costimulatory molecule CTLA-4, has the ability to regulate activation of T-lymphocytes.

The invention provides isolated and purified feline CD86 (B7-2) cDNA of approximately 1176 nucleotides. The invention also provides isolated and purified feline CD86 polypeptide of approximately 320 amino acids, the native membrane bound or mature form of which has a molecular mass of approximately 36,394 kDa, an isoelectric point of about 9.19, a net charge at pH 7.0 of 11.27. The coexpression of CD86, with costimulatory molecules CD28 and a tumor antigen or an antigen from a pathogenic organism, has the ability to activate or enhance activation of T-lymphocytes, inducing the production of immune stimulating cytokines and to regulate the growth of other cell types. The coexpression of CD86, with costimulatory molecule CTLA-4, has the ability to regulate activation of T-lymphocytes.

Feline CD80 or CD86 according to the present invention are obtained from native or recombinant sources. Feline CD80 or CD86 according to the present invention comprises the native and membrane bound form or a secreted form lacking the transmembrane domain.

The invention provides isolated and purified feline CD28 cDNA of approximately 689 nucleotides. The invention also provides isolated and purified feline CD28 polypeptide of approximately 221 amino acids, the native membrane bound or mature form which has a molecular mass of about 25,319 kDa, an isoelectric point of about 9.17, a net charge at pH 7.0 of 9.58.

The invention provides isolated and purified feline CTLA-4 cDNA of approximately 749 nucleotides. The invention also provides isolated and purified feline CTLA-4 polypeptide of approximately 223 amino acids, the native membrane bound or mature form which has a molecular mass of about 24,381 kDa, an isoelectric point of about 6.34, a net charge at pH 7.0 of –0.99.

In another aspect, the invention provides a method of enhancing an immune response in a feline to an immunogen, which is achieved by administering the immunogen before, after or substantially simultaneously with the feline CD80 or feline CD86 with or without feline CD28 or feline CTLA-4 in an amount effective to enhance the immune response.

In another aspect, the invention provides a method of suppressing an immune response in a feline to an immunogen, which is achieved by administering the immunogen before, after or substantially simultaneously with the feline CD80 or feline CD86 with or without feline CD28 or feline CTLA-4 or with antisense RNA or DNA, in part or whole, encoding feline CD80 or feline CD86 or feline CD28 or feline CTLA-4, in an amount effective to suppress the immune response.

In another aspect, the invention provides a vaccine for inducing an immune response in felines to an immunogen, comprising the immunogen and an effective amount of feline CD80 for immune response enhancement. The immunogen is derived, for example, from feline pathogens such as feline immunodeficiency virus, feline leukemia virus, feline parvovirus, feline coronavirus, feline leptovirus, and the like.

In another aspect, the invention provides a vaccine for inducing an immune response in felines to an immunogen, which is achieved by administering DNA or RNA of an immunogen and DNA or RNA of feline CD80, CD86, CD28 accessory molecules, in any combination, encoding the proteins or fragments of proteins in an amount effective to modulate the immune response.

The feline CD80 protein has an amino acid sequence which is 59% and 46% identical with the human and mouse proteins, respectively. The feline CD86 protein has an amino acid sequence which is 68% and 64% identical with the human and rabbit proteins, respectively. The feline CD28 protein has an amino acid sequence which is 82% and 74% identical with the human and mouse proteins, respectively. The feline CTLA-4 protein has an amino acid sequence which is 88% and 78% identical with the human and mouse proteins, respectively. The human or mouse CD80 or CD86 proteins cannot functionally replace the feline CD80 or CD86 proteins. Therefore, the feline CD80, feline CD86, feline CD28 and feline CTLA-4 are novel reagents required for the regulation of immunity in felines.

The present invention encompasses T-cell regulatory accessory molecules, CD80 (B7-1) or CD86 (B7-2) or CD28 or CTLA-4 (CD152) from feline species. The invention provides isolated and purified nucleic acids encoding, in part or whole, feline CD80 or feline CD86 or feline CD28 or feline CTLA-4, as well as CD80, CD86, CD28 or CTLA-4 polypeptides purified from either native or recombinant sources. Feline CD80, CD86, CD28 or CTLA-4 produced according to the present invention is used to enhance the efficacy of feline vaccines against tumors and pathogenic organisms and as a therapeutic to treat viral and bacterial diseases in cats. Feline CD80, CD86, CD28 or CTLA-4 produced according to the present invention is also used to alleviate disease due to overactive, hyperactive or misdirected immune responses.

Nucleic Acids, Vectors, Transformants

The sequences of the cDNA encoding feline CD80 (SEQ ID NO: 1), feline CD86 (SEQ ID NO: 5), feline CD28 (SEQ ID NO: 7), or feline CTLA-4 (SEQ ID NO: 9), are shown in FIGS. 1 to 5, and the predicted amino acid sequences of feline CD80 (SEQ ID NO: 2), feline CD86 (SEQ ID NO: 6), feline CD28 (SEQ ID NO: 8), or feline CTLA-4 (SEQ ID NO: 10), are shown in FIGS. 1 to 5. The designation of these feline polypeptides as CD80, CD86, CD28 or CTLA-4 is based on partial amino acid sequence homology to human or mouse or rabbit homologues of these polypeptides, and the ability of the CD80 or CD86 polypeptides to bind to feline CD28 receptor (see below) or to CTLA-4 and to activate or stimulate or otherwise regulate activation of T-lymphocytes. Furthermore, without wishing to be bound by theory, it is predicted that feline CD80 or feline CD86 polypeptides also exhibit one or more of the following bioactivities: activation of NK (natural killer) cells, stimulation of B-cell maturation, activation of MHC restricted cytotoxic T-lymphocytes, proliferation of mast cells, interaction with cytokine receptors and induction of immune-regulating cytokines.

Because of the degeneracy of the genetic code (i.e., multiple codons encode certain amino acids), DNA sequences other than that shown in FIGS. 1 to 5 can also encode the feline CD80, CD86, CD28 or CTLA-4 amino acid sequences shown in FIGS. 1 to 5. Such other DNAs include those containing "sequence-conservative" variations in which a change in one or more nucleotides in a given codon results in no alteration in the amino acid encoded at that position. Furthermore, a given amino acid residue in a polypeptide can often be changed without altering the overall conformation and function of the native polypeptide. Such "function-conservative" variants include, but are not limited to, replacement of an amino acid with one having similar physico-chemical properties, such as, for example, acidic, basic, hydrophobic, hydrophilic, aromatic and the like (e.g., replacement of lysine with arginine, aspartate with glutamate, or glycine with alanine). In addition, amino acid sequences are added or deleted without destroying the bioactivity of the molecule. For example, additional amino acid sequences are added at either amino- or carboxy-terminal ends to serve as purification tags, such as histidine tags, (i.e., to allow one-step purification of the protein, after which they are chemically or enzymatically removed). Alternatively, the additional sequences confer an additional cell-surface binding site or otherwise alter the target cell specificity of feline CD80, CD86, CD28 or CTLA-4, such as with the addition of an antigen binding site for antibodies.

The feline CD80 or feline CD86 or feline CD28 or feline CTLA-4 cDNAs within the scope of the present invention are those of FIG. 1 to 5, sequence-conservative variant DNAs, DNA sequences encoding function-conservative variant polypeptides, and combinations thereof. The invention encompasses fragments of feline CD80, CD86, CD28 or CTLA-4 that exhibit a useful degree of bioactivity, either alone or in combination with other sequences or components. As explained below, it is well within the ordinary skill in the art to predictively manipulate the sequence of CD80, CD86, CD28 or CTLA-4 and establish whether a given feline CD80, CD86, CD28 or CTLA-4 variant possesses an appropriate stability and bioactivity for a given application, or variations that affect the binding activities of these molecules resulting in increased effectiveness. Feline CD80 and CD86 will each bind to coreceptor CD28 or to coreceptor CTLA-4. This can be achieved by expressing and purifying the variant CD80, CD86, CD28 or CTLA-4 polypeptide in a recombinant system and assaying its T-cell stimulatory activity and/or growth-promoting activity in cell culture and in animals, followed by testing in the application. The variant CD80 is tested for bioactivity by functional binding to the CD28 or CTLA-4 receptors. The variant CD86 is tested for bioactivity by functional binding to the CD28 or CTLA-4 receptors. In a similar manner, variant CD28 or variant CTLA-4 is tested for bioactivity.

The present invention also encompasses feline CD80, CD86, CD28 or CTLA-4 DNAs (and polypeptides) derived from other feline species, including without limitation domestic cats, lions, tigers, cheetahs, bobcats and the like. Feline CD80, CD86, CD28 or CTLA-4 homologues of the sequence shown in FIG. 1 to 5 are easily identified by screening cDNA or genomic libraries to identify clones that hybridize to probes comprising all or part of the sequence of FIG. 1 to 5. Alternatively, expression libraries are screened using antibodies that recognize feline CD80, CD86, CD28 or CTLA-4. Without wishing to be bound by theory, it is anticipated that CD80 or CD86 genes from other feline species will share at least about 70% homology with the feline CD80, CD86, CD28 or CTLA-4 genes. Also within the scope of the invention are DNAs that encode homologues of CD80, CD86, CD28 or CTLA-4, defined as DNA encoding polypeptides that share at least about 25% amino acid identity with feline CD80, CD86, CD28 or CTLA-4.

Generally, nucleic acid manipulations according to the present invention use methods that are well known in the art, such as those as disclosed in, for example, *Molecular Cloning, A Laboratory Manual* (2nd Ed., Sambrook, Fritsch and Maniatis, Cold Spring Harbor), or *Current Protocols in Molecular Biology* (Eds. Aufubel, Brent, Kingston, More, Feidman, Smith and Stuhl, Greene Publ. Assoc., Wiley-Interscience, NY, N.Y., 1992).

The present invention encompasses cDNA and RNA sequences and sense and antisense. The invention also encompasses genomic feline CD80, CD86, CD28 or CTLA-4 DNA sequences and flanking sequences, including, but not limited to, regulatory sequences. Nucleic acid sequences encoding feline CD80, CD86, CD28 or CTLA-4 polypeptide(s) are also associated with heterologous sequences, including promoters, enhancers, response elements, signal sequences, polyadenylation sequences, introns, 5'- and 3'-noncoding regions, and the like. Transcriptional regulatory elements that are operably linked to feline CD80, CD86, CD28 or CTLA-4 cDNA sequence(s) include without limitation those that have the ability to direct the expression of genes derived from prokaryotic cells, eukaryotic cells, viruses of prokaryotic cells, viruses of eukaryotic cells, and any combination thereof. Other useful heterologous regulatory sequences are known to those skilled in the art.

The nucleic acids of the present invention are modified by methods known to those skilled in the art to alter their stability, solubility, binding affinity, and specificity. For example, the sequences are selectively methylated. The nucleic acid sequences of the present invention are also modified with a label capable of providing a detectable signal, either directly or indirectly. Exemplary labels include radioisotopes, fluorescent molecules, biotin, and the like.

The present invention also provides vectors that include nucleic acids encoding CD80, CD86, CD28 or CTLA-4 polypeptide(s) in part or in whole. Such vectors include, for example, plasmid vectors for expression in a variety of eukaryotic and prokaryotic hosts. Preferably, vectors also include a promoter operably linked to the feline CD80, CD86, CD28 or CTLA-4 polypeptide encoding portion. The encoded feline CD80, CD86, CD28 or CTLA-4 polypeptide(s) are expressed by using any suitable vectors and host cells as explained herein or otherwise known to those skilled in the art.

Suitable vectors for use in practicing the present invention include without limitation YEp352, pcDNAI (Invitrogen, Carlsbad, Calif.), pRc/CMV (Invitrogen), and pSFV1 (GIBCO/BRL, Gaithersburg, Md.). One preferred vector for use in the invention is pSFV1. Suitable host cells include *E. coli*, yeast, COS cells, PC12 cells, CHO cells, GH4C1 cells, BHK-21 cells, and amphibian melanophore cells. BHK-21 cells are a preferred host cell line for use in practicing the present invention. Suitable vectors for the construction of naked DNA or genetic vaccinations include without limitation pTarget (Promega, Madison, Wis.), pSI (Promega, Madison, Wis.) and pcDNA (Invitrogen, Carlsbad, Calif.).

Nucleic acids encoding feline CD80, CD86, CD28 or CTLA-4 polypeptide(s) are also introduced into cells by recombination events. For example, such a sequence is microinjected into a cell, effecting homologous recombination at the site of an endogenous gene encoding the polypeptide, an analog or pseudogene thereof, or a sequence with substantial identity to an feline CD80, CD86, CD28 or CTLA-4 polypeptide-encoding gene. Other recombination-based methods such as non-homologous recombinations, and deletion of endogenous gene by homologous recombination, especially in pluripotent cells, are also used.

The present invention provides a method of enhancing an immune response in a feline to an immunogen, which is achieved by administering the immunogen before, after or substantially simultaneously with the feline CD80 or feline CD86 with or without feline CD28 or feline CTLA-4 in an amount effective to enhance the immune response.

The present invention provides a method of enhancing an immune response in a feline to an immunogen, which is achieved by administering an expression vector which contains an immunogen derived from a feline pathogen and the feline CD80 or feline CD86 accessory molecules with or without feline CD28 or feline CTLA-4 in an amount effective to enhance the immune response.

The present invention provides a method of redirecting an immune response in a feline to an immunogen, which is achieved by administering an expression vector which contains an immunogen derived from a feline pathogen and the feline CD80 or feline CD86 accessory molecules with or without feline CD28 or feline CTLA-4 in an amount effective to enhance the immune response.

The present invention provides a method of suppressing an immune response in a feline to an immunogen, which is achieved by administering the immunogen before, after or substantially simultaneously with the feline CD80 or feline CD86 with or without feline CD28 or feline CTLA-4 or with antisense RNA or DNA encoding feline CD80 or feline CD86 or feline CD28 or feline CTLA-4, in an amount effective to suppress the immune response.

The present invention provides a vaccine for inducing an immune response in a feline to an immunogen(s), comprising the immunogen and effective amount of feline CD80 or feline CD86 with or without feline CD28 or feline CTLA-4 for immune response enhancement, or feline CD80 or feline CD86 with feline CTLA-4 for immune response suppression. In another embodiment the invention provides a vaccine comprising an expression vector containing genes for immunogen(s) to feline pathogens and genes for CD80, CD86, with or without feline CD28 or feline CTLA-4 for immune response enhancement or suppression.

Feline CD80, CD86, CD28 or CTLA-4 Polypeptides

Figure 2B:
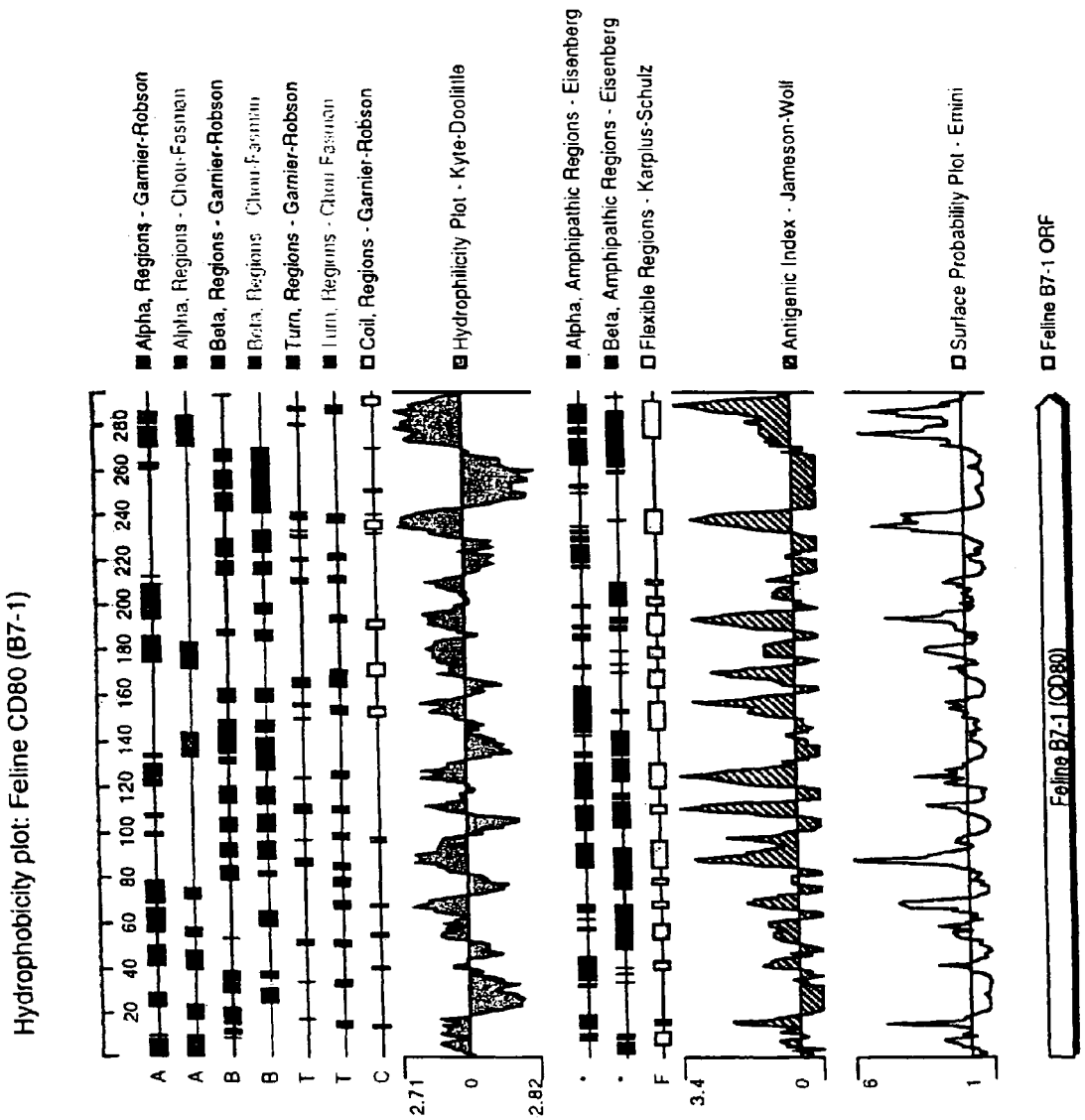
FIG. 2B: Hydrophobicity plot of amino acid sequence of feline CD80 (B7-1) (SYNTRO).
Figure 3B:
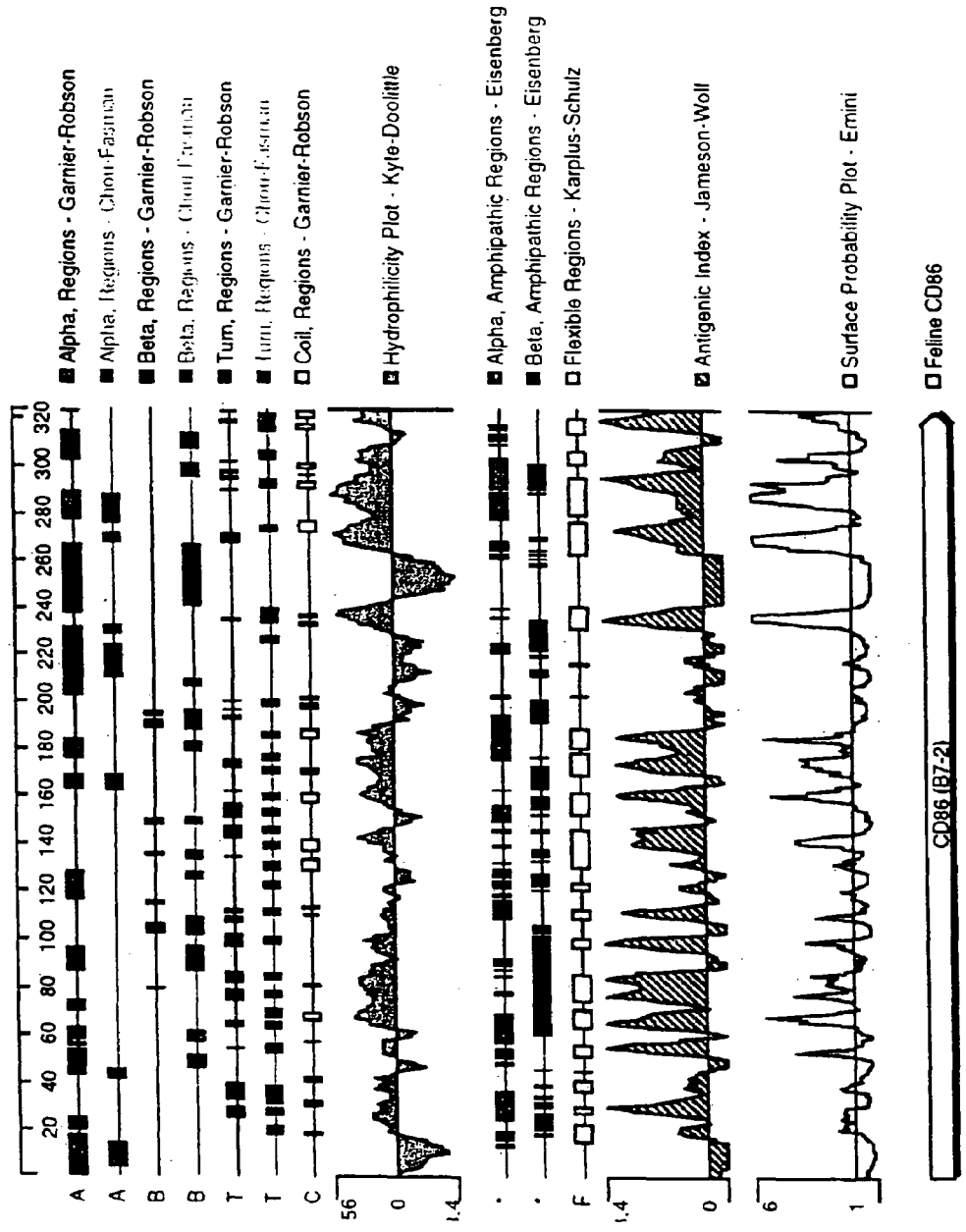
FIG. 3B: Hydrophobicity plot of amino acid sequence of feline CD86 (B7-2).
Figure 5B:
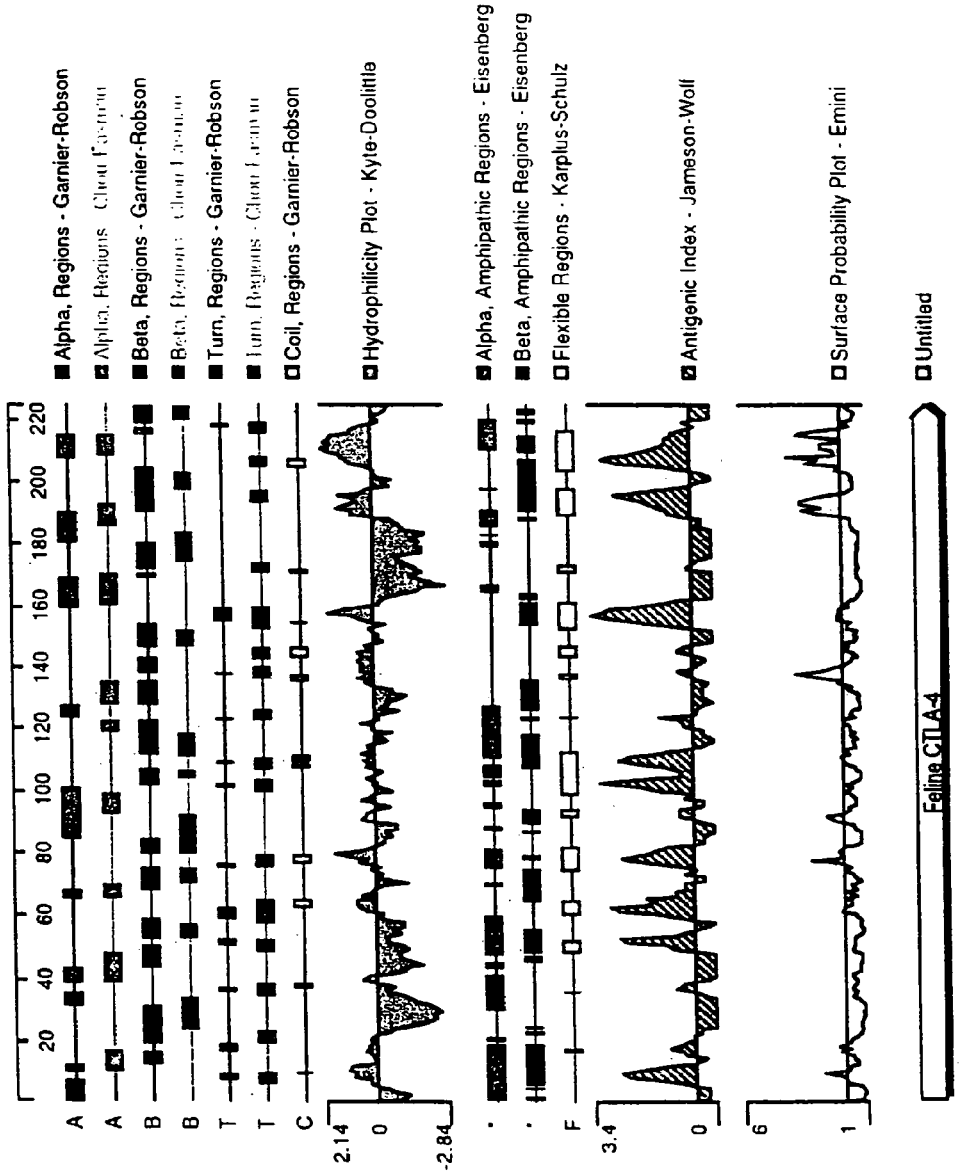
FIG. 5B: Hydrophobicity plot of amino acid sequence of feline CTLA-4 (CD152)

The feline CD80 gene (the cDNA and amino acid sequence of which is shown in FIGS. 1 and 2) encodes a polypeptide of approximately 292 amino acids. The feline CD86 gene (the cDNA and amino acid sequence of which is shown in FIG. 3) encodes a polypeptide of approximately 320 amino acids. The feline CD28 gene (the cDNA and amino acid sequence of which is shown in FIG. 4) encodes a polypeptide of approximately 221 amino acids. The feline CTLA-4 gene (the cDNA and amino acid sequence of which is shown in FIG. 5) encodes a polypeptide of approximately 223 amino acids.

Purification of feline CD80, CD86, CD28 or CTLA-4 from natural or recombinant sources is achieved by methods well-known in the art, including, but not limited to, ion-exchange chromatography, reverse-phase chromatography on C4 columns, gel filtration, isoelectric focusing, affinity chromatography, and the like. In a preferred embodiment, large quantities of bioactive feline CD80, CD86, CD28 or CTLA-4 is obtained by constructing a recombinant DNA sequence comprising the coding region for feline CD80, CD86, CD28 or CTLA-4 fused in frame to a sequence encoding 6 C-terminal histidine residues in the pSFV1 replicon (GIBCO/BRL). mRNA encoded by this plasmid is synthesized using techniques well-known to those skilled in the art and introduced into BHK-21 cells by electroporation. The cells synthesize and secrete mature glycosylated feline CD80, CD86, CD28 or CTLA-4 polypeptides containing 6 C-terminal histidines. The modified feline CD80, CD86, CD28 or CTLA-4 polypeptides are purified from the cell supernatant by affinity chromatography using a histidine-binding resin (His-bind, Novagen, Madison, Wis.).

Feline CD80 or feline CD86 polypeptides isolated from any source are modified by methods known in the art. For example, feline CD80, CD86, CD28 or CTLA-4 are phosphorylated or dephosphorylated, glycosylated or deglycosylated, and the like. Especially useful are modifications that alter feline CD80, CD86, CD28 or CTLA-4 solubility, stability, and binding specificity and affinity.

Feline CD80, CD86, CD-28, CTLA-4 Chimeric Molecules

The present invention encompasses the production of chimeric molecules made from fragments of feline CD80, CD86, CD-28 and CTLA-4 in any combination. For example, introducing the binding site of CTLA-4 in place of the CD-28 binding site, to increase the binding affinity of CD28 while maintaining enhancement of the immune response.

In one embodiment, the binding sites for CD80 or CD86 on CTLA-4 and CD28 are exchanged such that a binding region on CD28 is replaced by a binding region of CTLA-4. The effect of the chimeric CD28 molecule with a CTLA-4 binding region is to increase the affinity of CD28 for CD80 or CD86 and increase the magnitude of enhancement of the immune response. In an alternative embodiment, chimeric molecules of CD80 and CD28 or CD86 and CD28, or fragments thereof, are membrane bound and improve the immune enhancing capabilities of these molecules. In an alternative embodiment, chimeric molecules of CD80 and CTLA-4 or CD86 and CTLA-4, or fragments thereof, are membrane bound and improve the immune suppressing capabilities of these molecules. In an alternative embodiment, chimeric molecules of CD80 and CTLA-4 or CD86 and CTLA-4, or fragments thereof, are membrane bound and redirect the immune response to achieve the desired effect.

Anti-Feline CD80, CD86, CD28 or CTLA-4 Antibodies

The present invention encompasses antibodies that are specific for feline CD80, CD86, CD28 or CTLA-4 polypeptides identified as described above. The antibodies are polyclonal or monoclonal, and discriminate feline CD80, CD86, CD28 or CTLA-4 from different species, identify functional domains, and the like. Such antibodies are conveniently made using the methods and compositions disclosed in Harlow and Lane, *Antibodies, A Laboratory Manual*, Cold Spring Harbor Laboratory, 1988, as well as immunological and hybridoma technologies known to those skilled in the art. Where natural or synthetic feline CD80, CD86, CD28 or CTLA-4-derived peptides are used to induce an feline CD80, CD86, CD28 or CTLA-4-specific immune response, the peptides are conveniently coupled to a suitable carrier such as KLH and administered in a suitable adjuvant such as Freund's.

Preferably, selected peptides are coupled to a lysine core carrier substantially according to the methods of Tan (1988) *Proc. Natl. Acad. Sci. USA,* 85:5409-5413. The resulting antibodies, especially internal imaging anti-idiotypic antibodies, are also prepared using known methods.

In one embodiment, purified feline CD80, CD86, CD28 or CTLA-4 is used to immunize mice, after which their spleens are removed, and splenocytes used to form cell hybrids with myeloma cells to obtain clones of antibody-secreting cells according to techniques that are standard in the art. The resulting monoclonal antibodies secreted by such cells are screened using in vitro assays for the following activities: binding to feline CD80, CD86, CD28 or CTLA-4, inhibiting the receptor-binding activity of CD80, CD86, CD28 or CTLA-4, and inhibiting the T-cell stimulatory activity of CD80, CD86, CD28 or CTLA-4.

Anti-feline CD80, anti-feline CD86, anti-feline CD28 or anti-feline CTLA-4 antibodies are used to identify and quantify feline CD80, CD86, CD28 or CTLA-4, using immunoassays such as ELISA, RIA, and the like. Anti-feline CD80, anti-feline CD86, anti-feline CD28 or anti-feline CTLA-4 antibodies are also be used to immunodeplete extracts of feline CD80 or feline CD86 or feline CD28 or feline CTLA-4. In addition, these antibodies can be used to identify, isolate and purify feline CD80, CD86, CD28 or CTLA-4 from different sources, and to perform subcellular and histochemical localization studies.

Applications

Feline CD80 (B7-1) ligand, feline CD86 (B7-2) ligand, feline CD28 receptor or feline CTLA-4 (CD 152) receptor produced according to the present invention can be used beneficially as a vaccine to prevent infectious disease or to promote growth in homologous or heterologous feline species. For example, the coexpression of CD80 or CD86, with costimulatory molecules CD28 or CTLA-4, in any combination, and a tumor antigen or antigens from a pathogenic organism. The coexpression of feline CD80 or CD86, with a feline CTLA-4 receptor has the ability to inhibit activation of T-lymphocytes and suppress an immune response. A specific example would be to coexpress CD80 or CD86, with FIV, FeLV, or FIP derived immunogens in a viral vector or DNA expression vector, which, when administered as a vaccine would activate, enhance or regulate the proliferation of CD4+ and CD8+ T-lymphocytes, and induce immune-regulating cytokines such as IL-2, IFN-γ, IL-12, TNFα, IL-6 and the like. Another specific example would be to express CD80, CD86, CD28 or CTLA-4 in a viral vector or DNA expression vector, which, when administered as a therapeutic would regulate or re-direct the immune response.

Enhancement of immunity through the interaction of feline CD80 or CD86 with CD28 or CTLA-4 or inhibition of an immune response through the interaction of feline CD80 or CD86 with CTLA-4 takes advantage of the natural process of regulation rather than adding foreign substances that could have multiple even detrimental effects on overall or long term health. The CD80, CD86, CD28 or CTLA-4 molecules are administered with other recombinant molecules, such as those encoding antigens that are desirable for induction of immunity. The feline CD80, CD86, CD28 and/or CTLA-4 gene is inserted into an expression vector and infected or transfected into a target cell and expresses the gene product within the target cell so that it is anchored into the plasma membrane of the target cell or antigen presenting cell, or secreted outside the target cell or antigen presenting cell. An expression vector, such as a plasmid, Semliki Forest virus, a poxvirus or a herpesvirus, transfers the gene to the antigen presenting cell. The feline CD80, CD86, CD28 and/or CTLA-4 gene or fragments of genes in any combination is inserted into a DNA or RNA expression vector and injected into a feline and expresses the gene product in the feline as a "naked" DNA/RNA or genetic vaccine. The co-expression of immunogen and the CD80, CD86, CD28 and/or CTLA-4 within a target cell or feline contributes to the activation, enhanced activation, or regulation of T lymphocytes, B lymphocytes and other cells. Alternatively, the expressed protein could be administered following expression in a plasmid. The feline CD80, CD86, CD28, or CTLA-4 proteins normally function anchored in the cell membrane as plasma membrane accessory molecules, but may be presented in other forms, particularly without membrane anchors.

In an one embodiment, the feline CD80 and feline CD86 are soluble, lacking a transmembrane domain or hydrophobic region, and interact with costimulatory molecules CD28 or CTLA-4, in either a membrane bound or soluble form. In an alternative embodiment, the feline CD80 or feline CD86 are membrane bound and the costimulatory molecules CD28 or CTLA-4 are in a soluble form, lacking a transmembrane domain or hydrophobic region. The soluble CD28 or CTLA-4, preferably in a dimeric form, is useful for treating disease related to T-cell mediated immunosuppression in cats. Soluble CD28 or CTLA-4 prevents rejection of transplanted tissue and can be used to treat autoimmune disease. Specifically soluble CD28 or CTLA-4 is useful for preventing graft versus host disease in a bone marrow transplant. Soluble CD28 or CTLA-4 prevents binding of a cell containing membrane bound feline CD80 or CD86.

Sequence-conservative and functional conservative variants of feline CD80, CD86, CD28 or CTLA-4 DNA and polypeptides or a bioactive feline CD80, CD86, CD28 or CTLA-4 fragment or sub-fragment are fused in frame to another sequence, such as a cytokine, interleukin, interferon, colony stimulating factor, antigen from a pathogenic microorganism, antibody, or purification sequence, such as a his-tag or a reporter gene, such as E. coli lacZ, E. coli uidA, or green fluorescent protein.

Vaccines

The present invention encompasses methods and composition for enhancing the efficacy of an immune response in feline species. In this embodiment, feline CD80, CD86, CD28 or CTLA-4 are used in conjunction with an immunogen for which it is desired to elicit an immune response. For example, in feline vaccines containing immunogens from pathogens such as feline immunodeficiency virus and feline leukemia virus, and other pathogens such as feline parvovirus, feline leptovirus, and feline coronavirus, it is desirable to include feline CD80, CD86, CD28 or CTLA-4 in the vaccine to regulate the magnitude and quality of the immune response. For this purpose, feline CD80, CD86, CD28 or CTLA-4 purified from native or recombinant sources as described above is included in the vaccine formulation at a concentration ranging from about 0.01 to 100.0 mg per vaccine per cat.

Commercial sources of feline vaccines are known to those skilled in the art (Compendium of Veterinary Pharmaceuticals, 1997) and are used in combination with the present invention for a more effective vaccine.

A vaccine for inducing and regulating an immune response in a feline to an immunogen, is comprised of an immunogen and an effective amount of feline CD80 or feline CD86 with or without feline CD28 or feline CTLA-4 for immune response enhancement, or feline CD80 or feline CD86 with feline CTLA-4 for immune response suppression.

The immunogen is selected from the group comprising, but not limited to, feline pathogens such as feline immunodeficiency virus, feline leukemia virus, feline infectious peritonitis virus, feline panleukopenia virus (parvo), feline calicivirus, feline reovirus type 3, feline rotavirus, feline coronavirus (Infectious peritonitis), rabies virus, feline syncytial virus, feline sarcoma virus, feline herpesvirus (rhinotracheitis virus), feline Borna disease virus, Chlamydia, Toxoplasmosis gondii, feline parasites, Dirofilaria immitis, fleas, bacterial pathogens, and the like.

Regulation of the growth or regulation of activation of a cell type, such as a T-lymphocyte, indicates that the regulatory response either stimulates or suppresses cell growth. Regulation of an immune response in a feline indicates that the immune response is either stimulated or suppressed to treat the disease or infectious agent in the feline.

Expression of feline CD80, CD86, CD28, or CTLA-4, alone or in any combination in part or in whole, in an expression vector containing gene(s) for feline immunogens for the purpose of administering as a genetic vaccine or naked DNA vaccine. Vectors include but are not limited to: pTarget (Promega, Madison, Wis.); pcDNA (Invitrogen, Carlsbad, Calif.). (Donnelly J. J., et al., 1997; Hassett and Whitton, 1996.)

The genes or fragments of the genes for CD80, CD86, CD28, and CTLA-4, alone or in any combination, in part or in whole, may be inserted or transfected into the chromosomes of a feline or other mammal. Such integration of these genes or fragments of these genes as may be achieved with a retroviral vector and may be used as a form of gene therapy.

The present invention provides methods and compositions for improving resistance to disease of feline species for medical and/or commercial purposes. In this embodiment, feline CD80, CD86, CD28 or CTLA-4, expressed alone or in any combination, in part or in whole, and in combination with or without genes encoding feline immunogens, is administered to felines using any appropriate mode of administration. For growth promotion or disease resistance, feline CD80, CD86, CD28 or CTLA-4, expressed alone or in any combination is administered in a formulation at a concentration ranging from about 0.01 to 100.0 mg per vaccine per cat in amounts, preferably in a formulation at a concentration ranging from about 0.25 mg/kg/day to about 25 mg/kg/day. It will be understood that the required amount of feline CD80, CD86, CD28 or CTLA-4 can be determined by routine experimentation well-known in the art, such as by establishing a matrix of dosages and frequencies and comparing a group of experimental units or subjects to each point in the matrix.

According to the present invention, native or recombinant feline CD80, CD86, CD28 or CTLA-4 is formulated with a physiologically acceptable carrier, such as, for example, phosphate buffered saline or deionized water. The formulation may also contain excipients, including lubricant(s), plasticizer(s), absorption enhancer(s), bactericide(s), and the like that are well-known in the art. The feline CD80, CD86, CD28 or CTLA-4 polypeptide of the invention is administered by any effective means, including without limitation intravenous, subcutaneous, intramuscular, transmuscular, topical, or oral routes. For subcutaneous administration, for example, the dosage form consists of feline CD80, CD86, CD28 or CTLA-4 in sterile physiological saline. For oral or respiratory administration, feline CD80, CD86, CD28 or CTLA-4, with or without excipients, is micro- or macro-encapsulated in, e.g., liposomes and microspheres. Dermal patches (or other slow-release dosage forms) are also be used.

EXAMPLES

Example 1A

Cloning of the Feline CD80 (B7-1)-TAMU, CD86 (B7-2), CD28, and CTLA-4 cDNA

The feline CD80 (B7-1), CD86 (B7-2), CD28, and CTLA-4 cDNA were cloned by first RT-PCR (Reverse transcriptase/Polymerase chain reaction) amplifying a region between two sequences that were conserved enough to make degenerate primers that interacted with the feline mRNA. The source of the mRNA was peripheral blood mononuclear cells (PBMC) stimulated for at least 16 hours with Con A. This PCR product was sequenced. The sequence was used to make primers for RACE (rapid amplification of cDNA ends) PCR. The 5' end was amplified by first making cDNA with a downstream primer complimentary to the newly sequenced conserved region. An oligonucleotide was ligated to the 3' end of the cDNA (compliment with the 5' end of mRNA). This sequence served as the binding site for the upstream primer which was PCR compatible with the downstream PCR primer that corresponded with another region in the newly sequenced region. Degenerate primers were employed in multiple rounds of nested reactions to obtain the 3' end. This upstream primer for PCR was designed to react with a sequence in the newly sequenced region. Products were either sequenced directly or cloned into a TA cloning vector and sequenced from the plasmid. The whole open reading frame was cloned by amplifying in its entirety by PCR with primers constructed from the known sequences. The ORFs were cloned and sequenced three times. The B7-1 ORF was subcloned into a pSI plasmid with an SV40 promoter, and the SFV plasmid. The pSI was used to establish the functional interaction of B7-1 with the feline CD28.

DNA Primers Used for RT/PCR of the Feline CD80 (B7-1) cDNA were:

(SEQ ID NO: 11)
5' Primer: 5'-CGCGGATCCGCACCATGGGTCACGCAGCAAAG

TGGAAAAC-3';

(SEQ ID NO: 12)
3' Primer: 5'-CCTAGTAGAGAAGAGCTAAAGAGGC-3';;

(See above for complete list of primers for feline CD28 cDNA).

DNA Primers Used for RT/PCR of the Feline CD28 cDNA were:

(SEQ ID NO: 13)
5' Primer: 5'-CGCGGATCCACCGGTAGCACAATGATCCTC

AGG-3';

(SEQ ID NO: 14)
3' Primer: 5'-CGCGGATCCTCTGGATAGGGGTCCATGTCAG-3';

(See above for complete list of primers for feline CD28 cDNA).

DNA Primers Used for RT/PCR of the Feline CTLA-4 cDNA were:

1. Degenerate primers for the first PCR product (672 bp):

(SEQ ID NO: 15)
Deg 5' P: 5'-ATGGCTT(C)GCCTTGGATTT(C)CAGC(A)GG-3';

(SEQ ID NO: 16)
Deg 3' P: 5'-TCAATTG(A)ATG(A)GGAATAAAATAAGGCTG-3';

2. 5' end of CTLA-4 (455 bp): Degenerate, gene-specific (GSP) and nested gene-specific (NGSP) primers:
First Round PCR:

(SEQ ID NO: 17)
Deg 5' P: 5'-TGTTGGGTTTC(T)G(A)CTCTG(A)CTT (C)CCTG-3';

(SEQ ID NO: 18)
3' GSP: 5'-GCATAGTAGGGTGGTGGGTACATG-3';

Nested PCR with the PCR Product of the First Round:

(SEQ ID NO: 19)
Deg 5' P: 5'-TGTTGGGTTTC(T)G(A)CTCTG(A)CTT(C)

CCTG-3';

-continued

```
                                            (SEQ ID NO: 20)
3' NGSP: 5'-ACATGAGCTCCACCTTGCAG-3';
```

3. 3' end of CTLA-4: Adaptor primer 1 (API, Clonetech Lab, Inc., Palo Alto, Calif.); Nested adaptor primer (AP2, Clonetech Lab), gene-specific primer (GSP), and nested gene-specific primer (NGSP):
3' RACE PCR:

```
                                            (SEQ ID NO: 21)
AP1: 5'-CCATCCTAATACGACTCACTATAGGGC3'

(SEQ ID NO: 22)
5' GSP: 5'-GTGAATATGGGTCTTCAGGCAATG-3';
```

3' Nested RACE PCR with the Product of 3' RACE PCR:

```
                                            (SEQ ID NO: 23)
AP2: 5'-ACTCACTATAGGGCTCGAGCGGC-3';

(SEQ ID NO: 24)
5' NGSP: 5'-GAAATCCGAGTGACTGTGCTGAG-3';
```

4. Primers for whole CTLA-4 gene

```
                                            (SEQ ID NO: 25)
Fel CTLA-4 5' Primer: 5'-AACCTGAACACTGCTCCCATA
AAG-3';

(SEQ ID NO: 26)
Fel CTLA-4 3' Primer: 5'-GCCTCAGCTCTTAGAAATTGGA
CAG-3';
```

DNA Primers Used for RT/PCR of the Feline CD86 (B7-2) cDNA were:
1. Degenerate primers for the first PCR product (423 bp):

```
                                            (SEQ ID NO: 27)
Deg 5' P: 5'-TAGTATTTTGGCAGGACCAGG-3';

(SEQ ID NO: 28)
Deg 3' P: 5'-CTGTGACATTATCTTGAGATTTC-3';
```

2. Degenerate primers for the second PCR product (574 bp):

```
                                            (SEQ ID NO: 29)
Deg 5' P: 5'-GA(G)CA(T)GCACT(A)ATGGGACTGAG-3';

(SEQ ID NO: 30)
Deg 3' P: 5'-CTGTGACATTATCTTGAGATTTC-3';
```

3. 5' end of CD86: AP1, AP2 (Clontech Lab), Degenerate, 3'-gene-specific (GSP) and 3'-nested gene-specific (NGSP) primers:
5' RACE PCR:

```
                                            (SEQ ID NO: 31)
AP1: 5'-CCATCCTAATACGACTCACTATAGGGC-3';

(SEQ ID NO: 32)
3' GSP: 5'-TGGGTAACCTTGTATAGATGAGCAGGTC-3';
```

Nested 5' RACE PCR with the PCR Product of 5' RACE:

```
                                            (SEQ ID NO: 33)
AP2: 5'-ACTCACTATAGGGCTCGAGCGGC-3';
```

-continued

```
                                            (SEQ ID NO: 34)
3' NGSP: 5'-CAGGTTGACTGAAGTTAGCAAGCAC-3';
```

4. 3' end of B7-2: API, AP2, 5' GSP, and 5' NGSP:
3' RACE PCR:

```
                                            (SEQ ID NO: 35)
AP1: 5'-CCATCCTAATACGACTCACTATAGGGC-3';

(SEQ ID NO: 36)
5 GSP: 5'-GGACAAGGGCACATATCACTGTTTC-3';
```

Nested 3' RACE PCR with the PCR Product of 3' RACE:

```
                                            (SEQ ID NO: 37)
AP2: 5'-ACTCACTATAGGGCTCGAGCGGC-3';

(SEQ ID NO: 38)
5' NGSP: 5'-CAGTGCTTGCTAACTTCAGTCAACC-3';
```

Whole CD86 Gene

```
                                            (SEQ ID NO: 39)
Fel B72 (1) 5' Primer: 5'-CGGGAATGTCACTGAGCTT
ATAG-3';

(SEQ ID NO: 40)
Fel B72 (1176) 3' Primer: 5'-GATCTTTTTCAGGTTAGCA
GGGG-3';
```

Example 1B

Cloning of CD80 (B7-1)-Syntro/SPAH; Plasmid 917-19-8/16 Feline spleen cells were extracted from cats and cultured with Concanavalin A for 5 hours, Cells were pelleted, washed with PBS and used to isolate total RNA (Qiagen RNeasy Total RNA System). Total RNA was treated with DNAse I (Boehringer Mannheim) to remove DNA contamination from the RNA preparations. Messenger RNA was then extracted from these preparations, using Qiagen's Oligotex beads (Santa Clara, Calif.) and quick columns. Copy DNA was generated from mRNA, in the presence of random hexamers, dNTPs, RNAsin, reverse transcriptase (Promega) and reverse transcriptase buffer (Promega) and incubated at 42° C. for 30 minutes. PCR was then used to generate a double stranded, full-length cDNA clone of the feline B7-1 open reading frame (ORF) using the sense primer 5/97.50 (5'-ATGGGTCACG-CAGCAAAGTG-3'); (SEQ ID NO: 41) and antisense primer 5/97.51 (5'-CTATGTAGACAGGTGAGATC-3'); (SEQ ID NO: 42), dNTPs, B7-1 cDNA (1st strand), $MgSO_4$, Vent polymerase (BRL) and Vent polymerase buffer (BRL). PCR conditions were as follows: 1 cycle of 94°, 15 seconds; 35 cycles of 94° for 30 seconds 48° for 2 minutes; 1 cycle of 72° for 10 minutes. PCR reactions were run on a 1% low melt agarose gel and DNA fragments corresponding to the expected size of the B7-1 ORF were isolated, gel purified (Qiagen's Gel Purification Kit, Santa Clara, Calif.) and cloned into pCR-BLUNT plasmid vector using kit reagents from Invitrogen's Zero Blunt PCR Cloning Kit (San Diego, Calif.). DNA extracted from kanamycin resistant bacterial colonies were pre-screened for the presence of a unique NheI site (contained in feline CD80 (B7-1)-TAMU). Inserts that were in the range of 800-900 by size and contained a NheI site were sequenced using ABI's fluorescenated automated sequencing protocols and equipment (Perkin-Elmer-Cetus;

Applied Biosystems, Inc.). Plasmid vector and B7-1, gene specific primers derived from the previously cloned B7-1 gene were used to generate DNA sequence pCR-Blunt primers are 1/97.36 (5'-CAGGAAACAGCTATGAC-3'); (SEQ ID NO: 43) and 1/97.37 (5'-AATACGACTCACTATAGG-3'); (SEQ ID NO: 44). B7-1 gene specific primers are:

```
                                           (SEQ ID NO: 45)
    12/96.22 (5'-AACACCATTTCATCATCCTTT-3');, (SEQ ID NO: 46)
    1/97.33 (5'-ATACAAGTGTATTTGCCATTGTC-3');, (SEQ ID NO: 47)
    12/96.20 (5'-AGCTCTGACCAATAACATCA-3');

(SEQ ID NO: 48)
    12/96.21 (5'-ATTAGAAATCCAGTTCACTGCT-3');, (SEQ ID NO: 49)
    1/97.32 (5'-TCATGTCTGGCAAAGTACAAG-3);, (SEQ ID NO: 50)
    11/96.32 (5'ATTCACTGACGTCACCGA-3');, (SEQ ID NO: 51)
    11/96.31 (5'-AAGGCTGTGGCTCTGA-3');.
```

Two clones were determined to contain full-length CD80 sequence corresponding to the original CD80 sequence with the exception of 2 DNA point mutations. One such point mutation did not effect the amino acid sequence. The second mutation resulted in an amino acid change from a Leucine to an Isoleucine. The resultant feline CD80 clone was designated 917-19.8/16. (CD80-Syntro/SPAH). To facilitate the cloning of feline CD80 (B7-1) gene behind any pox promoter containing EcoRI and BamHI cloning sites, two new primers were designed to introduce EcoRI and BamHI restriction enzyme cloning sites onto the 5' and 3' end of the CD-80 ORF, respectively. These two primers are: sense primer 1/97.43 (5'-TCGAGAATTCGGGTCACGCAGCAAAGTGG-3'); (SEQ ID NO: 52) and antisense primer 1/97.6 (5'-GCTAGGATCCAATCTATGTAGACAGGTGAGAT-3'); (SEQ ID NO: 53). The resultant PCR fragment was digested with EcoRI and BamHI and cloned into an O1L SPV homology vector (AccI insertion site within the swinepox virus HindIII M genomic fragment) for the generation of a recombinant SPV virus. This resulted in the cassette, 930-23.A1, a SPV O1L homology vector containing the feline CD80 ORF behind the late/early synthetic pox promoter, LP2EP2, and adjacent to the *E. coli* lacZ marker gene cassette promoted by synthetic late pox promoter, LP2. Plasmid vector, 930-23.A1, was cotransfected with SPV 001 to generate a recombinant SPV virus expressing the feline B7-1 and *E. coli* β-galactosidase proteins.

Example 1C

Subcloning of CD-28 into Pox Viral Homology Vector The coding region of feline CD-28 was PCR amplified with synthetic primers containing convenient cloning sites, to facilitate cloning CD-28 behind any pox promoter for the construction of a pox specific homology vector. The synthetic primers were made to introduce an EcoRI and BglII cloning site at the 5' and 3' ends of the PCR fragment, respectively. The two primers are: sense primer, 7/97.1 (5'-GATGAATTCCATGATCCTCAGGCTGGGCTTCT-3'); (SEQ ID NO: 54) and antisense primer 7/97.2 (5'-GATCAGATCTCAGGAACGGTATGCCGCAA-3'); (SEQ ID NO: 55). The resultant PCR DNA fragment was digested with EcoRI and BglII and cloned into an O1L SPV homology vector for the generation of a recombinant SPV virus. This resulted in the cassette, 930-26.A1, a SPV OIL homology vector (AccI insertion site within the swinepox virus HindIII M genomic fragment) containing the feline CD-28 ORF behind the late/early synthetic pox promoter, LP2EP2, and adjacent to the *E. coli* lacZ marker gene cassette promoted by a synthetic late pox promoter, LP2. Homology plasmid vector, 930-26.A1, was cotransfected with SPV 001 to generate a recombinant SPV virus expressing the feline CD-28 and β-galactosidase proteins.

Example 2

Characterization of the feline CD80 (B7-1)-TAMU, CD86 (B7-2), CD28, CTLA-4 and CD80 (B7-1)-Syntro/SPAH cDNAs and polypeptides: The isolated and purified feline CD80 (B7-1) cDNA of approximately 941 nucleotides codes for an open reading frame of the feline CD80 polypeptide of approximately 292 amino acids, the native membrane bound or mature form of which has a molecular mass of about 33,485 kDa, an isoelectric point of about 9.1, a net charge at pH 7.0 of 10.24. The transmembrane domain of the protein is approximately amino acids 241 to 271.

Feline CD80-TAMU and feline CD80-Syntro/SPAH are cDNAs and polypeptides isolated independently from two different sources, and the DNA and amino acid sequences differ slightly. The source of the CD80-TAMU mRNA was feline peripheral blood mononuclear cells stimulated with ConA, and the source of the CD80-Syntro/SPAH mRNA was feline spleen cells stimulated with ConA. The difference in cDNA sequence between CD80-TAMU and CD80-Syntro/SPAH is T to C at nucleotide 351 and C to A at nucleotide 670. At the amino acid sequence, the change at nucleotide 351 is silent, and the change at nucleotide 670 results in a conservative change of neutral amino acids, leucine to isoleucine, at amino acid residue 224.

The isolated and purified feline CD86 (B7-2) cDNA of approximately 1176 nucleotides codes for an open reading frame of feline CD86 polypeptide of approximately 320 amino acids, the native membrane bound or mature form of which has a molecular mass of approximately 36,394 kDa, an isoelectric point of about 9.19, a net charge at pH 7.0 of 11.27.

The isolated and purified feline CD28 cDNA of approximately 689 nucleotides codes for an open reading frame of feline CD28 polypeptide of approximately 221 amino acids, the native membrane bound or mature form of which has a molecular mass of about 25,319 kDa, an isoelectric point of about 9.17, a net charge at pH 7.0 of 9.58. The isolated and purified feline CTLA-4 cDNA of approximately 749 nucleotides codes for an open reading frame of feline CTLA-4 polypeptide of approximately 223 amino acids, the native membrane bound or mature form of which has a molecular mass of about 24,381 kDa, an isoelectric point of about 6.34, a net charge at pH 7.0 of −0.99.

The coexpression of CD80, with costimulatory molecules CD28 or CTLA-4, and a tumor antigen or an antigen from a pathogenic organism, has the ability to activate or enhance activation of T-lymphocytes, more specifically Th-1 lymphocytes, and to promote the growth of other cell types. The coexpression of CD80, with costimulatory molecule CTLA-4, has the ability to suppress activation of T-lymphocytes, more specifically Th-1 lymphocytes. The coexpression of CD86, with costimulatory molecules CD28 or CTLA-4, and a tumor antigen or an antigen from a pathogenic organism, has the ability to activate or enhance activation of T-lymphocytes, more specifically Th-1 lymphocytes, and to promote the growth of other cell types. The coexpression of CD86, with costimulatory molecule CTLA-4, has the ability to suppress activation of T-lymphocytes, more specifically Th-1 lymphocytes.

CD80, CD86, CD28, and CTLA-4 on the surface of the tumor cell raises a broad immunological response to transfected and non-transfected tumor cells resulting in killing of localized and metastatic tumor cells. In an alternate procedure, vectors

| | DNA and Amino Acid Percentage Sequence Identity | | | | | |
|---|---|---|---|---|---|---|
| | Human Homologue (DNA Sequence) % Identity | Human Homologue (AA Sequence) % Identity | Mouse Homologue (DNA Sequence) % Identity | Mouse Homologue (AA Sequence) % Identity | Rabbit Homologue (DNA/AA Sequence) % Identity | Chicken Homologue (DNA/AA Sequence) % Identity |
| FelineCD80 | 77 | 59 | 62 | 46 | — | — |
| FelineCD86 | 72 | 68 | — | — | 67/64 | — |
| FelineCD28 | 85 | 82 | 77 | 74 | 84/84 | 59/50 |
| FelineCTLA- | 88 | 88 | 79 | 78 | — | — |

Example 3

Use of feline CD80 (B7-1), CD86 (B7-2), CD28, and CTLA-4 in Vaccines The following experiments are performed to evaluate the immune-enhancing activities of feline CD80, CD86, CD28, and CTLA-4 in feline vaccines.

In an alternate procedure, cats at 8 weeks of age are injected intramuscularly with 100 μg of plasmid containing cDNA for feline CD80, CD86, CD28, and CTLA-4 molecules in a mixture with a plasmid containing cDNA for FIV env and gag or FeLV env and gag, or alternatively, injected intramuscularly with 100 μg of plasmid containing cDNA expressing pairwise combinations of CD80 and CD28, or CD80 and CTLA-4, or CD86 and CD28 or CD86 and CTLA-4 paired with CD28 or CTLA-4, in a mixture with a plasmid containing cDNA for FIV env and gag or FeLV env and gag. Control cats do not receive CD80, CD86, CD28, and CTLA-4. Cats are challenged with virulent FeLV or FIV and observed for signs of disease as described above. The results of the challenge experiment are that cats receiving the cDNA vector containing feline CD80, CD86, CD28, and CTLA-4 and cDNA vector containing FIV genes or FeLV genes show 100% protection from disease compared to cats receiving only cDNA vector containing FIV genes or FeLV genes who show 75% protection from disease.

In an alternate procedure, cats at 8 weeks of age are injected intramuscularly with 0.1 to 100 mg of purified protein for feline CD80, CD86, CD28, and CTLA-4 molecules or alternatively, pairwise combinations of CD80 or CD86 paired with CD28 or CTLA-4 proteins, from recombinant cDNA vectors described above, and injected intramuscularly with 0.1 to 100 mg of a subunit vaccine containing FIV env and gag or FeLV env and gag. Control cats do not receive CD80, CD86, CD28, and CTLA-4. Cats are challenged with a virulent FIV strain or FeLV strain and observed regularly for development of disease. The results of the challenge experiment are that cats receiving the purified protein for feline CD80, CD86, CD28, and CTLA-4 and subunit vaccine containing FIV or FeLV show significantly reduced incidence of disease compared to cats receiving only subunit vaccine containing FIV or FeLV proteins.

Example 4

Use of Feline CD80, CD86, CD28, and CTLA-4 to Inhibit and Destroy Tumor Cell Growth Tumor cells from a cat are transfected with a vector expressing feline CD80 or CD86 in combination with CD28 or CTLA-4. The transfected tumor cells are re-administered to the cat, and the presence of the expressing feline CD80 or CD86 in combination with CD28 or CTLA-4 are injected directly into a tumor in a cat resulting in a broad immunological response to the tumor cells resulting in killing of localized and metastatic tumor cells.

Example 5

Cloning and Sequencing of Feline CD80 cDNA
Introduction

In addition to cytokines, some cell surface molecules have been shown to enhance or suppress a distinct immune response. CD80 (B7-1) is an accessory molecule that binds its receptor CD28 on T-cells (Freeman et al., 1989). This interaction functions in the delivery of a secondary stimuli that, in conjunction with the primary signal delivered by T-cell receptor recognition of antigen presented in the context of MI-IC, results in T cell activation and proliferation (Allison and Lanier, 1994). Although it was first described as a B-cells antigen, CD80 has subsequently been found to be expressed on a variety of cell types, most with antigen presenting capabilities (Freeman et al., 1989).

In primates and rodents, the CD80 molecule is a 60 kDa polypeptide composed of approximately 290 amino acids (Freedman et al., 1987; Freeman et al., 1989). The confirmation of the putative amino acid sequence suggests characteristics that distinguish it as a member of the immunoglobulin superfamily (IgSF) (Peach et al., 1995). It is composed of two extracellular IgSF domains, a hydrophobic transmembrane domain and a short cytoplasmic tail (Freeman et al., 1989). The extracellular domain of the mature peptide has a 124 residue $NH_3$ terminal IgSF variable (V)-like region followed by a 100 amino acid IgSF constant (C)-like domain (Freeman et al., 1989). The human counterpart has eight potential N-linked glycosylation sites, and although the mature peptide is highly glycosylated, these carbohydrate residues are not thought to be involved in binding to CD28 or CTLA-4, as they are considered to be oriented opposite the proposed binding domain (Bajorath et al., 1994). Furthermore, removal of the carbohydrate residues does not appear to influence the binding capabilities, rather it is proposed that their function is to increase the solubility of the extracellular portion of the molecule (Linsley et al., 1994a).

CD80 binds to two distinct receptors expressed at different times in the course of T-cell activation. CD28 is found on a variety of thymocytes and naive and activated T-cells, and has a demonstrable role in T-cell activation and proliferation (Aruffo, 1987). The second CD80 receptor, CTLA-4, is usually found at a later time on fully activated T-cells (Linsley et al., 1991b). Although a role for CTLA-4 has not been definitively established, it is hypothesized that the molecule may act to suppress an active and existing T cell response (Hutchcrofi and Bierer, 1996).

The CD80 molecule itself does not appear to have signaling capacity. The cytoplasmic region is relatively short with no residues with demonstrable signaling or enzymatic function (Hathcock et al., 1994). The lack of conservation in the cytoplasmic tail between the murine and human peptides also reflects the probability that the CD80 lacks signaling function and acts solely to cross-link CD28 or CTLA-4 (Linsley et al., 1994a).

The interaction between CD80 and CD28 has been demonstrated to be necessary for the maturation of naive T-cells to an activated state, thus initiating a primary T-cell response (Damle et al., 1988). Although CD80 was first identified on activated B-cells (Freedman et al., 1987), it has subsequently been found on most subsets of professional antigen presenting cells including macrophages/monocytes (Freedman et al., 1987), Langerhan's cells (Symington et al., 1993), dendritic cells (Liu et al., 1992), activated T-cells (Razi-Wolf et al., 1992) and a variety of tumor lines (Chen et al., 1992). The presence of the CD80 molecule on APC has been shown to be important in the activation of both $CD4^+$ and $CD8^+$ T-cells (Allison and Lanier, 1994; Bellone et al., 1994). Although the molecule is normally only present at significant levels on professional APC, some tumor cell lines have been demonstrated to up-regulate the signaling molecule (Chen et al., 1992).

In response to transformation, it appears that some oncogenic lines up-regulate CD80 expression. In these non-antigen presenting cell derived tumors, as well as in some immortalized cell lines, CD80 is surface expressed at levels sufficient to promote full T cell activation (Chen et al., 1992). Although the kinetics of expression are unclear, it is possible that tumor derived CD80 may be a response to the "oncogenic insult," and an evolutionary mechanism through which the immune system can remove transformed or tumorgenic cells (Antonia et al., 1995).

The role of the CD28-B7 interaction appears critical in primary T-cell activation. The recognition of antigen in the context of the MHC by the TCR is in itself insufficient to initiate optimal proliferation and activation of T-cells (Schwartz, 1992). TCR stimulation in the absence of accessory signals can lead to a state of anergy or hyporesponsiveness in T-cell populations (Jenkins et al., 1987). The binding of the CD28 molecule on the T-cell with the CD80 molecule on the antigen presenting cell appears to deliver the second signal required to activate the T-cell (Schwartz, 1992). When the TCR is engaged, in the absence of this second signal, naive cells do not become activated and can become anergic (Lanier et al., 1995). This critical role for the CD28-CD80 interaction has been clearly defined not only in the activation of naive $CD4^+$ cells, but also in $CD4^+$ Th1 and Th2 clones and naive and memory $CD8^+$ T-cells derived from small resting peripheral blood lymphocytes (Linsley et al., 1993a).

As with the CTLA-4/CD28 family, there is also at least one additional counter receptor related to CD80. Initial studies attempting to demonstrate the importance of CD80 in a primary immune response encountered problems because although the introduction of CTLA-4Ig inhibited immune responses, the addition of monoclonal antibody (mAb) to CD80 did not seem to elicit analogous results (Lenschow et al., 1993). The development of CD80 knockout mice inadvertently led to the discovery of the second CTLA-4/CD28 receptor (Freeman et al., 1993). It was felt that these mice would share a similar phenotype with previously developed CD28 knockouts who had an inadequate T cell response (Freeman et al., 1993). It was found however in CD80 knockouts that a normal response developed and that APC were able to provide the necessary secondary signal for T cell maturation (Freeman et al., 1993). From these results a second receptor was hypothesized and eventually isolated. The subsequent discovery of the related CD86 (B7-2 or B7-0) receptor seems to have resolved the discrepancies found in CD80 knockouts and in conjunction with structural and binding similarities reflects the probability that the molecules share a common function and origin (Hathcock et al., 1994).

CD86 (B7-2) demonstrates some similarity with CD80, sharing a structurally similar extracellular IgSF V-region and C-region (Freeman et al., 1993). Overall homology between the molecules however is less than 25% with conserved residues found scattered on opposite faces of both extracellular domains (Bajorath et al., 1994). While a binding region has not been defined for either molecule, sequence homology has provided prospective regions proposed as potential sites of interaction (Linsley et al., 1994a). Despite the lack of conservation, CD80 and CD86 share similar binding avidities to both receptors, although CD86 disassociates more rapidly from CTLA-4 (Linsley et al., 1995a).

CD86 appears to share a similar expression pattern with CD80, being expressed on activated B cells, T-cells, macrophages, and monocytes (Azuma et al., 1993a). Kinetics of expression however are slightly different for the two molecules (Hathcock et al., 1994). CD86 generally appears earlier in an active immune response than CD80, and appears to be constituitively expressed on monocytes (Freeman et al., 1991). While CD80 can appear as late as 24 hr after initial stimulation, CD86 appears early in the response or is found expressed constitutively at low levels on myeloid cells (Hathcock et al., 1994). The two surface proteins evoke similar intracellular responses whether bound to their respective counter receptors on either $CD4^+$ or $CD8^+$ T-cells (Lanier et al., 1995). There does not appear to be any difference in the ability of either molecule to initiate the activation and proliferation of T-cells or to induce CTL activity (Hathcock et al., 1994). Thus, the data suggests that both molecules initiate a similar signal cascade upon binding to CD28 or CTLA-4 respectively (Hathcock et al., 1994). As both molecules also seem to bind these counter receptors with equal kinetics and do not elicit differential effects, it is unclear as to the evolutionary significance of this "two ligand/two receptor" system (Lanier et al., 1995).

CD80 was originally described as a marker for B-cells, and high levels of both CD80 and CD86 are found on B cells stimulated with lipopolysaccharide (LPS), anti-Ig, anti-CD40, concanavalin A (ConA), cAMP, IL-2, and IL-4 (Hathcock et al., 1994). IFNγ and IL-5 have been shown to up-regulate CD86 in murine B-cells, though no data are available from the human system or for CD80 in regards to these immuno-regulators (Azuma et al., 1993a). The kinetics of expression are slightly different in B-cells for each molecule. CD86 is expressed early after stimulation (6 hr) while CD80 is not present until almost 24 hr and does not reach peak expression until after 48 hr (Lenschow et al., 1993). CD80 up-regulation on B-cells also appears to be regulated by MHC class II mediated signaling (Nabavi et al., 1992). Two other surface receptors also appear to be important in CD80 surface expression. Cross-linking of CD40 expressed on the B-cell by Ig or T-cells expressing the counter-receptor, resulted in increased CD80 expression (Azuma et al., 1993b), while cross-linking the Fc receptor down-regulates the expression of both molecules (Barcy et al., 1995).

CD40 and its ligand CD40L have been proposed as a pathway through which CD80 expression is regulated on APC (Page et al., 1994). CD40 is expressed on a variety of cell types, including B cells, monocytes, dendritic cells, fibroblasts and human endothelial cells and can be up-regulated on these cells in the presence of IFNγ (de Boer et al., 1993). The CD40 ligand (CD40L) is expressed on activated CD4$^+$ T-cells. The binding of CD40 by CD40L has been shown to up-regulate CD80 expression in APC, though it does not appear to induce expression in other cell types expressing the receptor, including endothelial cells (Page et al., 1994).

The CD80 and CD86 molecules, though sharing less than 25% amino acid identity, have structural similarities and are thought to be distantly related (Freeman et al., 1993). The homologous residues are concentrated in the Ig-like domains, with few conserved residues in the transmembrane or cytoplasmic domains (June et al. 1995). A family encompassing the B7 genes has been proposed that would, in addition to CD80 and CD86, include butyrophilin (BT), myelin/oligodendrocyte glycoprotein (MOG), the chicken MHC analog, B-G (Linsley et al., 1994b). BT, MOG and B-G are all encoded by the MHC gene complex, which raises a potential evolutionary link between the MHC and the requisite costimulatory molecules (Linsley et al., 1994b).

Resting murine and human T-cells express low levels of CD86 while human and murine T-cells (and T cell clones), activated with anti-CD3, express CD80 and CD86 at appreciable levels (Hathcock et al., 1994). The expression of both CD80 and CD28 on activated T-cells may reflect the ability of T-cells to expand via autocrine costimulation (Azuma et al., 1993b). Interestingly, CD80 has been shown to be up-regulated on HIV infected CD4$^+$ T-cells, with concomitant CD28 down-regulation. It is proposed that this is a possible mechanism of viral transmission when uninfected CD4$^+$ T-cells initiate CD28/CD80 mediated contact with the infected lymphocytes (Haffar et al., 1993).

Human peripheral blood monocytes express low levels of CD80 and high levels of CD86, while exposure to GM-CSF or IFNγ results in the up-regulation of surface expression of both CD80 and CD86 (Barcy et al., 1995). LPS is a strong inducer of CD80 expression in human peripheral blood monocytes (Schmittel et al., 1994). No data is reported on peritoneal macrophages in the human system, but resting murine macrophages express low levels of CD80 and CD86 (Freeman et al., 1991; Hathcock et al. 1994). LPS and IFNγ stimulation of murine macrophages increases surface expression, though IFNγ in combination with interleukin 10 down-regulates both receptors (Ding et al., 1993).

Splenic dendritic cells express low levels of both molecules and Langerhan's cells express low levels of CD86, though culturing tends to increase expression in both cell types (Larsen et al., 1994). In dendritic cells, CD86 appears to be more strongly up-regulated after culturing, appears earlier, and may play the more important role in dendritic cell mediated signaling (Hathcock et al., 1994). Interestingly, though IL-10 has no effect on CD80 expression in dendritic cells, it acts to down-regulate CD86 expression (Buelens et al., 1995). O'Doherty et al. (1993) reported that while initial levels of CD80 were low, upon maturation, dendritic cells present higher levels of CD80. Langerhan's cell expression of CD80 is inhibited by both IL-10 and IFNγ, but GM-CSF exposure can reverse IFNγ inhibition, though not IL-10 inhibition (Ozawa et al., 1996).

In humans and mice specific cytokines have been demonstrated to exert control over CD80 and CD86 expression. IL-4 is a strong inducer of CD86 and to a lesser extent CD80 on B-cells (Stack et al., 1994), while IFNγ increases CD86 expression on a variety of cell types including B-cells monocytes and macrophages (Hathcock et al., 1994). Though IFNγ appears to up-regulate CD80 expression in monocytes, it may act to down-regulate expression in macrophages. IL-10, even in the presence of IFNγ, acts to down-regulate CD80 and CD86 expression on monocytes (Ding et al., 1993). This interaction may be a potential mechanism of a switch from a Th1 response (DTH) to a Th2 response (humoral). IL-10 however, does not influence CD80 expression on dendritic cells (Buelens et al., 1995). This may further reflect a role of these molecules in T helper subset regulation as dendritic cells are thought to be important in the initiation of a type 2 response. IL-7 increases CD80 expression on T-cells though effects on other cell types are undefined (Yssel et al., 1993), while B-cell CD80 expression has been shown to be mediated through the crosslinking of the p75 TNF receptor, and expression can be increased in the presence of IL-4 (Ranheim and Kipps, 1995). Interestingly TNF belongs to the same family of molecules as CD40, another potent initiator of CD80 expression. GM-CSF appears to up-regulate dendritic cells and Langerhan's cell expression of surface CD80, while IFNγ only causes up-regulation of CD86 in these cells (Larsen et al., 1994).

The recognition, binding, and lysis of transformed and virally infected target cells by CD8$^+$ cytotoxic T-lymphocytes (CTL) was long thought to be solely mediated through TCR recognition of foreign peptides expressed in the context of MHC class I (Berke, 1993). Recently it has been determined that a variety of surface molecules expressed by both the CTL and target cells are required for complete interaction to take place (Mescher, 1992). A key player in this interaction is CD80 and its counter receptor CD28. The accessory signal delivered by the B7-CD28 interaction is required by CD8$^+$ small resting lymphocytes to differentiate to a lytic state (Mescher, 1992). Interestingly though, once CTL differentiate, this secondary signal is no longer required for the expression of lytic properties (Hodge et al., 1994).

CTL have long been known to be important mediators of viral immunity. In human immunodeficiency virus (HIV) infected individuals, long term non-progression is associated with high levels of CD8$^+$ memory CTL specific for Gag, Pol and Env and very low copy numbers of HIV DNA and RNA in peripheral blood mononuclear cells (Rinaldo, 1995). Conversely, in individuals in the late stages of infection, memory CTL (mCTL) are seriously decreased (Zanussi et al., 1996). The correlation of these findings supports the idea that mCTL may be a major factor in host control of infection and could play a critical role in establishing protective immunity in naive uninfected individuals (Zanussi et al., 1996). In addition, pathological correlations with HIV infection reflect a potential role for CD80 and CD28 in the progression of the disease.

CD80 has also been proposed to play a role in the development of the pathogenesis of an HIV infection (Haffar et al., 1993). T-cells normally express CD80 but only at low levels and only following activation (Schwartz, 1992). In in vitro studies of HIV infection in allo-stimulated primary T-cell lines, CD28 appears to be down-regulated, and CD80 expression appears to be enhanced along with MHC CII (Haffar et al., 1993). Although a rationale for these events has not been defined, two potentially damaging roles can be hypothesized. The presence of CD80 on the surface in conjunction with class II could result in increased contact between infected T-cells and uninfected CD4$^+$ cells (Haffar et al., 1993). While this interaction could act to enhance the rate of transmission between T-cells, another role could be to increase CTL mediated recognition and killing via the delivery of the secondary signal by the interaction of the CD80 on the infected cell with the CD28 expressed by the CD8$^+$ T cell (Haffar et al., 1993).

This could speed the decline in the CD4+ population linked with the onset of AIDS related illness (Haffar et al., 1993).

In both the murine and human system, the expression of the B7 family of proteins appears to be an important factor in immune recognition of transformed cells (Chen et al., 1992). Although expression has been found in some transformed cells, most tumors do not normally express CD80 or CD86, thus making it unlikely that when a potentially immunogenic tumor antigen is expressed, that full recognition by T-cells will take place (Chen et al., 1993). However, transfection experiments using the CD80 molecule to enhance tumorcidal cytolysis have proven successful (Hodge et al., 1994).

Retroviral and vaccinial based vectors expressing functional CD80 molecule have been used to transfect malignant cells (Li et al., 1994; Hodge et al., 1994). These cells, expressing CD80 in addition to normally poorly recognized tumor antigens, are then reintroduced into the host where it is thought that a cellular immune response is generated against tumor antigens expressed on the malignant cells (Townsend and Allison, 1993). Results from these experiments with some forms of tumors have been surprisingly effective. In many cases the host is able to mount a strong cellular response against the malignancy, and control or eliminate it (Hodge et al., 1994).

Subsequent re-introduction of tumor cells with and without the CD80 surface molecule into the host result in similar levels of anti-tumor immunity (Hodge et al., 1994). Thus, it appears that once memory is established, that the CD80 molecule is not required to sustain the response or to initiate it if re-introduction occurs (Hodge et al., 1994). These experiments demonstrate that the CD80 molecule is an efficient mediator of cellular immunity, and that in specific tumors, cellular responses can be induced to possibly control the malignancy and prevent re-establishment. (Hodge et al., 1994).

Increased CD80 expression can have detrimental effects as is seen in the development of some forms of autoimmunity. It is thought that CD80 in synergy with IL-12 is important in the early development of multiple sclerosis (MS) and results in T cell stimulation and the development of DTH (Windhagen et al., 1995). Experimental autoimmune encephalomyelitis (EAE) can be partially inhibited by the administration of soluble CTLA-4Ig to experimental subjects. The inhibition of demyelination by the blocking of CD28/CD80 interaction, reflects a potential role for this interaction in exacerbating the disease (Arima et al., 1996).

The importance of the CD80 molecule in the progression of an effective immune response is clear. While the cDNA encoding the protein has been isolated in rodents and primates, it has not been isolated outside of these groups. The feline is an important companion animal and potential model of retroviral disease. Cloning of immunological reagents from feline species will provide tools for research into diseases of veterinary importance with potential relevance to disease progression or prevention in other species.

Materials and Methods
Isolation of an Initial Fragment mRNA was extracted from peripheral blood mononuclear cells (PBMC) stimulated for 16 hr with Con A using the RNAzolB RNA extraction reagent (Biotexc, Houston, Tex.). Initially, cDNA was derived from this RNA by a reverse transcriptase (RT) reaction employing oligo dT as the 3' primer. Briefly, the RNA and oligo dT were heated to 75° C. for 3 min to remove secondary structure. The RT, dNTP, buffer and distilled water were then added and the mixture incubated for 1 hr at 42° C. Following this incubation the sample was heated to 95° C. for 5 min to inactivate the RT. Degenerate primers derived from consensus regions within the human and murine CD80 published sequences (GeneBank, Gaithersburg, Mass.) were then employed for the initial amplification of a 344 nucleotide fragment encoding a central region within the constant domain of the gene:

```
                                          (SEQ ID NO: 56)
5' primer B7-2 GGC CCG AGT A(CT)A AGA ACC GGA C;
                                          (SEQ ID NO: 57)
3' primer B7-3 CAG (AT)TT CAG GAT C(CT)T GGG AAA
(CT)TG
```

A hot start polymerase chain reaction (PCR) protocol employing Taq polymerase was used to amplify the product. The reaction mixture, lacking the Taq enzyme, was initially heated to 95° C. for 5 min, in a hot start step, to prevent the formation of primer dimers. The enzyme was added prior to the initiation of the temperature cycle. The PCR reaction was then heated to 95° C. for 30 sec to melt the double stranded DNA. The reaction was then cooled to 42° C. for 30 sec to facilitate the annealing of the degenerate primers. A low annealing temperature was employed to facilitate the binding of primers that were not 100% homologous. The reaction was then heated to 72° C. for 45 sec, the optimal temperature for the Taq polymerase to extend the primer and copy the opposing DNA strand. The temperature cycle was repeated 30 times. Following the 30 cycles, a final extension step of 72° C. for 7 min was used to facilitate extension of any uncompleted products. After visualization on a 1% agarose gel, the product was ligated overnight at 16° C. into the TA cloning vector (InVitrogen, San Diego, Calif.) for sequencing. Two µl of the ligation reaction was used to transform competent InvaF' cells. The transformed bacteria were streaked onto LB plates (50 µg/ml ampicillin) coated with 40 µl of a 50 µg/ml solution of x-gal. The following day, white colonies were selected and inoculated into 5 ml of LB media containing 100 µg/ml of ampicillin and grown overnight at 37° C. with shaking at 225 rpm.

Mini-preps were performed on overnight cultures to determine clones that possessed the plasmid with the correct insert. Plasmid was extracted from the cultures using a standard alkaline lysis procedure, with the DNA being further purified by phenol:chloroform extraction (Maniatis et al., 1982). The DNA was precipitated in 2 volumes of ethanol and then digested with EcoRI. The digests were visualized on a 1% agarose gel to determine colonies with plasmid that contained the proper insert. Plasmid was then purified from positive clones and sequenced using either Sequenase based (USB, Cleveland, Ohio) $S^{35}$ radiolabeled dideoxy terminator sequencing or by fluorescent dye terminator cycle sequencing (Perkin Elmer, Norwalk Conn.). From the sequence of the cDNA, specific 3' and 5' primers were constructed for use in 5' rapid amplification of cDNA ends (RACE) reactions and for derivation of the 3' sequence in conjunction with degenerate primers from the 3' untranslated region (UTR).

Isolation of the 5' Region

The Marathon cDNA amplification protocol (Clonetech, Palo Alto, Calif.) was used to derive the 5' sequence of the gene. mRNA was produced from PBMC stimulated for 12 hr with Con A and concurrently 4 hr with LPS. The mRNA was extracted using the ULTRASPEC RNA extraction reagent (Biotexc, Houston Tex.). cDNA was produced with an anchor oligo dT primer with degenerate nucleotides at the 5' end to facilitate binding of the primer to the 5' most end of the poly A tail. cDNA was then transcribed as previously described. Specific linkers were ligated to the cDNA with T4 DNA ligase. Touchdown PCR was performed on the cDNA with an internal 3' primer specific for the region amplified previously:

B7-284: TTA TAC TAG GGA CAG GGA AG; (SEQ ID NO: 58)

B7-190: AGG CTT TGG AAA ACC TCC AG; (SEQ ID NO: 59)

and an anchor primer complementary to the ligated linker sequence. The parameters for the touchdown PCR reaction using the KlenTaq polymerase mix (Clontech, Palo Alto, Calif.) were: 95° C. for 5 min 1 cycle; 95° C. for 30 sec, 72° C. for 30 sec and 68° C. for 45 sec 5 cycles; 95° C. for 30 sec, 65° C. for 30 sec and 68° C. for 45 sec 5 cycles; 95° C. for 30 sec, 60° C. for 30 sec and 68° C. for 45 sec 25 cycles. 1 µl of this reaction was diluted in 50 µl of water and 5 µl of this dilution were then used in a nested PCR reaction (95° C. for 5 min 1 cycle; 95° C. for 30 sec, 65° C. for 30 sec and 68° C. for 45 sec 30 cycles with KlenTaq polymerase mix) with the linker specific anchor primer and a gene specific 3' primer located 5' of the initial primer.

B7-20: TTG TTA TCG GTG ACG TCA GTG; (SEQ ID NO: 60)

B7-135: CAA TAA CAT CAC CGA AGT CAG G; (SEQ ID NO: 61)

20 µl of each reaction was visualized on a 1.5% agarose gel and the proper fragment cut out of the gel. The cDNA was extracted and purified from the agarose by centrifuging the gel slice through a gel nebulizer and micropure 0.22 µm filter (Amicon, Beverly, Mass.). The purified DNA was then sequenced directly using dye terminator cycle sequencing (Perkin Elmer, Norwalk, Conn.).

Isolation of the 3' Region

The 3' region of the gene was derived by choosing 5 gene specific primers from the 344 nucleotide fragment and the 5' region previously sequenced:

B7-s220: GTC ATG TCT GGC AAA GTA CAA G; (SEQ ID NO: 62)

B7-50: CAC TGA CGT CAC CGA TAA CCA C; (SEQ ID NO: 63)

B7-140: CTG ACT TCG GTG ATG TTA TTG G; (SEQ ID NO: 64)

B7-550: GCC ATC AAC ACA ACA GTT TCC (SEQ ID NO: 65)

B7-620: TAT GAC AAA CAA CCA TAG CTT C; (SEQ ID NO: 66)

Degenerate 3' primers were then chosen from consensus regions of the human and murine CD80 3' UTR.

B7-1281: G(A/G)A AGA (A/T)TG CCT CAT GA(G/T) CC; (SEQ ID NO: 67)

B7-1260: CA(C/T) (A/G)AT CCA ACA TAG GG; (SEQ ID NO: 68)

cDNA was produced from RNA extracted with ULTRASPEC (Biotexc, Houston, Tex.) from PBMC stimulated with Con A and LPS as previously described. The anchored oligo dT was used as the initial 3' primer for RNA transcription to cDNA. Taq polymerase based PCR reactions were performed with this cDNA using the specific 5' primers and degenerate 3' primers (95° C. for 5 min 1 cycle; 95° C. for 30 sec, 42° C. for 30 sec and 72° C. for 45 sec 30 cycles; 72° C. for 7 min). Two rounds of nested reactions were required before a single fragment of the right size was produced. This product was cut from a 1.5% agarose gel, purified as previously described, and sequenced with dye terminator cycle sequencing (Perkin Elmer, Norwalk, Conn.).

From the sequence data of the 5' and 3' regions, primers were constructed that would amplify a region encoding the entire open reading frame of the feline CD80 gene:

B7 START: ATG GGT CAC GCA GCA AAG TGG; (SEQ ID NO: 69)

B7-960: CCT AGT AGA GAA GAG CTA AAG AGG C; (SEQ ID NO: 12)

PBMC cDNA produced previously and known to contain DNA encoding the gene was employed. This PCR reaction (95° C. for 5 min 1 cycle; 95° C. for 30 sec, 42° C. for 30 sec and 72° C. for 45 sec 30 cycles; 72° C. for 7 min) employed KlenTaq DNA polymerase, an enzyme cocktail that retains some 5' exonuclease activity in the hopes of reducing random errors often associated with Taq polymerase. The reaction amplified a 960 base pair (bp) fragment which was cloned into the TA cloning vector (InVitrogen, San Diego, Calif.) and sequenced as previously described. The final sequence of the gene included cDNA from two separate animals. Each base pair of the gene was independently verified in at least three separate sequences derived from individual PCR reactions, to reduce the possibility of errors derived from PCR induced mistakes.

Results

RNA extracted from experimental cat HK5 was used for initial amplification attempts with CD80, however this cat was subsequently terminated and further products were produced in different animals. The initial amplification of HK5 Con A stimulated PBMC RNA resulted in a 344 by product that shared 70% identity with the human CD80 gene. The primers were specific for a region within the center of the coding sequence corresponding to the IgC like domain. Although additional degenerate primers were employed in these initial experiments in order to amplify regions that encoded more of the peptide, only the combination of B7-2 (5') and B7-3 (3') resulted in product of an appropriate size. Later experiments employing these additional degenerate primers with gene specific primers were unsuccessful. Thus, both the 5' and 3' regions had to be derived by employing other methods.

A battery of six new gene specific primers was created from the sequence data obtained from the initial product. (B7-20 5', 135 5', 140 3', 50 3', 284 5', and 190 5'). Initially, the 3' primers were used in 5' RACE PCR procedure somewhat similar to the procedure used to successfully amplify the 5' region of the CD28 molecule. No product was produced employing this method.

The Marathon RACE cDNA amplification system (Clontech, Palo Alto, Calif.), successfully amplified a region that encoded the 5' coding sequence. RNA derived from EK6 Con A stimulated RNA was successfully amplified with this protocol. Initial amplification was carried out with B7-284 and B7-3 and the anchor primer API. This reaction did not produce a defined single band so nested reactions using this product as the template were performed using B7-20 and B7-135 as the nested 3' primers and the anchor primer AP-1 as the 5' primer. A product of the appropriate length was produced from each of these reactions.

Sequence data derived from direct sequencing of the RACE products gave complete identity in the 20 and 135 by regions, respectively, that overlapped the initially sequenced 344 by product. The fragments extended from the known region 5' through the 5' ATG start codon of the feline gene and into the 5' untranslated region. Identity between the 5' coding sequence derived from these products and the 5' region of the human CD80 gene was less than the identity found to exist between the 344 by region of the feline gene and the analogous region within the human sequence. It was observed that a similar lack of homology is found between the human and murine sequences within similar regions. Comparisons of the sequence data from regions outside the coding region showed a further marked decline in conservation (data not shown).

A new panel of degenerate primers encoding the 3' untranslated region were synthesized from consensus regions within the 3' UTR of the human and mouse sequences. These primers successfully amplified cDNA transcribed from RNA isolated from Con A stimulated PBMC from cat ED3. Unlike in the initial amplification procedures, a series of nested reactions had to be run to obtain the final product. Primary PCR reactions using these degenerate primers and anchor primers from within the 344 by fragment and the 5' region did not initially yield clean, identifiable bands. However, nested reactions, using diluted primary product and additional specific 5' primers, resulted in the production of product that encoded the remaining 3' region.

Following sequencing of the 3' product it was found that once outside of the constant region, identity again declined. The distal end of the coding sequence showed very low identity which further declined following the stop codon.

From the 3' sequence, a reverse primer outside of the coding region beginning at nucleotide 960 was constructed. This construct in combination with a primer encompassing the start codon amplified a product of the anticipated size. Sequencing of the final product demonstrated that each of the previously determined regions did in fact overlap and this fragment provided a contiguous and complete sequence of the feline CD80 gene.

For amplification of the final product, samples were amplified from the RNA from Con A stimulated PBMC of animals ED3 and EK6. At least two products from each animal were completely sequenced and each nucleic acid site was checked and confirmed with at least three different correctly reading sequences. The product from animal EK6 was then cloned into the TA cloning vector for future reference and manipulation.

The 960 nucleotide fragment includes the start codon at position 1, the stop codon located at nucleotide 888, and an additional 72 nucleotides of the 3' untranslated region. From the products produced and sequenced to encompass the entire fragment, additional 5' and 3' regions were sequenced (data not shown). The sequencing of the region upstream of the 5' start codon from 5' RACE products demonstrated that the ATG listed as position 1-3 was the first in frame methionine site and conformed to a similar position in the murine and human sequences. The stop codon located at position 888 also conformed to a similar locale in the previously sequenced genes. Alignment of the sequence demonstrated a 77% and a 62% identity, respectively, with the published human and murine CD80 nucleic acid sequences. Homology with the other primate and rodent sequences is comparable to levels found in human and mice, respectively. Identity with the CD86 gene from each species was less than 25%.

Using the MacVector DNA analysis software (IBI, Rochester, N.Y.) the nucleic acid sequence was translated into an amino acid sequence. Translation yielded a 292 amino acid peptide, similar in length, though not identical, to both the murine and human proteins. The signal peptide is proposed to extend from positions 1 through 25. The extracellular region of the molecule is composed of the 115 base IgSF variable-like domain which extends through residue 139 and the 100 base IgSF constant-like domain which extends to approximately residue 240. The membrane spanning domain from residue 241-271 is followed by a short cytoplasmic tail of 21 residues. As in the human molecule, the feline polypeptide contains 8 potential N-linked glycosylation sites though the domains are not identically localized. Homology between the feline, human and murine peptides is significantly less than the identity observed in the nucleic acid sequences (Table 1).

TABLE 1

Comparison of feline with murine and human CD80 for sequence homology.

| Species | Percent homology with the feline sequence: | |
|---------|---------|---------|
|  | Nucleotide | Amino Acid |
| Human | 77% | 59% |
| Mouse | 62% | 46% |

An alignment of the proposed peptide sequence of feline CD80 with the proposed human protein demonstrates that by far the majority of the homology between the two molecules occurs in the constant region (residues 140-240). There is low homology between the peptides in the signal sequence, and this lack of identity extends through the IgV like domain. As mentioned, conservation is strong through the constant domain, however this identity is not contiguous and very little homology is found between the transmembrane domain and the intracellular cytoplasmic tail of the feline peptide and analogous regions in the human molecule.

Alignment of the feline, human, and murine CD80 genes with the murine and human CD86 genes reveals that although there is only limited overall homology between the two B7 family members, residues that have been deemed to be indicative of the B7 gene family are retained by the feline peptide. These molecules include residues thought to be involved in folding and a proposed binding region.

While homology between the human and the feline CD80 sequence is not as great as the identity between the two CD28 molecules, a comparison of the proposed hydrophilicity plots demonstrates that while there are a variety of changes in the specific amino acid sequence, these changes are frequently homologous and potentially do not alter the surface characteristics of the peptide.

Discussion

The nucleotide identities between feline and human and feline and murine CD80 are moderate, though the degree of nucleotide homology is not translated to the peptide. It appears that while the genetic code is degenerate, and in some molecules (i.e. CD28) differences between nucleotide sequences do not significantly alter the peptide, with CD80 conservation of overall amino acid integrity is not as critical, and thus evolutionary alterations in the molecule across species are more permissible.

Although the overall nucleic acid sequences share a relatively moderate degree of identity, there were complications in obtaining a full length sequence. The initial CD80 product was obtained from the constant region of the molecule, an area that demonstrates the highest degree of conservation in the cDNA from the species cloned. Primers that recognized the region and successfully amplified a product were readily produced, resulting in the 344 nucleotide fragment encompassing the well conserved IgC region. Unfortunately, due to the lack of homology in the signal peptide and in the cytoplasmic domain and 3' UTR, more complicated measures were required to isolate the sequence of these regions. The presence of sequence data from the central region however, provided a strong anchor point from which the rest of the molecule could be elucidated. Feline CD80 is a fine example of how, by obtaining a short stretch of a molecule, and using RACE methods and degenerate primers in combination with anchor primers from the sequenced region that a full length sequence can be readily obtained.

Comparison of the putative amino acid sequences of these cloned CD80 molecules demonstrates a lack of overall homology. The murine and human polypeptides demonstrated less than 50% homology at the amino acid level. This is comparable to the 59% identity between feline and human and 46% identity between the feline and murine polypeptides and perhaps reflects the evolutionary proximity of the species. A comparison of the predicted hydrophilicities of the feline and human residues, which demonstrates amino acids that would potentially be exposed or recessed due to their relative hydrophilicity, reveals that while at the amino acid level, the specific amino acids may not be retained, the changes appear to be relatively conserved. This demonstrates the potential retention of the hydrophilic/hydrophobic character of the molecule that thus may reflect overall, a structurally similar polypeptide. The surface protein appears to have particular amino acids that may be directly involved in binding, and other structural amino acids that need only retain a structure that will allow interaction with the binding region to take place.

While there is divergence in the identity of the amino acid residues in the CD80 molecules from the primate, rodent and feline species, there is a retention of the characteristics of the IgSF. The feline CD80 molecule consists of an amino terminal IgC-like domain and a IgV-like domain proximal to the membrane associated region. As with the conservation between murine and human CD80, identities are far greater between the constant regions than between the variable regions (Freeman et al., 1989). Overall, conservation in the variable domain is just over 50% while that found in the constant region is over 70%, with the short stretch from residues 164-198 (the region from which the initial 344 nucleotide fragment was obtained) having far greater identity. This central region of 56 amino acids (residues 165-221) within the constant region demonstrates 87% homology between the human and feline sequences, with an extended region of 28 amino acids (residues 171-198) in which only a single difference exists. The region in the feline also demonstrates significant homology to the corresponding residues in the murine polypeptide. The hydrophilic nature of the amino acids within this region demonstrate a high likelihood of surface expression and due to the level of cross species conservation, a potential involvement in ligand/receptor interaction. It has been proposed that the IgC portion of the molecule is directly involved in the presentation of the binding domain for receptor ligand interaction (Peach et al., 1995). It has been experimentally determined however, that both the variable and constant motifs are required for effective binding (Peach et al., 1995). The concentration of homologous residues in the IgC region of the extracellular domains, along with the high level of divergence within the transmembrane and cytoplasmic domains, appear to further confirm the role of CD80 as a ligand rather than having a signaling capacity.

As with human and murine CD80, the feline molecule is highly glycosylated. The carbohydrate residues are not thought to be involved directly in binding, but may help to increase the solubility of the extracellular portion of the molecule (Peach et al., 1995). Of the eight potential sites found in the human peptide, seven are located in identical positions in the feline protein. The site located at amino acid residue 39 in the feline molecule is not replicated in human CD80, though there is a site at residue 232 that is not found in the feline protein (Freedman et al., 1987). Seven sites are found in the murine molecule with only two being in identical locations, though they are generally found in the same areas of the molecule as the feline and human peptides (Freeman et al., 1989). The similarity in the retained number and locations of glycosylation sites appears to reflect the importance of the motifs in the function of the molecule.

There are a wide variety of potential applications of the feline CD80 molecule. The molecule as has been previously discussed is critical to the proper development of a mature T cell response. Monitoring expression of the gene at both the RNA and protein levels will help to establish the means in which the feline immune system is dealing with infection. How this system deals with specific pathogens, when combined with observations obtained from research in other model systems, may provide further insight into the human immune response. Further, as a significant companion animal, insight into how the feline system may be beneficially manipulated may provide veterinary medicine with enhanced options.

An important future application proposed for the CD80 molecule in other species has been the induction of tumor specific immunity by the introduction of the CD80 gene into transformed cells, with reintroduction into the host to elicit CTL based tumor immunity (Townsend and Allison, 1993). As previously discussed, it is thought that as a result of surface expression of CD80 by the tumor cells, that a specific CTL response is mounted against the malignancy (Hodge et al., 1994). Further, a memory population of $CD8^+$ T-cells is established in the host (Hodge et al., 1994). While this technology has been concentrated on tumor immunity, by analogy, it may also be applicable in establishing anti-viral immunity.

As discussed previously, long term non-progression in acquired immune deficiency syndrome is thought to be mediated through the initial establishment of a strong anti-HIV CTL response (Landay et al., 1994). It appears that those individuals able to maintain an asymptomatic status for the longest time after infection are able to mount and maintain a strong CTL response directed against the virus.

While traditionally vaccines have been directed at establishing a humoral response, if a vaccine could induce the development of an anti-HIV/FIV mCTL population, this population might provide protection similar to that found in long term non-progressors. In naive individuals, introduction of a gene based vaccine that combined FIV proteins with the CD80 peptide could result in the surface expression of the costimulatory molecule in combination with MHC CI presentation of FIV epitopes. If successful, this should result in the expansion of a FIV specific mCTL population in the naive individual. On subsequent exposure to virulent virus, the vaccinated individual would be primed to mount a response against cells that become infected with the virus, eliminating them before the virus has the opportunity to establish itself and begin its destruction of the components of the immune system.

Example 6

Cloning and Sequencing of Feline CD28 cDNA
Introduction

CD28 is a surface glycoprotein normally expressed as a homodimer composed of identical disulfide linked 44 kDa subunits. It is a member of the immunoglobulin supergene family, and is characterized by a single extracellular V region, a transmembrane domain and a short intracellular tail (Aruffo and Seed, 1987). Although the molecule is glycosylated, the moieties do not appear to play a role in binding and are hypothesized to increase the solubility of the extracellular domain (Peach et al., 1994). cDNA encoding the human, rat, mouse, and rabbit peptides and an analogous molecule in the chicken have been cloned and sequenced (Linsley et al., 1995a).

CD28 is found on most $CD4^+$ $CD8^+$ thymocytes and peripheral $CD4^+$ and $CD8^+$ T-cells with increased expression resulting from αντι-XΔ3, PHA and PMA stimulation, and suppression resulting from anti-CD28 binding (Linsley et al., 1993b) It was determined soon after its discovery that CD28 played an important role in regulating $CD4^+$ and $CD8^+$ T-cell activation (June et al., 1990). In addition to augmenting T-cell activation and proliferation, it has been further demonstrated that delivery of this secondary signal also acts to induce cytolytic activities in CTL (Azuma et al., 1993c).

CD28 is expressed early in the maturation of T-cells. While immature $CD3^{31}$ cells are normally $CD28^-$, intermediate $CD4^+$ $CD8^+$ cells express low levels, and $CD4^+$ or $CD8^+$ $CD3^+$ thymocytes express CD28 at high levels (Turka et al., 1991). After maturation, the receptor is found on almost all $CD4^+$ and over half of all $CD8^+$ T-cells in humans (Turka et al., 1991) and on nearly 100% of murine T-cells (June et al., 1990). The molecule is not expressed at constant levels on the cell surface (Turka et al., 1990). Following T cell activation, surface expression increases, while binding of the molecule by its ligand or specific mAb results in the down-regulation of the gene at both the mRNA and protein level in activated cells (Linsley et al., 1993a). Although found largely on lymphocytes of the T-cell lineage, CD28 has been reported on plasmocytomas from bone marrow biopsies (Kozber et al., 1987) and expressed by cultures of a natural killer-like leukemic cell line (Azuma et al., 1992).

CD28 shares a degree of structural homology with the other B7 receptor CTLA-4, and the two are grouped as a subfamily within the IgSF group (Linsley et al., 1995a). The two molecules have an extracellular IgV region, a single membrane spanning domain, and a short cytoplasmic signaling domain (Aruffo et al., 1987). Although overall homology between the two molecules is only about 31%, there are short regions and specific residues that are completely conserved between the two molecules, reflecting a potentially important role for these motifs in B7 recognition and structural integrity (Leung and Linsley, 1994). The MYPPPY motif, a six residue region, is retained in all of the isolated members of the CD28/CTLA-4 family (Peach et al., 1994). It maps to the CD3-like loop region within the molecules, and when altered by mutation, results in reduced binding avidity in both CD28 and CTLA-4 (Peach et al., 1994). This region has been proposed as the potential ligand binding site on the CD28 and CTLA-4 proteins, but it has not been determined if this region is the actual binding site for B7 or if it provides the structural motifs indirectly required for binding to take place (Peach et al., 1994). Although there are conserved residues shared between CD28 and CTLA-4, CTLA-4 binds both CD80 and CD86 with a higher avidity than CD28 (Ellis et al., 1996). Thus, while CTLA-4 is expressed at only 2-3% of the level of CD28 on activated T-cells it binds with a 20 fold higher avidity in vitro (Linsley et al., 1995b).

Although CTLA-4 and CD28 molecules are evolutionary related, sharing common ligands, their function and signaling capacities appear to be unrelated (Balazano et al., 1992). Comparison of the signaling regions from each molecule does not reflect a high identity and suggests that different signaling pathways are initiated by each molecule (Hutchcroft and Bierer, 1996).

While CD28 is expressed in resting T-cells and is up-regulated initially in response to activation, CTLA-4 expression peaks 48 hr after activation and returns to baseline levels by 96 hr post-activation (Linsley et al., 1992a). The expression of CTLA-4 seems to correspond to CD28 down-regulation (Lindsten et al., 1993). Additionally, signaling pathways mediated through ligand binding of the CD28 molecule appear to be important in up-regulating the expression of CTLA-4 (Linsley et al., 1993a). T-cells that are $CD28^-$ do not express appreciable CTLA-4 in response to stimulation with PMA or calcium ionophore (Lindsten et al., 1993).

A complete sequence of the events of CD28 mediated signaling remains incompletely defined, though a hypothesized cascade has been established (Hutchcroft and Bierer, 1996). It has been suggested that CD28 signaling involves the mobilization of intracellular $Ca^+$ metabolism of phosphotidylinositol and the induction of protein tyrosine phosphorylation (Hutchcroft and Bierer, 1996).

The cytoplasmic tail of the CD28 molecule has defined motifs that are thought to be involved in intracellular signaling following crosslinking by CD80 or CD86 (June et al., 1994). The 41 amino acid intra-cytoplasmic region has no definable enzymatic activity, does not contain intracellular tyrosine activation motifs (like the TCR) nor cysteine residues for the binding of Src family cytoplasmic tyrosine kinases (June et al., 1994). However, several potential phosphorylation sites are conserved amongst the isolated sequences (Hutchcroft and Bierer, 1996). Intracellular enzymatic activity and protein-protein interactions are often regulated through differential protein phosphorylation, though enzymes responsible for this activity by CD28 have not been elucidated (Lu et al., 1992). A consensus site, YMXM, located in the cytoplasmic tail, is a proposed site of Src homology 2 phospho-tyrosine-binding domain (SH2 domain) dependent phosphatidylinositol 3-kinase (PI3 kinase) binding (Prasad et al., 1995). Although this is one potential signaling pathway of CD28, it has been demonstrated that PI3 kinase activity does not correlate with IL-2 activity, and as an increase in IL-2 production is a primary consequence of CD28 signaling, it is felt that other pathways contribute to the activation resulting from intracellular signaling (June et al., 1994).

While the role of these events is not completely understood, CD28 costimulation leads to an increased production of cytokines by the T-cell. In $CD28^+$ T-cells activated with anti-CD3 or PHA, anti-CD28 increases steady state RNA levels of a series of cytokines, including IL-1, IL-2, IL-3, IL-4, tumor necrosis factor (TNFα), lymphotoxin, IFNγ, and granulocyte-monocyte colony stimulating factor (GM-CSF), as well as the IL-2 receptor (Lenschow et al., 1996). The increase in steady state mRNA is due to both stabilization of the transcripts and an increase in transcription (Hutchcroft and Bierer, 1996).

Although CD28 costimulation was first documented in $CD4^+$ T cell clones (Martin et al., 1986), CD28 is now known to play a role in the activation of many cell types. Costimulation of this pathway has been shown to regulate IFNγ production, a Th1 type cytokine, and IL-4 production, a Th2 type cytokine, in subpopulations of naive CD4+ T-cells (Seder et al., 1994). The CD28 costimulatory pathway is also important in the activation of CD8+ CTL, although it does not appear to be necessary for the effector phase of CTL mediated killing (Hodge et al., 1994). Interestingly, CD28 also appears to play a role in HIV infection. In lymphocytes cultured from some individuals positive for the virus, binding of CD28 with a monoclonal antibody can result in an increase in HIV production (Asjo et al., 1993).

In primates and rodents, the secondary signal delivered by the binding of CD80 with CD28 clearly has a demonstrable role in the initial activation of T-cells (Aruffo and Seed, 1987). Recent data suggests however that a major effect of the interaction may be to sustain proliferation by preventing the onset of apoptosis (Lenschow et al., 1996). Resting T-cells in the $G_0$ phase of growth can become activated through the formation of the TCR complex but are unable to proliferate or secrete IL-2 in the absence of CD28 crosslinking, a state termed clonal anergy (Linsley et al., 1991a). Mature T-cells can become activated solely through the binding of the TCR with the MHC on an APC, but this eventually leads to activation induced cell death through apoptosis (Radvanyi et al., 1996). While other secondary interactions (i.e. ICAM-1 costimulation) can provide auxiliary proliferative signals, it appears that CD28 mediated costimulation is unique in preventing the subsequent onset of clonal anergy and apoptosis (Linsley et al., 1993a). It has been shown that CD28 may play a role in regulating genes known to play an important role in the protection of T-lymphocytes from apoptosis (Boise et al., 1995). A sustained increase in bcl-$x_l$ expression is observed in T-cells costimulated by CD28 crosslinking (Boise et al., 1995). It is felt that CD28 costimulation may act to stabilize bcl-$x_l$ mRNA, with expression of the encoded polypeptide preventing the onset of apoptosis (Radvanyi et al., 1996).

CD28 ligation has been demonstrated to have a role in enhancing the production of a variety of both T helper type 1 and type 2 cytokines (Lenschow et al., 1996). There also appears to be a role for this interaction in the development of the specific T helper subsets. Naive CD4+ T-cells will normally develop a Th1 phenotype if activated in the absence of CD28/CD80 mediated signaling (Lenschow et al., 1996). This may be an indirect role as IL-4 production could be induced by the exogenous addition of IL-2, and the role of CD28 signaling in the production of IL-2 has already been discussed (Seder et al., 1994). Additional studies involving CD28 knockout mice further support a role for the receptor in the development of Th2 cells.

CD28$^{-/-}$ mice were developed by Shaninian and coworkers with the intent of establishing how an animal adapts to infection in the absence of the CD28 derived secondary signal (Shahinian, et al., 1993). The gene was disrupted in embryonic stem cells by partial replacement of the second exon with a neomycin resistance gene (Shahinian et al., 1993). PBMC from mice homozygous for the knockout were found to express no CD28 on their T-cells while heterozygotes CD28$^{-/+}$ were found to have a reduced surface expression of the molecule (Shahinian et al., 1993). Mitogen stimulation of T-cells derived from the CD28$^{-/-}$ mice had reduced T cell proliferation and production of cytokines that could only be partially restored by exogenous IL-2 (Shahinian et al., 1993). It has been demonstrated that highly purified T-cells are not activated by lectins in the absence of APC (Unanue, 1984). With this knockout strain, it was demonstrated that the CD28/CD80 interaction is required for the mitogenicity of T cell lectins (Shahinian et al., 1993). The interaction was also found to be important in the mediation of isotype switches by B cells in response to antigen (Shahinian et al., 1993). Unlike with the CD80 knockouts, a demonstrable role for CD28 could be determined using gene knockout technology. A CTLA-4 knockout mouse has yet to be reported, but a mouse transgenic for the overproduction of CTLA-4 Ig has been studied (Lane et al., 1994). As might be anticipated, this strain has some phenotypic characteristics that are similar to CD28 deficient strains (Lane et al., 1994). While isolated T-cells produce normal amounts of IFNγ, appreciably less IL-4 was made upon stimulation (Ronchese et al., 1994). This lead to the inability of B cells to mount or maintain a proper humoral response (Ronchese et al., 1994). Though there are many proposed pathways of Th1 and Th2 differentiation, the CD28/B7 interaction has demonstrable influence on T cell subset differentiation.

Interleukin-2 mRNA stabilization maybe a critical function of CD28 crosslinking, but a range of other cytokines have been shown to be directly or indirectly affected by this interaction (Linsley et al., 1991a). The inflammatory mediators IL-1α, IL-6 and TNFα are produced in memory T cell populations in response to CD28 signaling, while in naive populations only IL-1α is produced (Cerdan et al., 1991; van Kooten et al., 1991). IL-4 expression is also regulated through the CD28 signaling pathway (Seder et al., 1994). IL-5, IL-10 and IL-13, other important mediators of humoral response, are also up-regulated by the interaction (deWaal Malefyt et al., 1993, Minty et al., 1993) In addition colony stimulating and growth factors including GM-CSF, CSF-1 and IL-3 and chemotactic factors including IL-8 are all up-regulated with the signal delivered by CD28 (Harlan et al., 1995).

While the potential use of CD80 in the induction of cancer immunity has been previously discussed, there are a range of other proposed clinical uses for CD28 and CD80. Prevention of the interaction between CD28 and CD80 has been demonstrated in rodent model systems to facilitate the prevention or treatment of some autoimmune disorders, in the prevention of the onset of organ rejection or graft versus host disease, and in the prevention of cytokine release associated with sepsis (Harlan et al., 1995; Nickoloff et al., 1993; Thomas et al., 1994; Zhou, et al., 1994). The addition of CTLA-4 Ig to block CD28/CD80 interaction in mice can prevent lupus like symptoms in NZB/NZW mice, and can partially protect against lethal EAE and lethal nephritis in rats (Harlan et al., 1995). While this form of immunotherapy for autoimmune disorders in humans has not been attempted, it has been observed in humans that in psoriasis and rheumatoid arthritis, biopsies demonstrate CD80 expression while in normal biopsies this expression is absent (Nickoloff et al., 1993; Thomas et al., 1994). In bone marrow and organ transplants in mice and in vitro human experiments, the addition of CTLA-4 Ig and the prevention of the CD28/B7 interaction can result in at least partial protection from organ rejection, the prevention of GVHD or the induction of antigen specific tolerance (Harlan et al., 1995). And finally, the cytokine release and onset of sepsis that can lead to septic shock or septicemia can be prevented in mice by the in vivo administration of CTLA-4 Ig (Zhou, et al., 1994). The manipulation of the CD28/CD80 interaction provides a more thorough understanding of T cell costimulation and provides insight into establishing solutions to a variety of problems.

Materials and Methods
Isolation of an Initial Fragment of CD28 mRNA was extracted from HK5 peripheral blood lymphocytes stimulated for 16 hr with Con A using the RNAzolB RNA extraction reagent (Biotexc, Houston, Tex.). Initially cDNA was derived from this RNA by a reverse transcriptase (RT) reaction employing oligo dT as the 3' primer. Briefly, the RNA, and oligo dT were heated to 75° C. for 3 min to remove secondary structure. The RT, dNTP, buffer and distilled water were then added and the mixture incubated for 1 hr at 42° C. Following this incubation, the sample was heated to 95° C. for 5 min to inactivate the RT. Degenerate primers derived from consensus regions found within the human, murine and rabbit CD28 published nucleic acid sequences (GeneBank, Bethesda, Md.) were then employed for the initial amplification of a 673 nucleotide fragment encoding the majority of the open reading frame.

```
                                               (SEQ ID NO: 70)
    CD28-113: CAA CCT TAG CTG CAA GTA CAC;

(SEQ ID NO: 71)
    CD28-768: GGC TTC TGG ATA GGG ATA GG;
```

A hot start PCR protocol employing Taq polymerase was used to amplify the product (95° C. for 5 min 1 cycle; 95° C. for 30 sec, 48° C. for 30 sec and 72° C. for 45 sec, 30 cycles; 72° C. for 7 min, 1 cycle). The fragment was then visualized on a 1% agarose gel and ligated into the TA cloning vector (InVitrogen, San Diego, Calif.) and sequenced as previously described. From the sequence of the cDNA, specific 3' primers were derived and synthesized for use in 5' RACE reactions.

```
                                               (SEQ ID NO: 72)
    CD28190: CGG AGG TAG AAT TGC ACT GTC C;

(SEQ ID NO: 73)
    CD28 239: ATT TTG CAG AAG TAA ATA TCC;
```

Isolation of the 5' Region

A modified GIBCO 5' RACE protocol (Gibco BRL, Gaithersburg, Md.) was employed to obtain the remaining 5' sequence of the feline CD28 molecule. RNA was extracted from 16 hr Con A stimulated PBMC. A 3' gene specific primer was employed for first strand cDNA synthesis. The RNA and the primer were heated to 75° C. for 5 min prior to the addition of the other RT reagents. Following the denaturation, the mixture was cooled to 4° C. and reaction buffer, magnesium chloride, dNTP, DTT and SuperScript RT (Gibco BRL, Gaithersburg, Md.) were added. The RT mixture was incubated at 42° C. for 30 min and then heated to 70° C. for 15 min to denature the RT. An RNase cocktail was then added and the reaction incubated at 55° C. for 10 min to removal residual RNA and prevent incorrect terminal transferase (TdT) extension. The cDNA was then purified over a GlassMax (Gibco BRL, Gaithersburg, Md.) spin column to remove unincorporated dNTP and primer. Purified cDNA eluted from the column was then tailed with TdT. TdT was employed to add a 20-30 nucleotide dC tail to the cDNA. The enzyme was added to a mixture of purified cDNA, magnesium chloride, reaction buffer, and dCTP following denaturation of the cDNA at 95° C. for 3 min. The reaction was incubated at 37° C. for 10 min and the enzyme was then heat inactivated at 70° C. for an additional 10 min. The tailed cDNA was amplified in a Taq polymerase based hot start PCR reaction (95° C. for 5 min; 95° C. for 30 sec, 55° C. for 30 sec 72° C. for 45 sec, 35 cycles; 72° C. for 7 min). The primers for this reaction included a 3' primer located 5' of the cDNA synthesis primer, and an anchor primer specific for the dC linker and composed largely of dG with a few dI residues. One µl of this reaction was diluted in 50 µl of water and 5 µl of this dilution were then used in a nested PCR reaction (95° C. for 5 min 1 cycle; 95° C. for 30 sec, 55° C. for 30 sec and 72° C. for 45 sec 30 cycles with KlenTaq polymerase mix) with the dG/dI 5' anchor primer and an additional upstream gene specific 3' primer. Thirty µl of the nested reaction was then visualized on a 1.5% agarose gel, and the proper fragment extracted from the gel. The cDNA was purified as previously described with the Amicon gel nebulizer and micropure filter (Amicon, Beverly, Mass.). The purified cDNA sample was sequenced through dye terminator cycle sequencing (Perkin Elmer, Norwalk, Conn.). From the fragments completed, a consensus sequence was derived. From the sequence, a primer pair was synthesized that encompassed the entire open reading frame of the feline CD28 gene:

```
                                               (SEQ ID NO: 13)
    feCD28 5': CGC GGA TCC ACC GGT AGC ACA ATG ATC CTC
    AGG;

(SEQ ID NO: 14)
    feCD28 3': CGC GGA TCC TCT GGA TAG GGT CC ATG
    TCA G;
```

Using these primers, a cDNA molecule including the entire coding region was amplified from Con A stimulated EK6 and ED3 PBMC derived cDNA. This PBMC cDNA was produced previously and had been demonstrated to contain RNA encoding the gene. This PCR reaction (95° C. for 5 min 1 cycle; 95° C. for 30 sec, 42° C. for 30 sec and 72° C. for 45 sec 30 cycles; 72° C. for 7 min) using KlenTaq DNA polymerase in the hopes of reducing random errors often associated with Taq polymerase, produced a 754 bp fragment which was cloned into the TA cloning vector and sequenced as previously described. As with the CD80 molecule, each nucleotide site was confirmed by at least three independently derived sequences.

Results

Degenerate primers chosen from consensus regions within the murine, human and rabbit CD28 cDNA sequence were employed in a PCR reaction and successfully yielded a product that encompassed almost all of the feline coding sequence. Due to the higher degree of conservation found in the CD28 molecule, initial amplification using degenerate primers yielded virtually the entire molecule. As opposed to the feline CD80 molecule in which only a small central fragment was initially produced, only the 5' most 113 nucleotides were lacking from the open reading frame of the CD28 cDNA. This sequence initial fragment shared an 86% homology with the analogous region within human sequence, a 86% identity with the rabbit cDNA and a 79% homology with the murine coding sequence.

The 5' ATG and the additional 110 nucleotides as well as some upstream 5' sequence was isolated using 5' RACE PCR (Gibco, Gaithersburg, Mass.). cDNA transcribed from EK6 Con A stimulated PBMC was used in the tailing reactions. With this material, amplification with primer CD28-786 and the anchor primer dG produced little definable material.

Although no identifiable bands were amplified with the primer combination dG/CD-786, diluted cDNA from this reaction was amplified using the nested CD28 primers, CD28-182 and CD28-239. A visible band was present at approximately 600 bp. This product when isolated from an agarose gel and sequenced contained the 5' upstream sequence including and continuing through the start codon.

From the sequence of these products a 5' primer was derived that included the start codon. This primer, in combination with the 3' construct, were used to amplify cDNA from RNA extracted from EK6 and ED3 Con A stimulated PBMC producing a 754 bp product.

At least two of the products from each animal were completely sequenced and each nucleic acid site was checked and confirmed with at least 3 independent correctly reading sequences. Following sequencing the full length product was sequenced from the TA cloning vector to insure a consistent and reproducible product.

Within the final 685 bp fragment encoding the entire open reading frame, the 5' ATG was located at position 1, the stop codon was found at position 664-666, with an additional 19 nucleotides in the 3' UTR. As with the feline CD80 molecule, the 5' position of the ATG codon was confirmed through sequencing of 5' RACE PCR products.

The feline CD28 gene, once sequenced, demonstrated an overall identity that was closest to the rabbit and human sequences. The homology with the murine cDNA was still strong while identity with the chicken sequence was more divergent, though comparable to that seen between the chicken sequence and other mammalian genes (Table 2).

TABLE 2

Comparison of feline with murine, human, chicken and rabbit CD28 for sequencehomology.

| Species | Percent homology with the feline sequence: | |
|---|---|---|
| | Amino Acid | Nucleotide |
| Human | 85% | 82% |
| Mouse | 77% | 74% |
| Rabbit | 84% | 84% |
| Chicken | 59% | 50% |

An amino acid peptide sequence was derived from the nucleic acid sequence as previously described. Identity with the derived peptide sequences of the other published genes was comparable to the identity at the nucleotide level. The signal sequence of the peptide extends from the 5' methionine through residue 19. It appears that in the feline molecule, as in the other cloned CD28 polypeptides, that the single extracellular IgSF variable-like domain extends from residue 19-153. The hydrophobic membrane spanning domain extends for the next 27 residues, and is followed by the 41 amino acid cytoplasmic tail. As with the human CD28 molecule, the feline polypeptide has 5 potential N-linked glycosylation sites.

Comparison of the predicted amino acid sequence of feline and human CD28 proteins demonstrated regions of homology with some differences. The majority of changes can be found in the transmembrane domain and in the signal sequence and $NH_3$ terminal domain. The highest degree of homology is found in the central IgSF V-like domain and in the cytoplasmic tail.

Comparisons of the feline CD28 molecule with the predicted amino acid sequences of the human and murine members of the CD28/CTLA-4 family demonstrate that while there is only a 25% overall homology between the members of this group, that specific regions and residues are maintained. The MYPPPY motif is retained by all of the members of this group. There appear to be additional residues retained in the feline molecule that are predicted to be important for structural integrity including a number of conserved cysteine residues.

The cytoplasmic domain of the feline CD28 molecule is moderately conserved with other published sequences especially the mammalian sequences. A variety of intracellular signaling pathways are proposed to be mediated as a result of the crosslinking of the extracellular portion of the receptor (Hutchcroft and Bierer, 1995).

Hydrophilicity plots of the predicted amino acid sequence of feline CD28 when compared to similar plots of the human polypeptide, further demonstrate the probability that each protein retains a similar structural integrity. Where changes in the amino acid sequence occur however, there do not appear to be significant changes in the hydrophilicity of the molecule, which reflects that changes in the amino acid sequence are largely homologous. Of note is the hydrophobic membrane spanning domain in which the feline and human peptides only share 75% homology, yet have very similar hydrophilicity profiles.

Discussion

The sequences of the cloned CD28 molecules all demonstrated a moderate level of evolutionary conservation. It can be hypothesized that the role of the molecule in the activation and mediation of T cell mediated immunity is retained in a variety of higher vertebrates, from fowl, through rodents and carnivores, and including higher primates.

Comparison of the putative amino acid sequences of each of the molecules shows moderate homology in portions of the extracellular domain proposed to be involved in ligand binding and in intracellular regions proposed to promote intracellular signaling. Overall, the highest degree of homology is found in the region surrounding the proposed ligand binding site, MYPPPY, located in the IgV domain from residues 118-123 in the feline polypeptide.

The proposed signal sequence of the peptide extends from the 5' methionine through residue 19 (Aruffo et al., 1987). Monomeric CD28 is composed of a single extracellular IgSF variable-like domain, which extends from residue 19-153 (Aruffo et al., 1987). The hydrophobic membrane spanning domain extends for the next 27 residues, and is followed by a 41 amino acid cytoplasmic tail (Aruffo et al., 1987). The feline protein has 5 potential N-linked glycosylation sites in identical positions as those found in the human protein. Interestingly, the glycosylation site located at residue 105 in the feline protein is NQS while in the human sequence it is NQT. This amino acid divergence further reflects that while there are sequence changes between the molecules, the overall structural characteristics are retained.

As might be expected due to the level of homology shared by the protein, comparison of the hydrophilicity plots of feline and human CD28 demonstrate that the molecules share potentially similar conformational patterns. However, it also reveals that when there is a residue that it is altered, the change is generally homologous.

While the transmembrane domain is the area of, the molecule with the lowest degree of conservation, simply retaining its required hydrophobic character, the cytoplasmic domain of the feline CD28 molecule is moderately conserved with other published sequences. A variety of intracellular signaling pathways are proposed to be mediated through the crosslinking of the extracellular portion of the receptor and although the intracellular portion of the CD28 polypeptide does not have intrinsic enzymatic activity, rather, ligand binding results in the activation of intracellular effector molecules (Aruffo et al., 1987). There are four conserved tyrosine residues ($Y^{173}$, $Y^{188}$, $Y^{191}$ and $Y^{200}$) that have been proposed as potential sites of tyrosine phosphorylation (Lu et al., 1992). Additionally, the MNM sequence beginning at residue 193 of the feline molecule is proposed as a site of an SH2 domain in the human and murine proteins (Prasad et al., 1995). A potential site of phosphorylation by protein kinase C is retained at $S^{185}$, while $T^{202}$ may be a site of Erk1 or Erk2 proline directed serine/threonine kinase activity (Hutchcroft and Bierer, 1996). As discussed previously, the signaling function of the CD28 receptor is multi-faceted, so it is not surprising that the cytoplasmic tail of the peptide has multiple potential signaling mediators.

The future applications of the feline CD28 molecule should include developing tools to detect surface expression of the receptor and monitoring CD28 expression following infections with viruses such as FIV. If tools for protein detection can be combined with existing methods of message detection, valuable information about the levels of expression during the course of infection may be determined. A further correlation of CD28 expression patterns during the course of chronic FIV infection will act to exemplify the feline system as a proper model of HIV infection in humans, and may lead to more definitive answers regarding the course of infection in both systems.

Example 7

CD28/CD80 Protein Expression
Introduction

While communication in the immune system is largely mediated through soluble factors, initiation of a primary T cell response in primates and rodents has been determined to require direct cell to cell contact (Mescher, 1992). Originally, this interaction was thought to only involve the interaction between the TCR on the T cell and MHC on the antigen presenting cell, but it has become clear that binding between accessory molecules is required for full activation of the T cell (Schwartz, 1992). As discussed, the evidence supports the interaction between CD28 and CD80 as the mediator of this accessory signal (Linsley et al., 1991a).

Many of the important receptors and ligands in vertebrates are members of the IgSF superfamily (Springer, 1990). The molecules are characterized by the presence of an immunoglobulin-like region, normally in the extracellular portion of the molecule (Buck, 1992). Although conservation varies, it is often limited to those residues required to generate an Ig fold (Beale, 1985). The characteristics of an Ig domain include two closely associated anti-parallel β strands connected by loops following conserved topology (Williams and Barclay, 1988). Although there is a sharing of structural properties among members of this family, there is a diverse array of binding interactions and signaling properties particular to this family (Anderson et al., 1988).

As members of the IgSF family, both CD28 and CD80 share a degree of structural similarity in their extracellular domains. CD28 has a single extracellular V region, though it is expressed as a disulfide linked heterodimer (Aruffo et al., 1987). The extracellular region of the CD80 molecule however has both a V-like and C type of domain and is expressed as a monomer (Freedman et al., 1989). Because IgSF family members share structural features, templates can be used on a limited basis to establish an idea of the three dimensional structure of related molecules that have not been crystallized (Bajorath et al., 1993). Although neither the CD28 nor CD80 polypeptide have been crystallized, CD2 (Driscoll et al., 1991) and CD8 (Leahy et al., 1992), molecules with analogous extracellular domains, have been examined by X-ray crystallography and give some idea as to the structure of related members of the IgSF group (Linsley et al., 1995a).

As previously discussed, CD80 and CD86 share similar binding avidities with CD28 and CTLA-4. CD28, however, is a low affinity receptor for the ligands while CTLA-4 has a high affinity for both molecules (Linsley et al., 1994a). Though a potential mechanism has been proposed, it is unclear how a low affinity receptor with a rapid disassociation rate as is possessed by CD28, is able to deliver the necessary costimulatory signal for T cell development (Linsley et al., 1995a). It is hypothesized that CD80 binding of CD28 on the T cell surface may promote oligomerization of the receptor which would facilitate productive cross-linking and signal delivery (Linsley et al., 1995a). CD28 is found evenly distributed on activated T-cells and so the molecule is proposed to migrate on the membrane following T cell engagement (Damle et al., 1994). High concentration of oligomerized CD28 would promote reassociation of free CD28 in the region of cell:cell contact and promote signal delivery despite the rapid disassociation rate (Linsley et al., 1995a). This process, termed mutual capping, though not directly observed with the CD28/CD80 interaction has been demonstrated for other receptors in which a similar initiation of cell:cell contact is required (Singer, 1992).

While the CD28/CD80 interaction has been demonstrated to be critical for promulgation of a T cell mediated immune response, there remains a great deal that is unclear about the exact mechanisms of this signaling pathway (Linsley et al., 1993a). The existence of two receptors and two ligands in this interaction raises questions as to the role each plays in T cell activity (Linsley et al., 1992b). While CTLA-4 binds more strongly, it is expressed much later following activation, and although signaling pathways have been proposed for CD28, it has not been determined if a signal is delivered upon ligand binding with CTLA-4 (Linsley et al., 1995a).

Materials and Methods
Preparation of Inserts

The following primers were used to amplify the entire open reading frame of the genes for feline CD28 and CD80 for insertion into expression vectors:

```
                                        (SEQ ID NO: 11)
feCD80 5': CGC GGA TCC GCA CCA TGG GTC ACG CAG CAA
AGT GGA AAA C (SEQ ID NO: 12)
fe CD80-960: CCT AGT AGA GAA GAG CTA AAG AGG C (SEQ ID NO: 13)
feCD28 5': CGC GGA TCC ACC GGT AGC ACA ATG ATC CTC
AGG (SEQ ID NO: 14)
feCD28 3': CGC GGA TCC TCT GGA TAG GGG TCC ATG
TCA G
```

The 5' CD80 primer and both CD28 primers were engineered with BamHI sites and the appropriate linkers to facilitate the insertion into multiple cloning sites. The 3' BamHI site was engineered onto the CD80 sequence by digestion out of the TA cloning vector. The 5' primers also contain a Kozak box and the 5' ATG for both genes. In each case, the primers were used to amplify from template encoding the entire sequence of each gene that had been previously cloned into the TA cloning vector, described previously. Approximately ten nanograms of each plasmid were used in a Taq polymerase based PCR amplification (95° C. for 5 min, 1 cycle; 95° C. for 30 sec, 60° C. for 30 sec, 68° C. for 45 sec, 30 cycles; 68° C. for 7 min 1 cycle). The amplified products were visualized by electrophoresis on an agarose gel and then ligated into the TA cloning vector (InVitrogen, San Diego, Calif.), as previously described. The ligation reaction was used to transform InvαF' competent cells, and positive clones were screened and selected as previously described.

Cloning into pSI

For cloning into the pSI vector to be used in the transformation of COS-7 cells, the plasmid was digested with EcoRI, and then enzyme was removed with the Micropure EZ spin column (Amicon, Beverly, Mass.). Following removal of the enzyme, the plasmid was treated with phenol:chloroform to remove any residual protein and alcohol precipitated. The inserts were digested from 50 µg of QIAGEN purified plasmid DNA (Qiagen, Chatsworth, Calif.) from clones containing TA cloning vector with the proper inserts using the EcoRI sites found in the vector flanking the insert. The 100 µl digest was electrophoresed on a 1.5% agarose gel and the digested fragment cut out. The insert was then purified from the agarose with a gel nebulizer and microcon filter unit (Amicon, Beverly, Mass.). Alkaline phosphatase treatment of EcoRI digested pSI reduced the chances of self ligation of the vector. One hr treatment at 37° C. with 0.1 U/µg of calf intestinal alkaline phosphatase (CIP) dephosphorylated the digested ends of the vector. CIP was removed by heat denaturation at 65° C. for 30 min followed by spin purification with the Micropure EZ spin column (Amicon, Beverly, Mass.). The inserts were ligated directly into the cut and dephosphorylated pSI vector overnight at 16° C. using T4 DNA ligase. Ligand to vector molar ratio was approximately three to one with 0.05 µg of CD28 or CD80 insert to 0.1 µg of pSI. One µl of the ligation reaction was then used to transform InvαF' competent cells. The cells were streaked onto LB plates containing 50 µg/ml ampicillin. The plates were incubated overnight at 37° C. and the next day colonies were inoculated into 5 ml of LB media containing 100 µg/ml ampicillin. Following an overnight incubation at 37° C. with shaking at 220 rpm, the plasmid DNA was extracted with alkaline lysis, the DNA purified by phenol:chloroform extraction, and precipitated with two volumes of 95% ethanol. The DNA was RNase treated and then digested with 10 U of EcoRI. The digests were visualized on a 1% agarose gel to identify the positive clones. Plasmid DNA was then extracted from 5 ml of overnight culture of positive clones using QIAprep spin columns (QIAGEN, Chatsworth, Calif.). The purified DNA was then sequenced by dye terminator cycle sequencing with an internal 3' primer to determine the orientation of the insert in the plasmid. Location of the primer was such that sequencing would proceed across the junction between the vector and insert to insure that the orientation was correct. A clone of each gene with the plasmid in the proper orientation was then grown up in a 100 ml culture and the plasmid extracted with a QIAGEN (Chatsworth, Calif.) maxi-prep column.

Cloning into SFV

For insertion into the SFV vector, inserts and the plasmid were treated in much the same way. One hundred µg of the SFV vector was digested with 120 U of BamHI for 1 hr at 37° C. The enzyme was removed from the digest by centrifugation through a micropure EZ filter (Amicon, Beverly, Mass.). The plasmid was then CIP treated. The CIP was heat inactivated and then the plasmid was again purified with a micropure EZ filter. Inserts were extracted from purified TA cloning vector DNA by BamHI digestion. The inserts were purified and ligated into the vector as described previously. Following the transformation of InvαF' competent cells, the plasmid insert and orientation was confirmed with dye terminator cycle sequencing as described. A large scale plasmid preparation was performed on a positive clone of each gene.

pSI Protein Expression

For pSI transformation of eukaryotic cells, COS-7 cells were obtained from the American type culture collection (ATCC). The frozen stock was resuspended in 15 ml of DMEM plus 10% fetal calf serum (FCS). The cultures were then grown as a monolayer in T-75 flasks. On the evening prior to transfection, cells were removed from the flasks after treatment with a 0.25% trypsin EDTA solution by washing with PBS. The cells were then seeded at ~20% confluence into 100 mm tissue culture dishes and allowed to grow to ~50% confluence for the next day. For each dish to be transfected 5 ml of DMEM-NuSerum (Collaborative Biomedical Products, Bedford, Mass.) was mixed with 0.2 ml of DEAE-dextran/chloroquine solution. Ten µg/ml of the purified pSI plasmid was then added to the mixture. The media was aspirated from the COS cells and the DMEM-NuSerum/DEAE-dextran/chloroquine/DNA solution was added to the cells. The culture was incubated for 3.5 hr in a 5% $CO_2$ incubator followed by removal of the media and replacement with 5 ml of 10% DMSO in PBS. After 2 min this solution was aspirated off, and the cells grown overnight in 5 ml of DMEM/10% FBS. The following day, the cells were split into two 100 mm culture dishes. After 3 days, the media was aspirated, and the transformed cells removed with PBS/0.5 µM EDTA. The PBS/EDTA mixture was added to the cells and they were incubated for 15 min at 37° C. The supernatant was removed and combined with subsequent PBS washes. The supernate and washes were then centrifuged. The resulting pellet was resuspended in DMEM/FBS and the COS cells counted.

SFV Protein Expression

Transfection with the SFV vector was carried out in baby hamster kidney (BHK) cells. Thirty µg of purified plasmid was digested with SpeI for 1 hr at 37° C. The enzyme was then removed with a micropore EZ filter (Amicon, Beverly, Mass.) and the DNA precipitated with 2.5 volumes of 95% EtOH. One and a half µg of the plasmid was then used as the template for Sp6 mediated in vitro transcription. Briefly, the DNA was incubated for 1 hr at 37° C. with: transcription buffer, 100 mM DTT, 10 mM G(5')ppp(5')G, rNTP mixture, water, RNasin, and 60 U of Sp6 RNA polymerase. Following transcription the reaction was aliquoted and a sample visualized on a 1% agarose gel. Forty-five µl of the transcription reaction was used to transfect BHK cells at ~80% confluency in T-75 flasks. GMEM media plus 10% FCS media was aspirated from the cells and replaced with Opti-MEM media. After a 2 min incubation this media was replaced with Opti-MEM media/9 µg/ml of lipofectin/transcribed RNA. The cultures were incubated for 2 hr at 37° C. in a 5% $CO_2$ with frequent manual agitation. After 2 hr. the media was removed and replaced with GMEM-10% FCS. The cultures were incubated for 7-9 hr and the cells were then removed by trypsinization.

Cloning into pQE

A bacterial expression vector, pQE was also constructed with the feline CD80 and CD28 gene. Cut and CIP treated pQE plasmid, prepared and purified as previously described was ligated with T4 DNA ligase in a four to one insert to plasmid molar ratio with 50 ng of gel purified CD28 or CD80. The ligation was incubated for 16 hr 16° C. Two µl of the ligation reaction was then used to transform INVαF' competent cells. Positive colonies were selected and insert orientation confirmed by sequencing. Large scale preparation of purified plasmid was performed and this used to transform M15 pREP4 cells made competent by rubidium chloride treatment. Transformed cells were grown up on LB plates with 50 µg/ml kanamycin and ampicillin to insure that both the pQE and helper pREP4 plasmids were retained in these colonies. Positive colonies were then screened by alkaline lysis mini-preps and BamHI restriction digestion. Colonies with confirmed inserts were frozen in a 50% glycerol stock solution for future use.

Binding Assay

Binding assays for transfected cells expressing feline CD80 and feline CD28 were performed after the protocol described in Linsley et al., 1994a. One day after transfection, CD28 expressing COS-7 cells were removed from T-75 flasks with trypsin-EDTA treatment. The cells were allowed to adhere in 24 well plates at a concentration of 1×10⁵ cells per ml. Two days later, the feCD80/pSI transfected COS-7 cells were removed from T-75 flasks with PBS/0.5 µM EDTA. These cells were then fluorescently labeled with a 5 µM solution of Calcein AM (Molecular Probes, Eugene, Oreg.) in sterile PBS/1% BSA for 30 min at 37° C. (Akeson and Woods, 1993). Mock transfected COS-7 cells were labeled in the same fashion. The labeled cells were then washed three times with DMEM plus 10% FCS to remove unincorporated label, counted, and added directly to the monolayer. The two cell populations were allowed to interact for 1 hr at 37° C. Non-adherent cells were removed by gently washing the monolayer 3 times with DMEM +10% FCS. Following the washing, the fluorescence of each of the wells was quantitated on a microplate fluorimeter. Fluorescence in wells containing transfected populations was compared to wells in which CD80 expressing cells were added to COS-7 cells transfected with pSI plasmid alone.

Competitive binding assays, using CTLA-4 Ig and CD80 Ig fusion proteins (kindly provided by P. Linsley, Bristol-Meyers Squibb) to inhibit cell/cell interactions, were designed to demonstrate the specificity of the interaction. Following calcein labeling, but prior to the addition of CD80 expressing cells to the monolayer, CTLA-4 Ig in DMEM/FCS at a concentration of 1 µg/ml was incubated with the labeled transfected cells for 30 min. The cells were washed twice with DMEM/FCS and added to the monolayer. Alternatively, CD28 expressing cells in the monolayer were incubated for 30 min. with CD80 Ig at a concentration of 1 µg/ml in DMEM/FCS and following washing, the fluorescently labeled CD80 expressing cells were added. Inhibition of binding by the fusion proteins was gauged by comparing the fluorescence in these wells with binding observed in wells without the competitors.

RT-PCR

Transfected COS cells were also assayed for mRNA transcription by RT-PCR. After three days, RNA was extracted from cells transfected with pSI with feCD28, feCD80 or without insert. RNA was treated with RNase free DNase to remove the potential for contaminating DNA. One half µg of RNA was then reverse transcribed to cDNA using an oligo dT primer and MuMLV reverse transcriptase. Each cDNA sample was then amplified with primer sets specific for CD28, CD80 and G3PDH with the following temperature cycle: 95° C. 5 min. 1 cycle; 95° C. 30 sec, 55° C. 30 sec, 72° C. 30 sec, 30 cycles; 72° C. 5 min., 1 cycle. 20 µl of each reaction was then visualized on a 1% agarose gel.

Results

The genes for feline CD28 and CD80 were successfully inserted into three protein expression vectors (pSI, SFV and pQE). Following ligation into the respective vectors, the genes were used to transform INVαF' competent cells.

Binding assays were performed to demonstrate that functional protein could be expressed. The initial assays were performed to determine the relation between the binding of CD28 and CD80 transfected COS-7 and CD28 transfected and mock transfected COS-7 cells. Fluorescence in the wells in which the fluorescently labeled non-adherent CD80 transfected cells were added were higher than the control wells at the initial two dilutions. The interaction was dose responsive, and after the initial two dilutions, the retention of fluorescence was the same in wells in which the adherent cells expressed surface protein as in the mock transfected controls.

To show that this interaction could be inhibited, the transfected cell lines were incubated with soluble counter receptor prior to mixing. At concentrations of 5×10⁵ and 1×10⁵ cells, fluorescence in wells containing CD28 and CD80 expressing COS cells was similar to that observed in the previous experiment. In the wells in which the adherent cells were incubated with CD80Ig counter-receptor prior to mixing, fluorescent retention was comparable to that found in the control mock transfected wells. When COS cells transfected with CD80 pSI were incubated with soluble CTLA-4, prior to exposing the cells to the CD28 pSI transfected cells however, the fluorescence was not inhibited as completely. While the levels are not as significant as that seen with the uninhibited group, it was clearly greater than either the control or other experimental group.

RT-PCR was performed on RNA derived from COS-7 cells transformed with pSI-CD28, pSI-CD80 and mock transfected to demonstrate the presence of mRNA specific for each gene in the cell line as executed in a 1% agarose gel for each cell line. The gene for G3PDH was amplified in each set to show RNA integrity and as a positive control in the mock transfected set. CD80 pSI transfected COS-7 cells expressed CD80 mRNA and G3PDH message, while CD28 pSI transfected COS-7 cells expressed the genes for CD28 and G3PDH. Mock transfected cells expressed only G3PDH.

Discussion

A lack of suitable antibodies dictated that a direct assay could not be performed to demonstrate peptide expression. Commercially available anti-hu CD28 and anti-hu CD80 monoclonal antibodies were tested on isolated lymphocytes to determine if there was cross reactivity. FACS analysis using the antibodies on cells confirmed by PCR to be expressing message for both surface proteins was unsuccessful. This in combination with the fact that the antibodies did not recognize surface expression on pSI transfected cells, led to the conclusion that these antibodies were not cross reactive. It was not expected that the CD80 antibody would cross react. The limited homology between the human and feline CD80 molecule would limit the potential for cross reactivity in a monoclonally derived antibody. It was somewhat surprising however that the anti-hu CD28 was not cross reactive. Though there is a higher degree of conservation between the cloned CD28 molecules, a commercially available anti-hu CD28 antibody that cross reacts with the mouse protein was not found. As with the anti-hu CD80 antibody, testing of the hu CD28 monoclonals was unsuccessful. Thus an assay had to be devised that could demonstrate not only the probability that the peptides were being expressed, but that also showed that they were functional and capable of interacting.

The cDNA for feline CD80 and CD28 were successfully inserted into a series of expression vectors. While the pSI vector fulfilled the requirements necessary to carry out the binding assay, the additional vectors may facilitate future protein expression.

Following transfection, expression of CD28 and CD80 mRNA by the COS-7 transformed cell lines was confirmed by RT-PCR. DNase treatment of the RNA prior to the PCR reaction should have significantly reduced any possibility of genomic or plasmid DNA contamination. Further, it was not felt that the COS-7 cells would naturally express either ligand which was further confirmed by the lack of message for either surface protein in the mock transfected control. The amplification of the proper message from the RNA from the transfected cells, appears to reflect that the pSI template was present within the cells and that the message encoded by the plasmid was being transcribed.

The binding assays performed were modeled after those performed by Peter Linsley to demonstrate the similar binding avidities of human CD80 and CD86 (Linsley et al., 1994a). A modified format was used to demonstrate that surface expressed feline CD28 bound to surface expressed feline CD80 and that the interaction could be inhibited with soluble receptor. The level of binding could be inferred from the retention of fluorescently labeled cells in the specific wells. Because a fluorescent plate reader was used, it was not required that cells be lysed prior to measuring fluorescence.

The initial assay demonstrated that the retention of fluorescently labeled CD80-pSI transfected COS cells was greater in wells in which adherent cells were transfected with CD28-pSI than in wells in which the adherent cells were mock transfected. The control cells, COS cells mock transfected with pSI lacking an insert, insured that neither the presence of the vector, the transfection process itself nor the adhesive properties of the cells resulted in the adhesion between cells mediated by the interaction between the surface expressed CD80 and CD28. At the initial dilution of $1 \times 10^6$ cells, the fluorescence in the wells in which the cells were expressing the CD28 was approximately five times that of the wells in which the fluorescently labeled CD80 transfected cells were introduced into wells containing mock transfected cells. At $5 \times 10^5$ cells, fluorescence drops significantly due to the reduction in cell number, but the level is still significantly higher than fluorescence in the control. By a concentration of $1 \times 10^5$ cells the difference between the experimental and control is not statistically distinguishable, and by $1 \times 10^4$ they are nearly identical. This assay indicates that an interaction is occurring between the CD80 transfected and CD28 transfected COS cells that results in the retention of the fluorescently labeled CD80 transfected cells in the wells. When the adherent cells were not expressing surface protein however, the CD80 transfected cells were removed by gentle washing. This effect could be titrated out, and by $1 \times 10^4$ cells fluorescence in the wells was virtually identical. To confirm that an interaction was occurring, soluble receptors were introduced to inhibit the CD28/CD80 interaction.

The second assay involved the introduction of soluble forms of counter-receptors for each peptide in an attempt to inhibit the interaction between the adhesion partners. A soluble receptor for CD80, huCTLA-4Ig and for CD28, huCD80-Ig were incubated with the respective transfected COS cells expressing the counter-receptor of each molecule prior to the mixing of the two cell types. Although the soluble proteins were not on feline origin, it was felt that due to the level of conservation found between the proposed binding region of the human and the analogous regions in the feline molecules, that there would be sufficient cross reactivity. Further, the human fusion partners bind with their murine counter-receptors (P. Linsley, personal communication). Due to the number of cells required in the assay, it was not feasible to perform the assay with $1 \times 10^6$ cells. The first concentration was $5 \times 10^5$ cells, with the CD28/CD80 transfected cells alone demonstrating a mean fluorescence similar to that found in the previous experiment It is not clear why the adherent cells incubated with soluble CD80 receptor had a fluorescence close to that of the mock transfected control, while the non-adherent CD80 transfected fluorescently labeled cells, incubated with soluble CTLA-4 had about a two to three fold higher fluorescence. Despite the differences mediated by the type of soluble receptor, there was a marked reduction in the amount of fluorescence in wells in which soluble receptor was introduced over the wells in which no receptor was present. The interaction demonstrated by the previous assay can be inhibited by the introduction of the proper soluble counter receptor prior to the mixing of the cells.

While monoclonal antibodies specific for surface proteins would in general seem preferable to this type of assay, in the absence of the proper reagents, this seems a viable format through which the expression of functional counter receptors may be demonstrated. The results of the initial binding assay in combination with the competitive binding assay confirm that functional feline CD80 and CD28 cDNA have been isolated, and further that the proteins expressed by the message functionally interact. Although the applications of this type of binding assay are limited, it remains an efficient system in which to demonstrate the probability of functional surface expression and interaction.

Example 8

Infection
Introduction

Lwoff defined viruses as "strictly intracellular and potentially pathogenic entities with an infectious phase and 1) possessing only one type of nucleic acid, 2) multiplying in the form of their genetic material, 3) unable to grow and to undergo binary fission, and 4) devoid of a Lippmann system" (Lwoff, 1957). Viruses are non-cellular in nature, whose genome, whether RNA or DNA, directs the synthesis of further virion particles by an infected host cell (Luria and Darnell, 1968). Viral diseases represent an interesting system in which the practical applications of the B7/CD28 signaling complex can be demonstrated. Among the retroviruses, infection with HIV in humans and feline immunodeficiency virus (FIV) in cats, results in disruption of normal immune function which is hypothesized to occur through the elimination of $CD4^+$ T-cells (Fauci et al., 1984; Pedersen et al., 1987). It is thought that the CD28/CD80 signaling complex plays a role in the illness and that manipulation of receptor expression may exacerbate the infection (Harlan et al., 1995).

FIV is a very real clinical problem in domestic cats, causing a series of clinical and subclinical manifestations that closely resemble HIV infection in humans (Pedersen et al., 1987). As more information is accumulated about FIV, the appropriateness of it as an animal model for human AIDS is becoming more evident and that it is the non-primate model that most closely mimic the progression of disease in humans (Siebelink, 1990). The molecular, biological and pathogenic similarities also suggest that much of the information obtained from HIV studies can accelerate understanding of FIV infection in cats.

Initially, HIV infection is manifested by a transient lymphopenia with the development of mononucleosis like syndrome around the time of seroconversion (Clark et al., 1991). There is a short term decline in $CD4^+$ T cell population and $CD8^+$ T cell expansion results in an initial decline in CD4: CD8 ratios, that can contribute to a further decrease during the asymptomatic phase of the illness (Cooper et al., 1984). By the onset of AIDS related symptoms, the $CD4^+$ T cell population is seriously diminished, and as the disease progresses to its terminal phase the entire lymphocyte population is drastically diminished (Fauci et al., 1984). While the initial lymphocytopenia is probably due to cortico-steroid induced shifts in immune cell populations as is seen in other viral diseases, further $CD4^+$ T cell loss and $CD8^+$ T cell expansion are thought to be related to viral proliferation and pathogenesis (Fauci and Dale, 1975; Fauci et al., 1984). The development of appropriate model systems is a critical step in further elucidating mechanisms of infection and virally induced disease.

FIV, a T lymphotropic retrovirus, was originally described in a cat colony from California in which multiple, often chronic infections occurred (Pedersen et al., 1987). Although the disease manifests itself in a similar manner as HIV in humans and is distantly related taxonomically, it is antigenically distinct from the causative agent of AIDS in humans (Siebelink et al., 1990). Transmission of the infection occurs through the exchange of infected bodily fluids, as in HIV, but unlike HIV in which sexual transmission is the primary route of infection, it appears that with FIV, the majority of infections occur by salivary transmission through bites (Yamamoto et al., 1989). Despite differences in transmission, the resulting immunodeficiency syndrome is one of the best models of the related illness in humans (Siebelink et al., 1990).

Clinical progression of FIV is similar to HIV with the disease subdivided into five clinical stages. The initial stage is characterized by fever, malaise and lymphadenopathy, a long asymptomatic phase follows infection and precedes the onset of the final three stages in which weight loss and multiple secondary and opportunistic infections occur (English et al., 1994). Although it is not clear if the route of cellular infection is the same, FIV is tropic for $CD4^+$ T-cells as well as $CD8^+$ T-cells (Brown et al., 1991). Virally infected animals experience a decrease in $CD4^+$ T cell activity perhaps due to synctia formation and cell lysis (Siebelink et al., 1990). The onset of the final stage of the infection coincides with a significant loss of $CD4^+$ T-cells and a decrease of CD4:CD8 ratio (Novotney et al., 1990). While HIV and FIV induced disease may not mediate $CD4^+$ T cell loss in the same manner, the resulting phenotype and immune system dysfunction appear to be manifested in a quite similar manner.

Although it is clear that infection of $CD4^+$ T-cells with HIV adversely effects the development of a normal immune response, the exact mechanism of the interaction that results in immunodeficiency has not been conclusively defined. In the late stages of the infection the events resulting in the reduction of $CD4^+$ T-cells is undefined (Connor et al., 1993). While the development of synctia, induction of apoptosis, and the elimination by CTL have all been demonstrated to reduce T cell populations in HIV infections (Schattner and Laurence, 1994; Fouchier et al., 1996), a CD28 mediated mechanism has also been proposed (Haffar et al., 1995). Infected T cell lines have been demonstrated to down-regulate CD28 expression at both the protein and mRNA level upon allo-antigen stimulation (Haffar et al., 1995). As previously discussed, CD28 cross-linking is a critical signal for the maturation of a T cell response (Linsley et al., 1991a). If HIV infection results in a down-regulation of CD28 surface expression, then infected T-cells that recognize presented antigen may become apoptotic rather than fully activated (Schattner and Laurence, 1994). While apoptosis is a normal mechanism of HIV infected cell death, this pathway may be an additional contributor to the concomitant T cell elimination (Brinchmann et al., 1994).

$CD8^+$ CTL have been related to the development of long term survival in HIV infection, with high levels of CTL associated with long term non-progression in AIDS infected individuals (Landay et al., 1994). In contrast, humoral immunity has not only been generally ineffective in controlling lentiviral associated illness, it has been shown that antibodies may actually enhance disease (Lombardi et al., 1994; Siebelink et al., 1995). Onset of the final clinical stage of HIV infection and concomitant immunodeficiency is correlated with the switch from a cellular, type 1 response to a humoral, type 2 response in many patients (Schattner and Laurence, 1994). This coincides with observations that progression from a healthy state to the development of AIDS is related to a decrease in $CD8^+$ CTL mediated antiviral activity (Lewis et al., 1994). Expression of CD28 on $CD8^+$ CTL also appears to be related to their antiviral activity, with a strong CTL mediated antiviral activity associated with the expression of CD28 on CD8 populations within the infected individual (Landay et al., 1993).

CD28 surface expression, though proposed as a mediator required to promote HIV resistance, is adversely effected by the presence of HIV in both infected and uninfected T-cells (Caruso et al., 1994). Beginning in the asymptomatic stages of an HIV infection, a reduction in the percentage of CD28 bearing $CD4^+$ and $CD8^+$ T-cells is detected (Lewis et al., 1994). It is proposed that this may account for abnormalities in cytokine secretion patterns seen early in the infection (Caruso et al., 1994) as well as altered $CD8^+$ T cell responses in later stages (Zanussi et al., 1996). In HIV infected individuals, reduction in the proliferation of $CD8^+$ T-cells in the early stage of infection is proposed to be related to CD28 down-regulation as only $CD8^+$ T-cells expressing CD28 proliferate in response to IL-2 (Brinchmann et al., 1994). Unfortunately in infected individuals, $CD28^-$, $CD8^+$ T-cells can constitute as much as 75% of the $CD8^+$ population, while in normal individuals they make up only 25% of the population (Saukkonen et al., 1993). Thus, while $CD8^+$ populations may remain normal in infected individuals, the effectiveness of this population in its ability to mount an effective anti-viral immune response may be adversely effected even in the initial phase of the infection (Caruso et al., 1994).

Studies have also demonstrated that CD28 signal transduction may be involved in the activity of the virus (Asjo et al., 1993; Smithgall et al., 1995). Costimulation of HIV infected peripheral blood $CD4^+$ T-cells with anti-CD3 and anti-CD28 results in higher viral replication than stimulation with anti-CD3 alone (Smithgall et al., 1995). This response can be ablated by the addition of CTLA-4 Ig as a soluble form of the CD80 receptor and to a lesser degree by anti-IL-2 (Smithgall et al., 1995). In other studies with infected $CD4^+$ T-lymphocytes, in 40% of patients it was demonstrated that CD28 ligation alone resulted in the up-regulation of virus production without additional stimuli required (Asjo et al., 1993).

Pretreatment of lymphocyte populations with the HIV surface glycoprotein gp120 results in the down-regulation of CD80 on the surface of APC (Chirmule, 1995). While CD28 expression on T-cells appears to be down-regulated by HIV infection, CD80 expression is up-regulated on these cells (Haffar et al., 1993). This is a proposed mechanism by which infection may be transferred to uninfected T-cells as the interaction between CD28 on uninfected T-cells and CD80 on infected T-cells may facilitate the cell to cell contact that allows the transfer of virus (Haffar et al., 1993).

While the effects of CD28 in HIV have been explored, the role of the surface protein in FIV has not been distinguished. If similar results can be demonstrated in the cat as are observed in the human system, it will further confirm the usefulness of the feline as a retroviral model.

Materials and Methods

Infection in Vivo

Three adult specific pathogen free (SPF) female cats were infected intravenously with $1 \times 10^5 TCID_{50}$ of the Maryland strain of the FIV virus. Two similar females were mock infected with serum containing no virus to serve as controls. Blood was extracted prior to the infection and once every week for seven weeks. In the initial week of the infection, cats were monitored twice a day to insure that no initial reaction from the injection occurred. As the infection progressed, the animals were monitored on a daily basis. Every week, during the acute stage of the clinical illness, 5-10 ml of blood was collected for CBC determination and PBMC isolation. CBC was determined by counting cell types in a dip-quick stained blood smear (Jorgensen Lab., Loveland, Colo.).

The PBMC were extracted from the blood by separation over a histopaque gradient (Sigma, St. Louis, Mo.). Following initial washing with Alsever's solution, ~$5\times10^5$ cells were removed and divided into 5 wells of a 48 well plate. The cells were resuspended in 500 µl of complete RPMI, and then labeled with antibodies directed against either CD4 or CD8. After an hour incubation at room temperature with gentle rocking, the cells were washed two times with PBS.

Following washing, the secondary antibody, goat anti-mouse IgG (H+L) FITC labeled (KP&L, Gaithersburg, Md.), at a concentration of 1:500 was added and incubated at room temperature for 1 hr with gentle rocking. The cells were then washed three times with PBS and fixed with 3.7% formaldehyde. Fluorescently labeled populations were then quantitated on a FACSCalibur flow cytometer.

The remaining PBMC were washed an additional time with 10 ml of Alsever's solution. Following centrifugation, the supernate was removed, and 1 ml of ULTRASPEC (Biotexc, Houston, Tex.) was added for RNA extraction. The RNA was purified and precipitated as previously described. The concentration was then quantitated by measurement of absorbance at 260 nm on a spectrophotometer. The RNA was then resuspended in 50 µl of DEPC treated water and frozen at −70° C. for later use.

Semi-Quantitative RT-PCR

Prior to PCR amplification of sample RNA, 60 ml of blood was collected from a terminally bled cat. PBMC were isolated as described previously. The cells were counted on a hemacytometer and divided into 4 flasks at a concentration of $5\times10^5$ cells per ml. The cells were stimulated with Con A for 0, 8, 16 and 24 hr prior to centrifugation and extraction of RNA from the cell pellet with ULTRASPEC as previously described. RT-PCR was performed using 1.5 µg of RNA transcribed to cDNA with MMLV reverse transcriptase and an oligo dT 3' primer. The RNA, dT primer and DEPC treated $dH_2O$ were incubated for 5 min at 70° C. to remove RNA secondary structure and allow for primer annealing. Transcription buffer, $MgCl_2$, dNTP, and DTT were then added and the mixture incubated for 2 min at 42° C. One µl of reverse transcriptase was then added and the reaction allowed to proceed for 30 min. Four µl of the 25 µl RT reaction was then added to each of three tubes for CD80 amplification and three tubes for CD28 amplification.

A mixture of 10× PCR buffer, dNTP and CD28 or CD80 specific primers were then added to the cDNA. The primers for CD80 were:

```
                                       (SEQ ID NO: 74)
B7-S220 5' primer: CAT GTC TGG CAA AGT ACA AG;

(SEQ ID NO: 75)
B7-284 3' primer: TTA TAC TAG GGA CAG GGA AG;
```

While the primers used for CD28 were:

```
                                       (SEQ ID NO: 13)
CD28 5' start: CGC GGA TCC ACC GGT AGC ACA ATG ATC
CTC AGG;

(SEQ ID NO: 73)
CD28-239 3': ATT TTG CAG AAG TAA ATA TCC;
```

The three tubes for each product were then incubated at 95° C. for 5 min and then 0.25 µl of Taq polymerase in 10 µl of water was added to each tube. The reactions were subjected to the cycles of the following temperature profile: 95° C. 30 sec, 55° C. 30 sec, and 72° C. 30 sec. A tube was removed at 20, 25 and 30 cycles respectively. Twenty µl of each reaction was visualized on a 1% agarose gel. The agarose gel was photographed and the number of cycles at which a product appeared determined. Following these preliminary experiments, RNA previously extracted from the infected and control animal was amplified in a similar fashion.

Infection in Vitro

In vitro FIV infected T cell lines were stimulated with Con A for 0, and 16 hr and expression of CD28 and CD80 assayed by the semiquantitative RT-PCR method. The FETJ cell line is a mixed T-lymphocyte population that grows in the absence of IL-2 in the growth media. Independent subpopulations of these cells have been exposed to the Maryland strain and the Petaluma strain of the FIV virus. Approximately twenty million normal, Petaluma infected and Maryland infected FETJ were stimulated for 0 and 16 hr with 8 µg/ml of Con A. RNA was extracted from these cells after the incubation with the ULTRASPEC RNA extraction reagent (Biotexc, Houston, Tex.) and purified as previously described.

MCH 5.4 is a T cell line derived from a cat in a colony that had multiple FIV infections although this line is not chronically FIV infected. Approximately twenty million MCH 5.4 cells were pelleted by centrifugation and resuspended in 5 ml of concentrated FIV infected supernatant. The cells were incubated at this concentration for 30 min in a 5% $CO_2$ incubator at 37° C. before adjusting to a concentration of ~$5\times10^5$ and cultured for 24 hr. After normal and infected MCH 5.4 were stimulated for 0 and 16 hr with 8 µg/ml of Con A. RNA was extracted with the ULTRASPEC RNA extraction reagent (Biotexc, Houston, Tex.) and purified as previously described.

Northern Blotting

For Northern blot analysis, RNA concentrations were determined by spectrophotometric analysis at 260 nm. Fifteen µg of each RNA sample was concentrated to 3 µg/µl and resuspended in 3 volumes of sample loading buffer. The samples were then heated to 70° C. for 15 min to denature the RNA and remove secondary structure. The samples, at a volume of 20 µl, were loaded onto a 1% denaturing agarose gel and then electrophoresed at 70 volts for 2.5 hr until the bromophenol blue dye front reached within 2 cm of the bottom of the gel. The RNA was then transferred from the gel to a Genescreen nylon membrane (Dupont NEN, Boston, Mass.) by downward capillary action. The RNA was UV cross-linked onto the membrane by exposure to low intensity UV light for 3 min and then the lanes were visualized for integrity of the ribosomal bands by UV shadowing.

A feline CD28 specific probe was constructed using random primed cDNA labeling. A full length CD28 molecule was cut from the TA cloning vector using flanking EcoRI sites. The fragment was purified by gel electrophoresis and extracted from the agarose with the Amicon gel nebulizer (Amicon, Beverly, Mass.). 25 ng of purified product was incubated with random decamers for 5 min at 95° C. to remove secondary structure (Ambion, Austin, Tex.). The reaction was then snap frozen in liquid nitrogen and dNTP lacking dATP and $P^{32}\alpha$dATP were added to the mixture. Following a 1 min incubation at 37° C., 1 µl of Klenow DNA polymerase was added, and the mixture incubated for 30 min. The reaction was stopped with the addition of 1 µl of 0.5 M EDTA, and subsequently purified with a Sephadex G-50 spin column (Sigma, St. Louis, Mo.) to remove unincorporated radio-labeled nucleotide. 1 µl of the reaction was diluted in 1 ml of scintillation fluid, and the activity of the probe determined on a scintillation counter. Blots were prehybridized for 15 min at 65° C. in 5 ml of Rapid Hyb hybridization fluid (Amersham Life Science, Cleveland, Ohio). Five µl of the probe, at a concentration of 3-5×$10^6$ cpm/µl, was added to each blot, and incubated with rotation for 1.5 hr. at 65° C. The probe was removed, and the blots washed two times in 1% SSC/0.1% SDS at room temperature for 15 min. The blots were then scanned with a Gieger counter and rewashed at 65° C. if necessary. Labeling was quantitated on a Betagen scanning device. A final wash at 65° C. for 15 min. was performed, and the blot placed on film for 16-24 hr at −70° C. with an intensifying screen. The autoradiograph was developed and the bands quantitated by densitometry. RNA integrity and concentration was confirmed with a G3PDH specific probe (kindly provided by Prof. J. Piedrahita, Texas A&M University) labeled and hybridized in a similar manner.

Semi-Quantitative RT-PCR From the in Vitro Infected Cells

The presence of CD28 was further measured by semi-quantitative PCR. As previously described, the concentration of extracted RNA was estimated by spectrophotometric readings at 260 nm. Two μg of RNA (25 μl final volume) were transcribed to cDNA using an oligo dT primer and MMLV reverse transcriptase as previously described. Three and one half μl of the RT reaction was then transferred to seven PCR tubes. Three tubes were amplified using CD80 specific primers, three tubes were amplified using CD28 specific primers and the remaining tube was amplified with G3PDH specific primers:

(SEQ ID NO: 76)
G3PDH 5': CCT TCA TTG ACC TCA ACT ACA T;

(SEQ ID NO: 77)
G3PDH 3': CCA AAG TTG TCA TGG ATG ACC;

As previously described, tubes were removed at 20, 25 and 30 cycles. Twenty μl of each sample was visualized on a 1% agarose gel. In addition, the presence of certain T cell derived cytokines were similarly assayed from RNA from FETJ and MCH 5.4 cells. Primers specific for:

(SEQ ID NO: 78)
IL-2 5': CAA CCC CAA ACT CTC CAG GAT G;

(SEQ ID NO: 79)
IL-2 3': GGT CAG CGT TGA GAA GAT GCT TTG;

(SEQ ID NO: 80)
IL-4 5': TAT TAA TGG GTC TCA CCT ACC;

(SEQ ID NO: 81)
IL-4 3': TTG GCT TCA TTC ACA GAA CAG;

(SEQ ID NO: 82)
IFNγ 5': GGG TCG CTT TTC GTA GAC ATT TTG;

(SEQ ID NO: 83)
IFNγ 3': CAG GCA GGA CAA CCA TTA TTT C;

were used to amplify cDNA transcribed from 1.25 μg of RNA. Twenty percent of the transcription reaction was amplified for each cytokine. The remaining cDNA was amplified using G3PDH specific primers. The cDNA was amplified for 30 cycles using the following parameters: 95° C. 5 min 1 cycle; 95° C. 30 sec, 55° C. 30 sec, 72° C. 30 sec 30 cycles; 72° C. 5 min 1 cycle. Twenty μl of the reaction were then visualized on a 1% agarose gel.

RT-PCR to Determine Infection

Infection of FETJ and MCH 5.4 cells was confirmed through RT-PCR amplification of gag specific sequence. RNA at a concentration of 1.25 μg was transcribed to cDNA at previously described parameters using MMLV RT and a gag specific 3' primer. Ten μl of the RT reaction were amplified by Hot start PCR with the following parameters: 95° C. 5 min; 95° C. 30 sec, 55° C. 30 sec, 72° C. 30 sec, 30 cycles; 72° C. 5 min. Following amplification, 20 μl of each sample were visualized on a 1% agarose gel.

Results

To determine the effects of acute in vivo infection on CD28 expression, cats AUO4, AUU3 and OAC2 were infected with the virus by intravenous injection, while cats AWG3 and OAE6 were injected with media alone. FACS analysis showed some differences between in CD4:CD8 ratios with the experimental animals and the controls. While the control animals overall maintained a fairly constant ratio of around two to one, there were some fluctuations in the experimental group with the ratio dipping as low as one to one in one animal (Table 3).

TABLE 3

CD4:CD8 T-lymphocyte ratios from PBMC drawn from acutely infected and uninfected cats.

| CD4:CD8 | WK 1 | WK 2 | WK 3 | WK 4 | WK 5 | WK 6 | WK 8 |
|---|---|---|---|---|---|---|---|
| Infected | | | | | | | |
| AUO 4 | 4.5 | N/D | 1.9 | 1.2 | 1.0 | 1.5 | 1.6 |
| AUU 3 | N/D | 2.3 | 2.9 | 1.3 | 1.2 | 1.1 | 2.1 |
| OAC2 | 2.8 | 1.48 | 2.3 | 1.9 | 1.1 | 1.14 | 1.1 |
| Uninfected | | | | | | | |
| AWG 3 | 2.6 | 1.5 | 19 | 2.0 | 1.8 | 1.9 | 2.2 |
| OAE 6 | 2.1 | 1.5 | 1.9 | 1.2 | 1.8 | 2.0 | 2.0 |

The time course of CD80 and CD28 RNA expression was performed to demonstrate that message for each molecule was present and could be amplified by PCR at the time points of 0, 8, 16 and 24 hr following Con A stimulation. This semi-quantitative PCR procedure looked to detect a visible band at the lowest number of amplification cycles which could be inferred as a relative measure of message abundance. A definitive CD80 specific band was not apparent at 20 to 25 cycles at any time post infection, though CD80 message was visible on the gel by 30 cycles in each of the experimental groups. CD28 message was also visible at each time point by 30 cycles, though the 16 hr time point also had a faintly visible band at 25 cycles.

A similar protocol was employed with RNA extracted from the PBMC of FIV infected and uninfected cats. RT-PCR amplification of CD28 and CD80 specific RNA was used to demonstrate a relative idea of the amount of message transcribed for each peptide. As performed previously in the time course experiments, samples were removed at 20, 25 and 30 cycles. No message could be detected after 20 cycles, though both CD80 and CD28 products were visible by 25 cycles (Table 4). There were no demonstrable differences in expression of either message between the experimental and control groups. Both subsets had fluctuations in which amplification cycle point that product was visible.

TABLE 4

Semi-quantitative determination of CD80 and CD28 RT-PCR products amplified from infected and uninfected PBMC RNA at intervals during the acute stage of an FIV infection.

| CYC NO B/C | PRE INF | WK 1 | WK 3 | WK 4 | WK 6 | WK 8 |
|---|---|---|---|---|---|---|
| INFECTED | | | | | | |
| AUO 4 | 30/30 | 30/30 | 30/30 | —/25 | 30/25 | 25/25 |
| AUU 3 | 30/30 | 30/30 | 25/25 | —/25 | 30/25 | —/30 |
| OAC2 | 30/30 | 30/30 | 30/30 | —/30 | 25/30 | 25/25 |

TABLE 4-continued

Semi-quantitative determination of CD80 and CD28 RT-PCR products amplified from infected and uninfected PBMC RNA at intervals during the acute stage of an FIV infection.

| CYC NO B/C | PRE INF | WK 1 | WK 3 | WK 4 | WK 6 | WK 8 |
|---|---|---|---|---|---|---|
| UNINFECTED | | | | | | |
| AWG 3 | 25/30 | 30/30 | 30/25 | —/30 | 30/25 | 25/25 |
| OAE 6 | 30/30 | —/30 | —/30 | —/25 | 30/30 | 25/25 |

PCR amplification of mRNA from FETJ and MCH 5.4 cell lines using FIV gag specific primers demonstrated that the MCH 5.4 cell line was infectable, and carried an active infection while the FETJ cell lines did not yield gag specific RNA amplified. FIV specific product was readily amplifiable from RNA extracted from infected MCH 5.4 samples though not from RNA similarly extracted from uninfected controls. Similar reactions performed on RNA extracted from FETJ cell lines exposed to FIV Petaluma and Maryland strains did not have visible product under similar conditions.

Northern blotting and semi-quantitative PCR to detect CD28 message were performed on normal FETJ and MCH 5.4 cell lines. The MCH 5.4 cell line had an infected experimental group and an uninfected control, while the FETJ cell line was used as a nonpermissive T cell control.

The semi-quantitative PCR demonstrated that each cell line was capable of producing CD28 message. Amplification in the FETJ uninfected control demonstrated an expression pattern similar to that seen in the time course for CD28 discussed previously. While at 0 hr post stimulation, a band was not visible until after 30 cycles, at 16 hr post stimulation, banding was visible after 25 cycles. A similar pattern was observed in the noninfected MCH 5.4 cell line with no bands visible before 30 cycles at 0 hr and bands visible after 25 cycles following a 16 hr incubation. Interestingly, the infected MCH 5.4 cell line demonstrated a pattern different from each of the controls. In the experimental group, message was not visible at either 0 or 16 hr until 30 cycles. G3PDH message was amplified as a control to insure RNA integrity and concentration. Infection appeared to influence CD28 RNA message expression.

Northern blot analysis was used to confirm the data found using the semi-quantitative RT-PCR technique. RNA from 16 hr Con A stimulated MCH 5.4 cells that were uninfected demonstrated the strongest probe hybridization. Unstimulated sample from the uninfected line had a greater rate of hybridization than either the stimulated or unstimulated infected MCH 5.4 cell line RNA.

In addition to the autoradiographs, radioactivity was measured on the BetaGen. Raw counts from CD28 hybridization were standardized with counts obtained from a subsequent GAPDH probe of the blot (Table 5).

TABLE 5

Normalized counts for CD28 Northern blots from the BetaGen.

| | G3PDH | CD28 | CD28 norm. |
|---|---|---|---|
| MCH5.4 nor | 14995 | 14921 | 14807 |
| MCH5.4 Con A | 13336 | 13270 | 15430 |
| MCH5.4 inf | 16700 | 10854 | 9867 |
| MCH5.4I Con A | 15112 | 11077 | 10967 |

RT-PCR amplification of cytokine RNA from MCH 5.4 cell lines showed amplifiable message only for IL-2. Neither IL-4, IL-6 or IFNγ could be amplified with 30 cycles, though IL-2 message was easily detectable.

Discussion

CD28 message was measured in in vivo and in vitro infection to determine if CD28 expression could be assayed and if infection with the retrovirus altered the message's expression. When sufficient RNA could be recovered, CD28 message was measured by northern blotting and by a semi-quantitative RT-PCR assay when recovery was limited.

Following in vivo experiments the infection of three animals with the Maryland strain of FIV as previously explained, CD28 and CD80 specific message was amplified from RNA extracted from PBMC from isolated from blood from these infected animals and non-infected controls. Although determination by Northern blotting would have been preferable, the semi-quantitative RT-PCR was employed because of limitations on the number of cells and the amount of RNA available. The cats were bled at weekly intervals, so a maximum of 10 ml of blood was available for each experiment.

FACS analysis of the CD4/CD8 ratios of the PBMC from infected animals declined over the 8 wk period as compared to the uninfected animals in which ratios remained relatively constant. There are differences between the two experimental groups. Though the CD4/CD8 ratios appear to differ in the infected versus uninfected animals, no real differences in CBC or CD80 and CD28 expression were detectable (data not shown).

To optimally determine CD28 expression pure T-cells were required. From the PBMC isolated, on an average, perhaps 40% of the cells were in fact T-cells. Of these cells at times up to half would be $CD8^+$ T-cells which do not express CD28 at the same concentration as $CD4^+$ T-cells. This in conjunction with the fact that, in other species, CD28 it not expressed at high levels by resting T-cells (which constitute the majority of circulating T-cells) led to the decision to employ PCR determination rather than Northern blotting. Preliminary experiments attempting to detect CD28 message from 20 μg of RNA extracted from PBMC were unsuccessful. The semiquantitative RT-PCR reaction, does detect the presence of RNA encoding CD28. This technique was also used to amplify message specific for CD80.

In vitro cell lines provided RNA from which CD28 message was detected by Northern blotting. The MCH 5.4 was chosen because as a T cell line, all of the cells potentially express CD28 message, and a derivative line had previously harbored a chronic viral infection. A final benefit was that as a cell line, a far greater reservoir of RNA was available than from lymphocytes from blood extracted from a single animal.

Attempts were also pursued to detect CD80 message by Northern blotting. While CD80 is present at a low concentration on resting B-cells, and monocytes, the highest levels of expression are found in stimulated monocytes and macrophages. A feline antigen presenting cell line was unavailable, and T-cells normally only express the peptide at low levels. Experiments to detect CD80 specific message from RNA extracted from PBMC was unsuccessful probably for similar reasons as were discussed with CD28. Alternatively, semi-quantitative PCR was employed with cells derived from the infected animals to demonstrate CD80 and CD28 message. Though not providing a definitive answer as to message quantity, this assay does demonstrate message is present and a relative display of abundance.

Northern blot analysis of CD28 message from a feline T cell line was successful. When the message for CD28 was compared in infected and non-infected cells there were differences in the expression patterns. CD28 message was most abundant in uninfected cells exposed to Con A for 16 hr.

Message was also detected in unstimulated and uninfected cells. While message was detectable in the RNA from stimulated and unstimulated FIV infected cells, levels were markedly less than in the uninfected cells. This data correlates well with similar findings encountered using the RT-PCR detection technique.

The ability to detect CD28 message is not encumbered by the same limitations found with the CD80 molecule. However, if a large population of CD80 expressing cells can be isolated it would certainly be feasible to detect message through Northern blotting. When peptide specific monoclonal antibodies are developed for these surface proteins, it will be interesting to correlate message levels with the amount of surface expression for each peptide.

Cytokine cDNA was amplified to insure that there were no differences in infected and uninfected lines. IL-2 was amplified from each group irrespective of infection status. No other cytokine message was amplified.

The Northern blot indicates that CD28 expression at the mRNA level is down-regulated in vitro by the presence of FIV. While this finding should be confirmed by measuring surface protein expression, it appears that FIV infection in vitro may influence CD28 expression as has been demonstrated in human T-cells infected with HIV (Brinchmann et al., 1994).

Conclusion

Cloning and sequencing of the cDNA encoding the CD28 and CD80 signaling complex from the feline system yielded product analogous to the molecules isolated from other systems. While the putative amino acid sequence of the feline protein demonstrated relatively low identity with the human and murine polypeptides, comparisons of homology between previously cloned molecules, the retention of characteristic residues, and the fact that the surface ligand is not thought to have a signaling function, led to the conclusion that the isolated product was in fact the feline analog of CD80. In contrast the feline CD28 molecule retained moderate identity at both the nucleic acid and putative amino acid level, and was analogous to molecules cloned in other species.

The nature of the molecules were further identified by demonstrating interaction in binding assays. Monoclonal antibodies directed against the analogous proteins in other species could not react with the expressed feline proteins. Thus a set of binding assays was designed to demonstrate that interaction occurred, and that the interaction was inhibitable by soluble receptor. In these assays, binding was demonstrated by retention of fluorescently labeled cells, which was inhibitable by the introduction of soluble counter-receptors. These assays demonstrated not only that the proteins for feline CD80 and CD28 could be expressed, but also that the surface expressed molecules were able to interact.

The expression of the molecules in an active infection was also characterized. The expression of CD28 and CD80 was assayed in in vivo and in vitro systems exposed to the FIV virus. The expression of CD28, which in human cells infected with the HIV virus, has been shown to be altered (Asjo et al., 1993) was also adversely affected by FIV infection of feline T-cells. Further information regarding the expression of each of these molecules in the progression of the disease should continue to establish the feline system as an important model of retroviral infection.

The long term applications of these molecules is potentially vast. An understanding of immune systems evolutionarily divergent from the human system can only lead to a more thorough understanding of how the system functions in man. Further, the importance of the feline species as a model in retroviral infection is clearly established (Siebelink et al., 1990). The CD80 has been proposed as a potential adjuvant to induce memory CTL in anti-retroviral vaccines. The feline system would be an exceptional model in which to test the efficacy of this system.

REFERENCES

Azuma, M., et al., J. Immunology 149, 1115-1123 (1992).
Azuma, M., et al., Nature 366, 76-79 (1993).
Chambers, et al., Current Opinion in Immunology 9, 396-404. (1997)
Chen, et al., J. Immunology 148, 2617-2621 (1992).
Chen, et al., Cell 71, 1093-1102 (1992).
Donnelly J J., et al., Annu Rev Immunol 1997; 15: 617-648
Freeman, et al., J. Immunology 143 2714-2722 (1989).
Freeman, et al., J. Exp. Med. 174, 625-631 (1991).
Gimmi, et al., Proc. Natl. Acad. Sci. USA 88, 6575-6579 (1991).
Hathcock, et al., J. of Exp. Med. 180, 631-640 (1994)
Hassett and Whitton, Trends Microbiol 1996; 4: 307-312.)
Linsley, et al., Proc. Natl. Acad. Sci. USA 87, 5031-5035 (1990).
Jenkins, et al., J. Immunology 147, 2461-2466 (1991).
Riley, et al., J. Immunology 158, 5545-5553 (1997).
Tsuji, et al., Eur J Immunology 27(3), 782-787 (1997).
PCT International Application WO 92/00092, Bristol Myers Squibb.
PCT International Application WO 92/15671, Cytomed, Inc. 17 Sep. 1992.
PCT International Application WO 93/00431, Bristol Myers Squibb, 7 Jan. 1993.
Akeson, A. L. and Woods, C. W. (1993). A fluorometric assay for the quantitation of cell adherance to endothelial cells. J. Immunol. Meth. 163, 181-185.
Allison, J. P., and Lanier L. (1987). The structure, serology, and function of the T-cell antigen receptor. Annu. Rev. Immunol. 5, 503-540.
Allison, J. P. (1994). CD28-B7 interaction in T-cell activation, Current Opinion Immunol. 6, 414-419.
Anderson, P., Morimoto, C., Breitmeyer, J. B., Schlossman, S. F. (1988). Regulatory interactions between members of the immunoglobulin superfamily. Immunol Today 9, 199-203.
Antonia, S. J., Munoz,-Antonia, T., Soldevila, G., Miller, J., Flavell, R. A. (1995). B7-1 expression by a non-antigen presenting cell-derived tumor. Can. Res. 55, 2253-2256.
Arima, T., Rehman, A., Hickey, W., Flye, M. (1996). Inhibition by CTLA-4Ig of experimental allergic encephalomyelitis. J. Immunol. 156, 4917-4924.
Arruffo, A. and Seed, B. (1987). Molecular cloning of a CD28 cDNA by a COS cell expression system. Proc. Nat. Acad. Sci. USA 84, 8573-8577.
Asjo, B., Cefai, D., Debre, P., Dudoit, Y., Autran, B. (1993). A novel mode of human immunodeficiency virus type 1 (HIV-1) activation: ligation of CD28 alone induces HIV-1 replication in naturally infected lymphocytes. J. Virol. 67, 4395-4398.
Azuma, M., Cayabyab, M., Buck, M., Phillips, J. H., Lanier, L. L. (1992). Involvement of CD28 in MHC unrestricted cytotoxicity mediated by a human killer leukaemic cell line. J. Immunol. 149, 1115-1123.
Azuma, M., Yssel, H., Phillips, J. H., Spits, H., Lanier, L. L., (1993b) Functional expression of B7/BB1 on activated T-lymphocytes. J. Exp. Med. 177, 845-850.
Azuma, M., Cayabyab, M., Phillips, J. H., Lanier, L. L. (1993c). Requirements for CD28-dependant T cell-mediated cytotoxicity. J. Immunol. 150, 2091-2101.

Bajorath, J., Stenkamp, R., Aruffo, A. (1993). Knowledge based protein modeling: concepts and examples. Prot. Sci. 2, 1798-1810.

Bajorath, J., Peach, R., Linsley, P. S. (1994). Immunoglobulin fold characteristics of B7-1 (CD80) and B7-2 (CD86). Prot. Sci. 3, 2148-2150.

Balazano, C., Buonavista, N., Rouvier, E., Golstein, P. (1992) CTLA-4 and CD28: similar proteins, neighbouring genes. Int. J. Can. Suppl. 7, 28-32.

Barcy, S., Wettendorf, M., Leo, O., Urbain, J., Kruger, M., Ceuppens, J. L., de Boers, M. (1995).

FcR crosslinking on monocytes results in impaired T cell stimulatory capacity. Int. Immunol. 7, 179-189.

Beale, D. (1985). A comparison of the amino acid sequences of the extracellular domains of the immunoglobulin super-family. Possible correlations between conservancy and conformation.

Comp Biochem Physiol. 80, 181-194.

Bellone, M., Iezzi, G., Manfredi, A. A., Protti, M. P., Dellabona, P., Casorati, G., Rugarli, C. (1994). In vitro priming of cytotoxic T lymphocytes against poorly immunogenic epitopes by engineered antigen presenting cells. Eur. J. Immun. 24, 2691-2698.

Berke, G. (1993). The functions and mechanisms of action of cytolytic lymphocytes. In "Fundamental Immunology," (W. Paul). pp. 965-1014. New York: Raven Publ. 3rd ed.

Berke, G. (1994). The binding and lysis of target T-cells by cytotoxic lymphocytes. Annu. Rev. of Immunol. 12, 735-773.

Boise, L. H., Minn, A. J., Noel, P. J., June, C. H., Accavitti, M., Lindstein, T., Thompson, C. B. (1993). CD28 costimulation can promote T cell survival by enhancing the expression of Bcl-$x_L$. Immunity 3, 87-89.

Brinchmann, J. E., Doblung, J. H., Heger, B. H., Haaheim, L. L., Sannes, M., Egeland, T. (1994).

Expression of costimulatory molecule CD28 on T-cells in human immunodeficiency virus type 1 infection: functional and clinical coorelations. J. Inf Dis. 169, 730-738.

Brown, W. C., Bissey, L., Logan, K. S., Pedersen, N. C., Elders, J. H., Collisson, E. W. (1991).

Feline immunodeficiency virus infects both $CD4^+$ and $CD8^+$ T-lymphocytes. J. of Virol. 62, 3359-3364.

Buck, C. A. (1992). Immunoglobulin Superfamily: structure function and relationship to other receptor molecules. Semin. Cell Biol. 3, 179-188.

Buelens, C., Willems, F., Delvaux, A., Pierard, G., Delville, J. P., Velu, T., Goldman, M. (1995).

Interleukin 10 differentially regulates B7-1 (CD80) and B7-2 (CD86) expression on human peripheral blood dendritic cells. Eur. J. Immunol. 25, 2668-2675.

Caruso, A., Cantalamessa, A., Licenziati, S., Peroni, L., Prati, E., Martinelli, F., Canaris, A. D., Folghera, S., Gorla, R., Balsari, A. (1994). Expression of CD28 on $CD8^+$ and $CD4^+$ lymphocytes during HIV infection. Scan. J. Immunol. 40, 485-490.

Cerdan, C., Martin, Y., Brailly, H., Courcoul, M., Flavetta, S., Costello, R., Mawas, C., Birg, F., Olive, D. (1991). IL-1 is produced by T lymphocytes activated via the CD2 plus CD28 pathways. J. Immunol. 146, 560-564.

Chen, L., Linsley, P. S., Hellstrom, K. E. (1993). Costimulation of T cells for tumor immunity.

Immunol. Today 14, 483-486.

Chesnut, R. W. and Grey, H. M. (1986). Antigen presentation by B cells and its significance in T-B interactions. Adv. Immunol. 39, 51-59.

Clark, S. J., Saag M. S., Decker, W. D., Campbell, H. S., Roberson, J. L., Veldkamp, P. J. (1991). High titers of cytopathic virus in plasma of patients with symptoms of primary HIV-1 infection. N. Eng. J. Med. 324, 954-960.

Clayberger, C., Lyu, S. C., DeKruyff, R., Parham, P., Krensky, A. M. (1994). Peptides corresponding to the CD8 and CD4 binding domains of HLA molecules block T-lymphocyte immune responses in vitro. J. Immunol. 153, 946-951.

Clevers, H., Alarcon, B., Wileman, T., Terhorst, C. (1988). The T-cell receptor-CD3 complex: A dynamic protein ensemble. Annu. Rev. Immunol. 6, 629-662.

Connor, R. I., Mohri, H., Cao, Y., Ho, D. D. (1993). Increased viral burden and cytopathicity correlate temporally with CD4+T-lymphocyte decline and clinical progression in human immunodeficiency virus type 1-infected individuals. J Virol. 67, 1772-1777.

Cooper, D. A., Tindall, B., Wilson, E. J., Imreie, A. A., Penny, R. (1988). Characterization of T-lymphocyte responses during primary infection with human immunodeficiency virus. J. Inf. Dis. 157, 889-896.

Damle, N. K., Doyle, L. V., Grossmaire, L. S., Ledbetter, J. A. (1988). Differential regulatory signals delivered by antibody binding to the CD28 molecule during the activation of human T lymphocytes. J. Immunol. 140, 1753-1761.

Damle, N. K., Klussman, K., Leytze, G., Myrdal, S., Arruffo, A., Ledbetter, J. A., Linsley, P. S. (1994). Costimulation of lymphocytes with integrin ligands ICAM-1 or VCAM-1 induces functional expression of CTLA-4 a second receptor for B7. J. Immunol. 152, 2686-2697.

Davis, M. M. and Bjorkman, P. K. (1988). T-cell antigen receptor genes and T-cell recognition.

Nature 334, 395-402.

de Boer, M., Kasran, A., Kwekkeboom, J., Walter, H., Vandenberghe, P., Ceuppens, J. L. (1993). Ligation of B7 with CD28/CTLA-4 on T-cells results in CD40 ligand expression, interleukin-4 secretion and efficient help for antibody production by B cells. Eur. J. Immunol. 23, 3120-3125.

deWaal Malefyt, R., Yssel, H., de Vries, J. E. (1993). Direct effects of IL-10 on subsets of human CD4+ T cell clones and resting T cells. Specific inhibition of Il-2 production and proliferation. J. Immunol. 150, 4754-4765.

Ding, L., Linsley, P. S., Huang, L. Y., Germain, R. N., Shevach, E. M. (1993). IL-10 inhibits macrophage costimulatory activity by selectively inhibiting upregulation of B7 expression. J.

Immunol. 151, 1224-1234.

Driscoll, P. C., Cyster, J., Campbell, I., Williams, A. (1991). Structure of domain 1 of rat T-lymphocyte CD2 antigen. Nature 353, 762-765.

Ellis, J. H., Burden, M., Vinogradov, D., Linge, C., Crowe, J. (1996). Interactions of CD80 and CD86 with CD28 and CTLA-4. J. Immunol. 155, 2700-2709.

Englehard, V. H. (1994). Structure of peptides associated with MHC class I molecules. Curr. Op.

Immunol. 6, 13-21.

English, R. V., Nelson, P., Johnson, C. M., Nasisse, M., Tompkins, W. A., Tompkins, M. B. (1994). Development of clinical disease in cats experimentally infected with feline immunodeficiency virus. J. Inf. Dis. 170, 543-552.

Fauci, A. S. and Dale, D. C. (1975). The effect of hydrocortisone on the kinetics of normal human lymphocytes. Blood 46, 235-243.

Fauci, A., Macher, A., Longo, D., Lane, H., Rook, A., Masur, H., Gelmann, E. (1984). Acquired immunodeficiency syndrome: epidemiological, clinical, immunological and therapeutic considerations. Ann. Int. Med. 100, 92-106.

Fong, T. A. and Mosmann, T. R. (1990). Alloreactive murine CD8+ T cell clones secrete the Th1 pattern of cytokines. J Immunol. 144, 1744-1752.

Fouchier, R. A., Meyaard, L., Brouwer, M., Hovenkamp, E., Schuitemaker, H. (1996). Broader tropism and higher cytopathicity for CD4$^+$ T-cells of asyncytium-inducing compared to a non-syncytium-inducing HIV-1 isolate as a mechanism for accelerated CD4$^+$ T cell decline in vivo. Virology 219, 87-95.

Freedman, A. S., Freeman, G., Horowitz, J. C., Daley, J., Nadler, L. M. (1987). A B-cell restricted antigen that identifies preactivated B cells. J. Immunol. 139, 3260-3267.

Freeman G. J., Borriello, F., Hodes, R. J., Reiser, H., Hathcock, K. S., Laszlo, G., McKnight, A.

J., Kim, J., Du, L., Lombard, D. B., Gray, G. S., Nadler, L. M., Sharpe, A. H. (1993).

Uncovering a functional alternative CTLA-4 counter receptor in B7-1 deficient mice. Science 262, 907-909.

Gajewski, T. F., Schell, S. R., Nau, G., Fitch, F. W. (1989). Regulation of T-cell activation:

Differences among T-cell subsets. Immunol Rev. 111, 79-110.

Germain, R. N. (1993). The Biochemistry and cell biology of antigen processing and presentation. Annu. Rev. Immunol. 11, 403-450.

Haffar, O. K., Smithgall, M. D., Bradshaw, J., Brady, W., Damle, N. K., Linsley, P. S. (1993).

Costimulation of T-cell activation and virus production by B7 antigen on activated CD4$^+$ T-cells from human immunodeficiency virus type 1-infected donors. Immunology 90, 11094-11098.

Harlan, D. M., Abe, R., Lee, K. P., June, C. H. (1995). Potential roles of the B7 and CD28 receptor families in autoimmunity and immune evasion. Clin. Immunol. Immunopath. 75, 99-111.

Hodge, J. W., Abrami, S., Schlom, J., Kantor, J. A. (1994). Induction of antitumor immunity by recombinant vaccinia viruses expressing B7-1 or B7-2 costimulatory molecules. Can. Res. 54, 5552-5555.

Hutchcroft, J. E. and Bierer, B. E. (1996). Signaling through CD28/CTLA-4 family receptors. J.

Immunol. 155, 4071-4074.

Jenkins, M. K., Pardoll, D. M., Mizuguchi, J., Quill, H., Schwartz, R. H. (1987). T cell responsiveness in vivo and in vitro: Fine specificity of induction and molecular characterisation of the unresponsive state. Immunol. Rev. 95, 113-135.

June, C. H., Ledbetter, J. H., Linsley, P. S., Thompson, C. B. (1990). Role of the CD28 molecule in T-cell activation. Immunol. Today 11, 211-216.

June, C. H., Bluestone, J. A., Nadler, L. M., Thompson, C. B. (1994). The B7 and CD28 receptor families. Immunol. Today 12, 321-333.

Kozber, D., Moretta, A., Messner, H. A., Moretta, L., Croce, C. M. (1987). Tp44 molecules involved in antigen-independant T cell activation are expressed on human plasma cells. J.

Immunol. 138, 4128-4132.

Kupfer, A. and Singer, S. J. (1989). Cell biology of cytotoxic and helper T-cell functions. Annu.

Rev. Immunol. 7, 309-337.

Landay, A. L., Mackewicz, C. E., Levy, J. A. (1993). An activated CD8+ T cell phenotype coorelates with an anti-HIV activity and assymptomatic clinical status. Clin Immun. Immunopath. 69, 106-116.

Lane, P., Burdet, C., Hubele, S., Scheidegger, D., Muller, U., McConnell, F., Kosco-Vilbois, M. (1994). B cell function in mice transgenic for mCTLA4-H gamma 1: lack of germinal centers correlated with poor affinity maturation and class switching despite normal priming of CD4+ T-cells. J Exp Med. 179, 819-830.

Lanier, L. L., O'Fallon, S., Somoza, C., Phillips, J. H., Linsley, P. S., Okumura, K., Ito, D., Azuma, M. (1995). CD80 (B7) and CD86 (B70) provide similar costimulatory signals for T cell proliferation, cytokine production, and generation of CTL. J. Immunol. 154, 97-105.

Larsen, C. P., Ritchie, S. C., Pearson, T. C., Linsley, P. S., Lowry, R. P. (1992). Functional expression of the costimulatory molecule B7/BB1 in murine dendritic cell populations. J. Exp. Med. 176, 1215-1220.

Leahy, D., Axel, R., Hendrickson, W. (1992). Crystal structure of a soluble form of human T cell counter receptor CD8 at 2.8 resolution. Cell 68, 1145-1162.

Lechler, R. I., Lombardi, G., Batchelor J. R., Reinsmoen N., Bach, F. H. (1990). The molecular basis of alloreactivity. Annu. Rev. Immunol. 10, 83-88.

Lenschow, D. J., Su, G. H-T., Zuckennann, L. A., Nabavi, N., Jellis, C. L., Gray, G. S., Miller, J., Bluestone, J. A. (1993). Expression and functional significance of an additional ligand for CTLA-4. Proc. Nat. Acad. Sci. USA. 90, 11054-11058.

Lenschow, D. J., Walunas, T. L., Bluestone, J. A. (1996). CD28/B7 system of T cell costimulation. Annu. Rev. Immunol. 14 233-258.

Leung, H. T. and Linsley, P. S. (1994). The CD28 costimulatory pathway. Therap. Immunol 1, 217-228.

Lewis, D. E., Ng Tang, D. S., Adu-Oppong, A., Schober, W., Rodgers, J. (1994). Anergy and apoptosis in CD8+ T-cells from HIV infected persons. J. Immunol. 153, 412-420.

Li, Y., McGowan, P., Hellstrom, I., Hellstrom, K. E., Chen, L. (1994). Costimulation of tumor reactive CD4 and CD8 T-lymphocytes by B7 a natural ligand for CD28 can be used to treat established mouse melanoma. J. Immunol. 153, 421-428.

Lindsten, T., Lee, K. P., Harris, E. S., Petryniak, B., Craighead, N., Reynolds, P. J., Lombard, D. B., Freeman, G. J., Nadler, L. M., Gray, G. S. (1993). Characterization of CTLA-4 structure and expression on human T-cells. J. Immunol. 151, 3489-3499.

Linsley, P. S., Brady, W., Urnes, M., Grosmaire, L. S., Damle, N. K., Ledbetter, J. A. (1991a). Binding of the B-cell activation antigen B7 to CD28 costimulates T-cell proliferation and Interleukin-2 mRNA accumulation. J. Exp. Med. 173, 721-730.

Linsley, P. S., Brady, W., Urnes, M., Grosmaire, L. S., Damle, N. K., Ledbetter, J. A. (1991b). CTLA-4 is a second receptor for the B-cell activation antigen B7. J. Exp. Med. 174, 561-569.

Linsley, P. S., Wallace, P. M., Johnson, J., Gibson, M. G., Greene, J. L., Ledbetter, J. A., Singh, C., Tepper, M. A. (1992a). Immunosuppression in vivo by a soluble form of the CTLA-4 T cell activation molecule. Science 257, 792-795.

Linsley, P. S., Greene, J. L., Tan, P., Bradshaw, J., Ledbetter, J. A., Anasetti, C., Damle, N. K. (1992b). Coexpression and functional cooperation of CTLA-4 and CD28 on activated T-lymphocytes. J. Exp. Med. 176, 1595-1604.

Linsley, P. S. and Ledbetter, J. A. (1993a). The role of CD28 receptor during T cell responses to antigen. Ann. Rev. Immunol. 11, 191-212.

Linsley, P. S., Bradshaw, J., Urnes, M., Grosmaire, L., Thompson, C. B. (1993b). CD28 engagement by B7/BB-1 induces transient down-regulation of CD28 synthesis and prolonged unresponsiveness to CD28 signaling. J. Immunol. 150, 3161-3169.

Linsley, P. S., Greene, J. L., Brady, W., Bajorath, J., Ledbetter, J. A., Peach, R. (1994a). Human B7-1 (CD80) and B7-2 (CD86) bind with similar avidities but distinct kinetics to CD28 and CTLA-4 receptors. Immunity 1, 793-801.

Linsley, P. S., Peach, R., Gladstone, P., Bajorath, J. (1994b). Extending the B7 (CD80) gene family. Prot. Sci. 3, 1341-1343.

Linsley, P. S., Ledbetter, J., Peach, R., Bajorath, J. (1995a). CD28/CTLA-4 receptor structure, binding stoichiometry arid aggregation during T cell activation. Res. Immunol. 146, 130-140.

Linsley, P. S., Nadler, S. G., Bajorath, J., Peach, R., Leung, H. T., Rogers, J., Bradshaw, J., Stebbins, M., Leytze, G., Brady, W., Malacko, A. R., Marquardt, H., Shaw, S. (1995b). Binding stoichiometry of the cytotoxic T-lymphocyte-associated molecule-4 (CTLA-4). J. Biol. Chem. 270, 15417-15424.

Littman, D. R. (1987). The structure of the CD4 and CD8 genes. Annu. Rev. Immunol. 5, 561-584.

Liu, C. C., Welsh, C. M., Young, J. D-E. (1995). Perforin: Structure and function. Immunol. Today 16, 194-201.

Liu, Y., Jones, B., Brady, W., Janeway, C. A., Linsley, P. (1992). Murine CD4 T cell growth: B7 and heat stable antigen both participate in co-stimulation. Eur. J. Immunol. 115, 1905-1912.

Lombardi, S., Garzelli, C., Pistello, M., Massi, C., Matteucci, D., Baldinotti, F., Cammarota, G., Da Prato, L., Bandecchi, P., Tozzini, F., Bendinelli, M. (1994). A neutralizing antibody-inducing peptide of the V3 domain of feline immunodeficiency virus envelope glycoprotein does not induce protective immunity. J. Virol. 68, 8374-8379.

Lu, Y., Granelli-Piperno, A., Bjorndahl, J. M., Phillips, C. A., Trevillyan J. M. (1992). CD28-induced T cell activation. Evidence for a protein-tyrosine kinase signal transduction pathway. J Immunol. 149, 24-29.

Luria, S. E. and Darnell, J. E. (1968). "General Virology." New York: John Wiley and Sons, Inc. Lwoff, A. (1957). The concept of virus. J. Gen. Microbiol. 17, 239-253.

Maniatis, T., Fritsch, E. F., and Sambrook, J. (1982). "Molecular Cloning: A Laboratory Manual." New York: Cold Spring Harbor Press.

Martin, P. J., Ledbetter, J. A., Morishita, Y., June, C. H., Beatty, P. J., Hansen, J. A. (1986). A 44 kilodalton cell surface homodimer regulates interleukin 2 production by activated human T lymphocytes. J. Immunol. 136, 3282-3287.

Matasumura, M., Fremont, D. H., Peterson, P. A., Wilson, I. A. (1992). Emerging principles for the recognition of peptide antigens by MHC class I molecules. Science 257, 927-934.

Mescher, M. F. (1992). Surface contact requirements for activation of cytotoxic T-lymphocytes. J. Immunol. 49, 2402-2405.

Minty, A., Chalon, P., Derocq, J. M., Dumont, X., Guillemot, J. C., Kaghad, M., Labit, C., Leplatois, P., Liauzun, P., Miloux, B., Minty, C., Casellas, P., Loison, G., Lupker, J., Shire, D., Ferrara, P., Caput, D., (1993). Interleukin 13 is a new human lymphokine regulating inflammatory and immune responses. Nature 362, 248-250.

Moffett, C. W. and Paden, C. M. (1994). Microglia in the rat neurohypophysis increase expression of class I major histocompatibility antigens following central nervous system injury. J Neuroimmunol. 50, 139-51.

Mosmann, T. and Coffman, R. L. (1989). TH1 and TH2 cells: Different patterns of lymphokine secretion lead to different functional properties. Annu. Rev. Immunol. 7, 145-173.

Nabavi, N., Freeman, G. J., Gault, D., Godfrey, G. N., Nadler, L. M., Glimcher, L. M. (1992). Signaling through the MHC CII cytoplasmic domain is required for antigen presentation and induces B7 expression. Nature 360, 266-268.

Nagata, S. and Golstein, P. (1995). The Fas death factor. Science 267, 1449-1465.

Nickoloff, B. J., Mitra, R. S., Lee, K., Turka, L. A., Greem, J., Thompson, C., Shimizu, Y. (1993). Discordant expression of CD28 ligands BB-1 and B7 on keratinocytes in vitro and psoriatic cells in vivo. Am J. Path. 142, 1029-1040.

Novotney, C., English, R., Housman, J., Davidson, M., Nasisse, M., Jeng, C. R. (1990). Lymphocyte population changes in cats naturally infected with feline immunodeficiency virus. AIDS 4, 1213-1218.

O'Doherty, U., Steinman, R. M., Peng, M., Cameron, P. U., Gezelter, S., Kopeloff, I., Swiggard, W. J., Pope, M., Bhardwaj, N. (1993). Dendritic cells freshly isolated from human blood express CD4 and mature into typical immunostimulatory dendritic cells after culture in monocyte-conditioned media. J. Exp. Med. 178, 1067-1076.

Ozawa, H., Aiba, S., Nakagawa, S., Tagami, H. (1995). Interferon gamma and interleukin 10 inhibit antigen presentation by Langerhan's cells for T helper type 1 cells by suppressing their CD80 (B7-1) expression. Eur. J. Immunol. 26 648-652.

Page, C., Thompson, C., Yacoub, M., Rose, M. (1994). Human endothelial stimulation of allogenic T-cells via a CTLA-4 independent pathway. Trans. Immunol. 2, 342-347.

Peach, R., Bajorath, J., Brady, W., Leytze, G., Greene, J., Naemura, J., Linsley, P. S. (1994). CDR1 and CDR3-analogous regions in CTLA-4 and CD28 determine the binding to B7-1. J. Exp. Med. 180, 2049-2058.

Peach, R., Bajorath, J., Naemura, J., Leytze, G., Greene, J., Aruffo, A., Linsley, P. S. (1995). Both extracellular immunoglobulin-like domains of CD80 contain residues critical for binding T-cell surface receptors CTLA-4 and CD28. J. Biol. Chem. 270, 21181-21187.

Pedersen, N. C., Ho, E., Brown, M. L., Yamamoto, J. K. (1987). Isolation of a T lymphotrophic virus from domestic cats with an immunodeficiency like syndrome. Science 235, 790-793.

Prasad, K. V., Cai Y. C., Raab, M., Duckworth, B., Cantley, L., Shoelson, S. E., Rudd, C. E. (1994). T-cell antigen CD28 interacts with the lipid kinase phosphatidylinositol 3-kinase by a cytoplasmic Tyr(P)-Met-Xaa-Met motif. Proc Natl Acad Sci USA. 91, 2834-2838.

Radvanyi, L. G., Shi, Y., Vaziri, H., Sharma, A., Dhala, R., Mills, G. B., Miller, R. G. (1996). CD28 costimulation inhibits TCR-induced apoptosis during a primary T cell response. J. Immunol. 158, 1788-1798.

Ranheim, E. A. and Kipps, T. J. (1995). Tumor necrosis factor-alpha facilitates induction of CD80 (B7-1) on human B cells by activated T-cells: complex regulation by IL-4, IL-10, and CD40L. Cell. Immunol. 161, 226-235.

Razi-Wolf, Z., Freeman, G., Galvin, F., Benacerraf, B., Nadler, L., Reiser, H. (1992). Expression and function of the murine B7 antigen and the major costimulatory molecule expressed by peritoneal exudate cells. Proc. Nat. Acad. Sci. USA. 89, 4210-4214.

Ronchese, F., Hausmann, B., Hubele, S., Lane, P. (1994). Mice transgenic for a soluble form of murine CTLA-4 show enhanced expansion of antigen-specific CD4+ T-cells and defective antibody production in vivo. J. Exp Med. 179, 809-817.

Rotzschke, O. and Falk, K. (1994). Origin structure and motifs of naturally processed MHC class II ligands. Curr. Op Immunol. 6, 45-51.

Russel, J. H. (1983). Internal disintegration model of cytotoxic lymphocyte induced target damage. Immunol. Rev. 72, 97-118.

Saukkonen, J. J., Kornfield, H., Berman, J. S. (1993). Expansion of a CD8$^+$CD28$^+$ cell population in the blood and lung of HIV-positive patients. JAIDS 11, 1194-1199.

Schattner, E. and Laurence, J. (1994). HIV induced T-lymphocyte depletion. Clin. Lab. Med. 14, 221-227.

Schmittel, A., Scheibenbogen, C., Keilholz, U. (1995). Lipopolysaccharide effectively up-regulates B7-1 (CD80) expression and costimulatory function of human monocytes. Scan. J. Immunol. 42, 701-704.

Schwartz, R. H. (1992). Costimulation of T-lymphocytes: the role of CD28, CTLA-4 and B7/BB1 in interleukin-2 production and immunotherapy. Cell 71, 1065-1068.

Seder, R. A., Germain, R. N., Linsley, P. S., Paul, W. E. (1994). CD28 mediated co-stimulation of IL-2 production plays a critical role in T cell priming for IL-4 and IFNγ production, J. Exp Med. 179, 299-304.

Shahinian, A., Pfeffer, K., Lee, K. P., Kundig, T. M., Kishihara, K., Wakeham, A., Kawai, K., Ohashi, P. S., Thompson, C. B., Mak, T. B. (1993). Differential T cell costimulatory requirements in CD28 deficient mice. Science 261, 609-612.

Sher, A., Gazzinelli, R. T., Oswald, I. P., Clerici, M., Kullberg, M., Pearce, E. J., Berzofsky, J. A., Mosmann, T. R., James, S. L., Morse, H. C. (1992). Role of T-cell derived cytokines in the downregulation of immune responses in parasitic and retroviral infection. Immunol Rev. 127, 183-204.

Siebelink, K. H., Chu, I. H., Rimmelzwaan, G. F., Weijer, K., van Herwijnen, H. R., Knell, P. (1990). Feline Immunodeficiency virus (FIV) infection in the cat as a model for HIV infection in man: FIV induced impairment of immune function. AIDS Res. Hum. Retroviruses 6, 1373-1378.

Siebelink, K. H., Tijhaar, E., Huisman, R. C., Huisman, W., deRonde, A., Darby, I. H., Francis, M. J., Rimmelzwaan, G. F., Osterhaus, A. D. (1995). Enhancement of feline immunodeficiency virus infection after immunization with envelope glycoprotein subunit vaccines. J Virol. 69, 3704-3711.

Singer, S. J. (1992). Intracellular communication and cell:cell adhesion. Science 255, 1671-1674.

Smithgall, M. D., Wong, J. G., Linsley, P. S., Haffar, O. K. (1995). Costimulation of CD4+ T-cells via CD28 modulates human immunodeficiency type 1 infection and replication in vitro. AIDS Res. Hu. Retro. 11, 885-892.

Springer, T. A., Dustin, M. L., Kishimoto, T. K., Marlin, S. D. (1987). The lymphocyte function associated LFA-1, CD2 and LFA-3 molecules: cell adhesion receptors of the immune system. Annu. Rev. Immunol. 5, 223-252.

Springer, T. A. (1990). Adhesion receptors of the immune system. Nature 346, 425-434.

Stack, R. M., Lenschow, D. J., Gray, G. S., Bluestone, J. A., Fitch, F. W. (1994). IL-4 treatment of small splenic B cells induces co-stimulatory molecules B7-1 and B7-2. J. Immunol. 152, 5723-5733.

Symington, F. W., Brady, W., Linsley, P. S. (1993). Expression and function of B7 on human epidermal Langerhan's cells. J. Immunol. 150, 1286-1295.

Taylor, M. K. and Cohen, J. J. (1992). Cell mediated cytotoxicity. Curr. Opin. Immunol. 4, 338-343.

Thomas, R., Davi, L. S., Lipsky, P. E. (1994). Rheumatoid synovium is enriched in mature antigen presenting dendritic cells. J. Immunol. 152, 2613-2623.

Townsend, S. E., and Allison, J. P. (1993). Tumor rejection after direct costimulation of CD8$^+$ T-cells by B7 transfected melanoma cells. Science 259, 368-370.

Turka L. A., Ledbetter, J. A., Lee, K., June, C. H., Thompson, C. B. (1990). CD28 is an inducible T cell surface antigen that transduces a proliferative signal in CD3$^+$ mature thymocytes. J. Immunol. 144, 1646-1653.

Turka, L. A., Linsley, P. S., Paine, R., Schieven, G. L., Thompson, C. B., Ledbetter, J. A. (1991). Signal transduction via CD4, CD8 and CD28 in mature and immature thymocytes. J. Immunol. 146, 1428-1436.

Unanue, E. R. (1984). Antigen presenting function of the macrophage. Annu. Rev. Immunol. 2, 395-428.

van Kooten, C., Rensink, I., Pascual,-Salcedo, D., van Oers, R., Aarden, L. (1991). Monokine production by human T-cells: IL-1 alpha production is limited to memory T-cells. J. Immunol. 146, 2654-2658.

van Seventer, G. A., Shimizu, Y., Shaw, S. (1991). Roles of multiple accessory molecules in T cell activation. Curr. Opin Immunol. 3, 294-303.

Wang, R., Murphy, K. M., Loh, D. Y., Weaver, C., Russell, J. H. (1993). Differential activation of antigen-stimulated silicide and cytokine production pathways in CD4+ T-cells is regulated by the antigen-presenting cell. J Immunol. 150, 3832-42.

Weiss, A. and Littman, D. R. (1994). Signal transduction by lymphocyte antigen receptors. Cell 76, 263-274.

Williams, A. and Barclay, A. (1988). The immunoglobulin superfamily-domains for cell surface recognition. Ann. Rev. Immunol. 6, 381-405.

Windhagen, A., Newcombe, J., Dangond, F., Strand, C., Woodroofe, M. N., Cuzner, M. L., Hafler, D. A. (1995). Expression of costimulatory molecules B7-1 (CD80), B7-2 (CD86) and interleukin 12 in multiple schlerosis lesions. J. Exp. Med. 182, 1985-1996.

Yamamoto, J. K., Hansen, H., Ho, W. E., Morishita, T. Y., Okuda, T., Sawa, T. R. (1989). Epidemiological and clinical aspects of feline immunodeficiency virus infection in cats from the continental United States and Canada and possible mode of transmission. J.A.V.M.A. 194, 213-220.

Yasukawa, M., Inatsuki, A., Kobayashi, Y. (1989). Differential in vitro activation of CD4+CD8- and CD8+CD4-herpes simplex virus-specific human cytotoxic T-cells. J. Immunol. 143, 2051-2057.

Yssel, H., Schneider, P. V., Lanier, L. L. (1993). Interleukin 7 specifically induces B7/BB1 antigen on human cord blood and peripheral blood T-cells and T cell clones. Int. Immunol. 5, 753-759.

Zanussi, S., Simonelli, C., D'Andrea, M., Caffau, C., Clerici, M., Tirelli, U., DePaoli, P. (1996). CD8$^+$ lymphocyte phenotype and cytokine production in long-term non-progressor and in progressor patients with HIV-1 infection. Clin. Exp. Immunol. 105, 220-224.

Zhou, T., Weaver, C., Linsley, P. S., Mountz, J. D. (1994). T-cells of *staphylococcal* enterotoxin B-tolerized autoimmune MRL-lpr/lpr mice require costimulation through the B7-CD28/CTLA-4 pathway for activation and can be reanergized in vivo by stimulation of the T cell receptor in the absence of costimulatory signal. Eur. J. Immunol. 24, 1019-1025.

What is claimed is:

1. An isolated polypeptide of a feline CD86 ligand comprising an amino acid sequence of SEQ ID NO: 6 or a soluble feline CD86 ligand comprising an amino acid sequence of SEQ ID NO: 6, but lacking the transmembrane region.

2. A plasmid vector of B7-2#19-2/011298 (ATCC Accession No. 209821).

3. An isolated host cell, comprising the plasmid vector of claim 2.

4. The host cell of claim 3, wherein the host cell is selected from the group consisting of: *E. coli*, yeast, COS cells, PC12 cells, CHO cells, and GH4C1 cells.

5. A method of producing a polypeptide of claim 1 comprising, culturing an isolated host cell which expresses the polypeptide and recovering the polypeptide so produced.

6. An immunogenic composition comprising the polypeptide of claim 1 and a suitable carrier.

7. The immunogenic composition of claim 6, further comprising an immunogen derived from a pathogen.

8. The immunogenic composition of claim 7, wherein the pathogen is a feline pathogen, a rabies virus, chlamydia, *Toxoplasma gondii, Dirofilaria immitis*, a flea, or a bacterial pathogen.

9. The immunogenic composition of claim 8, wherein the feline pathogen is feline immunodeficiency virus (FIV), feline leukemia virus (FeLV), feline infectious peritonitis virus (FIP), feline panleukopenia virus, feline calicivirus, feline reovirus type 3, feline rotavirus, feline coronavirus, feline syncytial virus, feline sarcoma virus, feline herpesvirus, feline Borna disease virus, or a feline parasite.

* * * * *

SEQUENCE LISTING

<160> NUMBER OF SEQ ID NOS: 83

<210> SEQ ID NO 1
<211> LENGTH: 941
<212> TYPE: DNA
<213> ORGANISM: feline
<220> FEATURE:
<221> NAME/KEY: CDS
<222> LOCATION: (1)..(876)

<400> SEQUENCE: 1

```
atg ggt cac gca gca aag tgg aaa aca cca cta ctg aag cac cca tat      48
Met Gly His Ala Ala Lys Trp Lys Thr Pro Leu Leu Lys His Pro Tyr
 1               5                  10                  15 ccc aag ctc ttt ccg ctc ttg atg cta gct agt ctt ttt tac ttc tgt      96
Pro Lys Leu Phe Pro Leu Leu Met Leu Ala Ser Leu Phe Tyr Phe Cys
            20                  25                  30 tca ggt atc atc cag gtg aac aag aca gtg gaa gaa gta gca gta cta     144
Ser Gly Ile Ile Gln Val Asn Lys Thr Val Glu Glu Val Ala Val Leu
        35                  40                  45 tcc tgt gat tac aac att tcc acc aaa gaa ctg acg gaa att cga atc     192
Ser Cys Asp Tyr Asn Ile Ser Thr Lys Glu Leu Thr Glu Ile Arg Ile
    50                  55                  60 tat tgg caa aag gat gat gaa atg gtg ttg gct gtc atg tct ggc aaa     240
Tyr Trp Gln Lys Asp Asp Glu Met Val Leu Ala Val Met Ser Gly Lys
65                  70                  75                  80 gta caa gtg tgg ccc aag tac aag aac cgc aca ttc act gac gtc acc     288
Val Gln Val Trp Pro Lys Tyr Lys Asn Arg Thr Phe Thr Asp Val Thr
                85                  90                  95 gat aac cac tcc att gtg atc atg gct ctg cgc ctg tca gac aat ggc     336
Asp Asn His Ser Ile Val Ile Met Ala Leu Arg Leu Ser Asp Asn Gly
            100                 105                 110 aaa tac act tgt att att caa aag att gaa aaa ggg tct tac aaa gtg     384
Lys Tyr Thr Cys Ile Ile Gln Lys Ile Glu Lys Gly Ser Tyr Lys Val
        115                 120                 125 aaa cac ctg act tcg gtg atg tta ttg gtc aga gct gac ttc cct gtc     432
Lys His Leu Thr Ser Val Met Leu Leu Val Arg Ala Asp Phe Pro Val
    130                 135                 140 cct agt ata act gat ctt gga aat cca tct cat aac atc aaa agg ata     480
Pro Ser Ile Thr Asp Leu Gly Asn Pro Ser His Asn Ile Lys Arg Ile
145                 150                 155                 160 atg tgc tta act tct gga ggt ttt cca aag cct cac ctc tcc tgg ctg     528
Met Cys Leu Thr Ser Gly Gly Phe Pro Lys Pro His Leu Ser Trp Leu
                165                 170                 175 gaa aat gaa gaa gaa tta aat gcc atc aac aca aca gtt tcc caa gat     576
Glu Asn Glu Glu Glu Leu Asn Ala Ile Asn Thr Thr Val Ser Gln Asp
            180                 185                 190 cct gaa act gag ctc tac act att agc agt gaa ctg gat ttc aat atg     624
Pro Glu Thr Glu Leu Tyr Thr Ile Ser Ser Glu Leu Asp Phe Asn Met
        195                 200                 205 aca aac aac cat agc ttc ctg tgt ctt gtc aag tat gga aac tta cta     672
Thr Asn Asn His Ser Phe Leu Cys Leu Val Lys Tyr Gly Asn Leu Leu
    210                 215                 220 gta tca cag atc ttc aac tgg caa aaa tca gag cca cag cct tct aat     720
Val Ser Gln Ile Phe Asn Trp Gln Lys Ser Glu Pro Gln Pro Ser Asn
225                 230                 235                 240 aat cag ctc tgg atc att atc ctg agc tca gta gta agt ggg att gtt     768
Asn Gln Leu Trp Ile Ile Ile Leu Ser Ser Val Val Ser Gly Ile Val
                245                 250                 255 gtg atc act gca ctt acc tta aga tgc cta gtc cac aga cct gct gca     816
Val Ile Thr Ala Leu Thr Leu Arg Cys Leu Val His Arg Pro Ala Ala
```

```
Val Ile Thr Ala Leu Thr Leu Arg Cys Leu Val His Arg Pro Ala Ala
            260                 265                 270 agg tgg aga caa aga gaa atg ggg aga gcg cgg aaa tgg aaa aga tct       864
Arg Trp Arg Gln Arg Glu Met Gly Arg Ala Arg Lys Trp Lys Arg Ser
        275                 280                 285 cac ctg tct aca tagattctgc agaaccactg tatgcagagc atctggaggt           916
His Leu Ser Thr
        290 agcctcttta gctcttctct actag                                           941

<210> SEQ ID NO 2
<211> LENGTH: 292
<212> TYPE: PRT
<213> ORGANISM: feline

<400> SEQUENCE: 2

Met Gly His Ala Ala Lys Trp Lys Thr Pro Leu Leu Lys His Pro Tyr
1               5                   10                  15

Pro Lys Leu Phe Pro Leu Leu Met Leu Ala Ser Leu Phe Tyr Phe Cys
                20                  25                  30

Ser Gly Ile Ile Gln Val Asn Lys Thr Val Glu Glu Val Ala Val Leu
            35                  40                  45

Ser Cys Asp Tyr Asn Ile Ser Thr Lys Glu Leu Thr Glu Ile Arg Ile
        50                  55                  60

Tyr Trp Gln Lys Asp Asp Glu Met Val Leu Ala Val Met Ser Gly Lys
65                  70                  75                  80

Val Gln Val Trp Pro Lys Tyr Lys Asn Arg Thr Phe Thr Asp Val Thr
                85                  90                  95

Asp Asn His Ser Ile Val Ile Met Ala Leu Arg Leu Ser Asp Asn Gly
            100                 105                 110

Lys Tyr Thr Cys Ile Ile Gln Lys Ile Glu Lys Gly Ser Tyr Lys Val
        115                 120                 125

Lys His Leu Thr Ser Val Met Leu Leu Val Arg Ala Asp Phe Pro Val
    130                 135                 140

Pro Ser Ile Thr Asp Leu Gly Asn Pro Ser His Asn Ile Lys Arg Ile
145                 150                 155                 160

Met Cys Leu Thr Ser Gly Gly Phe Pro Lys Pro His Leu Ser Trp Leu
                165                 170                 175

Glu Asn Glu Glu Glu Leu Asn Ala Ile Asn Thr Thr Val Ser Gln Asp
            180                 185                 190

Pro Glu Thr Glu Leu Tyr Thr Ile Ser Ser Glu Leu Asp Phe Asn Met
        195                 200                 205

Thr Asn Asn His Ser Phe Leu Cys Leu Val Lys Tyr Gly Asn Leu Leu
    210                 215                 220

Val Ser Gln Ile Phe Asn Trp Gln Lys Ser Glu Pro Gln Pro Ser Asn
225                 230                 235                 240

Asn Gln Leu Trp Ile Ile Ile Leu Ser Ser Val Val Ser Gly Ile Val
                245                 250                 255

Val Ile Thr Ala Leu Thr Leu Arg Cys Leu Val His Arg Pro Ala Ala
            260                 265                 270

Arg Trp Arg Gln Arg Glu Met Gly Arg Ala Arg Lys Trp Lys Arg Ser
        275                 280                 285

His Leu Ser Thr
    290

<210> SEQ ID NO 3
```

<211> LENGTH: 879
<212> TYPE: DNA
<213> ORGANISM: feline
<220> FEATURE:
<221> NAME/KEY: CDS
<222> LOCATION: (1)..(876)

<400> SEQUENCE: 3

| | | | | | | | | | | | | | | | | |
|---|---|---|---|---|---|---|---|---|---|---|---|---|---|---|---|---|
| atg | ggt | cac | gca | gca | aag | tgg | aaa | aca | cca | cta | ctg | aag | cac | cca | tat | 48 |
| Met | Gly | His | Ala | Ala | Lys | Trp | Lys | Thr | Pro | Leu | Leu | Lys | His | Pro | Tyr | |
| 1 | | | | 5 | | | | | 10 | | | | | 15 | | |
| ccc | aag | ctc | ttt | ccg | ctc | ttg | atg | cta | gct | agt | ctt | ttt | tac | ttc | tgt | 96 |
| Pro | Lys | Leu | Phe | Pro | Leu | Leu | Met | Leu | Ala | Ser | Leu | Phe | Tyr | Phe | Cys | |
| | | | 20 | | | | | 25 | | | | | 30 | | | |
| tca | ggt | atc | atc | cag | gtg | aac | aag | aca | gtg | gaa | gaa | gta | gca | gta | cta | 144 |
| Ser | Gly | Ile | Ile | Gln | Val | Asn | Lys | Thr | Val | Glu | Glu | Val | Ala | Val | Leu | |
| | | 35 | | | | | 40 | | | | | 45 | | | | |
| tcc | tgt | gat | tac | aac | att | tcc | acc | aaa | gaa | ctg | acg | gaa | att | cga | atc | 192 |
| Ser | Cys | Asp | Tyr | Asn | Ile | Ser | Thr | Lys | Glu | Leu | Thr | Glu | Ile | Arg | Ile | |
| | 50 | | | | | 55 | | | | | 60 | | | | | |
| tat | tgg | caa | aag | gat | gat | gaa | atg | gtg | ttg | gct | gtc | atg | tct | ggc | aaa | 240 |
| Tyr | Trp | Gln | Lys | Asp | Asp | Glu | Met | Val | Leu | Ala | Val | Met | Ser | Gly | Lys | |
| 65 | | | | | 70 | | | | | 75 | | | | | 80 | |
| gta | caa | gtg | tgg | ccc | aag | tac | aag | aac | cgc | aca | ttc | act | gac | gtc | acc | 288 |
| Val | Gln | Val | Trp | Pro | Lys | Tyr | Lys | Asn | Arg | Thr | Phe | Thr | Asp | Val | Thr | |
| | | | | 85 | | | | | 90 | | | | | 95 | | |
| gat | aac | cac | tcc | att | gtg | atc | atg | gct | ctg | cgc | ctg | tca | gac | aat | ggc | 336 |
| Asp | Asn | His | Ser | Ile | Val | Ile | Met | Ala | Leu | Arg | Leu | Ser | Asp | Asn | Gly | |
| | | | 100 | | | | | 105 | | | | | 110 | | | |
| aaa | tac | act | tgt | atc | att | caa | aag | att | caa | aaa | ggg | tct | tac | aaa | gtg | 384 |
| Lys | Tyr | Thr | Cys | Ile | Ile | Gln | Lys | Ile | Gln | Lys | Gly | Ser | Tyr | Lys | Val | |
| | | 115 | | | | | 120 | | | | | 125 | | | | |
| aaa | cac | ctg | act | tcg | gtg | atg | tta | ttg | gtc | aga | gct | gac | ttc | cct | gtc | 432 |
| Lys | His | Leu | Thr | Ser | Val | Met | Leu | Leu | Val | Arg | Ala | Asp | Phe | Pro | Val | |
| 130 | | | | | 135 | | | | | 140 | | | | | | |
| cct | agt | ata | act | gat | ctt | gga | aat | cca | tct | cat | aac | atc | aaa | agg | ata | 480 |
| Pro | Ser | Ile | Thr | Asp | Leu | Gly | Asn | Pro | Ser | His | Asn | Ile | Lys | Arg | Ile | |
| 145 | | | | | 150 | | | | | 155 | | | | | 160 | |
| atg | tgc | tta | act | tct | gga | ggt | ttt | cca | aag | cct | cac | ctc | tcc | tgg | ctg | 528 |
| Met | Cys | Leu | Thr | Ser | Gly | Gly | Phe | Pro | Lys | Pro | His | Leu | Ser | Trp | Leu | |
| | | | | 165 | | | | | 170 | | | | | 175 | | |
| gaa | aat | gaa | gaa | gaa | tta | aat | gcc | atc | aac | aca | aca | gtt | tcc | caa | gat | 576 |
| Glu | Asn | Glu | Glu | Glu | Leu | Asn | Ala | Ile | Asn | Thr | Thr | Val | Ser | Gln | Asp | |
| | | | 180 | | | | | 185 | | | | | 190 | | | |
| cct | gaa | act | gag | ctc | tac | act | att | agc | agt | gaa | ctg | gat | ttc | aat | atg | 624 |
| Pro | Glu | Thr | Glu | Leu | Tyr | Thr | Ile | Ser | Ser | Glu | Leu | Asp | Phe | Asn | Met | |
| | | 195 | | | | | 200 | | | | | 205 | | | | |
| aca | aac | aac | cat | agc | ttc | ctg | tgt | ctt | gtc | aag | tat | gga | aac | tta | ata | 672 |
| Thr | Asn | Asn | His | Ser | Phe | Leu | Cys | Leu | Val | Lys | Tyr | Gly | Asn | Leu | Ile | |
| | 210 | | | | | 215 | | | | | 220 | | | | | |
| gta | tca | cag | atc | ttc | aac | tgg | caa | aaa | tca | gag | cca | cag | cct | tct | aat | 720 |
| Val | Ser | Gln | Ile | Phe | Asn | Trp | Gln | Lys | Ser | Glu | Pro | Gln | Pro | Ser | Asn | |
| 225 | | | | | 230 | | | | | 235 | | | | | 240 | |
| aat | cag | ctc | tgg | atc | att | atc | ctg | agc | tca | gta | gta | agt | ggg | att | gtt | 768 |
| Asn | Gln | Leu | Trp | Ile | Ile | Ile | Leu | Ser | Ser | Val | Val | Ser | Gly | Ile | Val | |
| | | | | 245 | | | | | 250 | | | | | 255 | | |
| gtg | atc | act | gca | ctt | acc | tta | aga | tgc | cta | gtc | cac | aga | cct | gct | gca | 816 |
| Val | Ile | Thr | Ala | Leu | Thr | Leu | Arg | Cys | Leu | Val | His | Arg | Pro | Ala | Ala | |
| | | | 260 | | | | | 265 | | | | | 270 | | | |
| agg | tgg | aga | caa | aga | gaa | atg | ggg | aga | gcg | cgg | aaa | tgg | aaa | aga | tct | 864 |
| Arg | Trp | Arg | Gln | Arg | Glu | Met | Gly | Arg | Ala | Arg | Lys | Trp | Lys | Arg | Ser | |
| | | 275 | | | | | 280 | | | | | 285 | | | | |

```
cac ctg tct aca tag                                                        879
His Leu Ser Thr
    290
```

<210> SEQ ID NO 4
<211> LENGTH: 292
<212> TYPE: PRT
<213> ORGANISM: feline

<400> SEQUENCE: 4

```
Met Gly His Ala Ala Lys Trp Lys Thr Pro Leu Leu Lys His Pro Tyr
1               5                   10                  15

Pro Lys Leu Phe Pro Leu Leu Met Leu Ala Ser Leu Phe Tyr Phe Cys
            20                  25                  30

Ser Gly Ile Ile Gln Val Asn Lys Thr Val Glu Glu Val Ala Val Leu
        35                  40                  45

Ser Cys Asp Tyr Asn Ile Ser Thr Lys Glu Leu Thr Glu Ile Arg Ile
    50                  55                  60

Tyr Trp Gln Lys Asp Asp Glu Met Val Leu Ala Val Met Ser Gly Lys
65                  70                  75                  80

Val Gln Val Trp Pro Lys Tyr Lys Asn Arg Thr Phe Thr Asp Val Thr
                85                  90                  95

Asp Asn His Ser Ile Val Ile Met Ala Leu Arg Leu Ser Asp Asn Gly
            100                 105                 110

Lys Tyr Thr Cys Ile Ile Gln Lys Ile Gln Lys Gly Ser Tyr Lys Val
        115                 120                 125

Lys His Leu Thr Ser Val Met Leu Leu Val Arg Ala Asp Phe Pro Val
    130                 135                 140

Pro Ser Ile Thr Asp Leu Gly Asn Pro Ser His Asn Ile Lys Arg Ile
145                 150                 155                 160

Met Cys Leu Thr Ser Gly Gly Phe Pro Lys Pro His Leu Ser Trp Leu
                165                 170                 175

Glu Asn Glu Glu Glu Leu Asn Ala Ile Asn Thr Thr Val Ser Gln Asp
            180                 185                 190

Pro Glu Thr Glu Leu Tyr Thr Ile Ser Ser Glu Leu Asp Phe Asn Met
        195                 200                 205

Thr Asn Asn His Ser Phe Leu Cys Leu Val Lys Tyr Gly Asn Leu Ile
    210                 215                 220

Val Ser Gln Ile Phe Asn Trp Gln Lys Ser Glu Pro Gln Pro Ser Asn
225                 230                 235                 240

Asn Gln Leu Trp Ile Ile Ile Leu Ser Ser Val Val Ser Gly Ile Val
                245                 250                 255

Val Ile Thr Ala Leu Thr Leu Arg Cys Leu Val His Arg Pro Ala Ala
            260                 265                 270

Arg Trp Arg Gln Arg Glu Met Gly Arg Ala Arg Lys Trp Lys Arg Ser
        275                 280                 285

His Leu Ser Thr
    290
```

<210> SEQ ID NO 5
<211> LENGTH: 1080
<212> TYPE: DNA
<213> ORGANISM: feline
<220> FEATURE:
<221> NAME/KEY: CDS
<222> LOCATION: (63)..(1052)

<400> SEQUENCE: 5

```
gtttctgtgt tcctcgggaa tgtcactgag cttatacatc tggtctctgg gagctgcagt         60 gg atg ggc att tgt gac agc act atg gga ctg agt cac act ctc ctt          107
   Met Gly Ile Cys Asp Ser Thr Met Gly Leu Ser His Thr Leu Leu
   1               5                   10                  15 gtg atg gcc ctc ctg ctc tct ggt gtt tct tcc atg aag agt caa gca         155
Val Met Ala Leu Leu Leu Ser Gly Val Ser Ser Met Lys Ser Gln Ala
                    20                  25                  30 tat ttc aac aag act gga gaa ctg cca tgc cat ttt aca aac tct caa         203
Tyr Phe Asn Lys Thr Gly Glu Leu Pro Cys His Phe Thr Asn Ser Gln
                35                  40                  45 aac ata agc ctg gat gag ctg gta gta ttt tgg cag gac cag gat aag         251
Asn Ile Ser Leu Asp Glu Leu Val Val Phe Trp Gln Asp Gln Asp Lys
            50                  55                  60 ctg gtt ctg tat gag ata ttc aga ggc aaa gag aac cct caa aat gtt         299
Leu Val Leu Tyr Glu Ile Phe Arg Gly Lys Glu Asn Pro Gln Asn Val
65                  70                  75 cat ctc aaa tat aag ggc cgt aca agc ttt gac aag gac aac tgg acc         347
His Leu Lys Tyr Lys Gly Arg Thr Ser Phe Asp Lys Asp Asn Trp Thr
80                  85                  90                  95 ctg aga ctc cac aat gtt cag atc aag gac aag ggc aca tat cac tgt         395
Leu Arg Leu His Asn Val Gln Ile Lys Asp Lys Gly Thr Tyr His Cys
                    100                 105                 110 ttc att cat tat aaa ggg ccc aaa gga cta gtt ccc atg cac caa atg         443
Phe Ile His Tyr Lys Gly Pro Lys Gly Leu Val Pro Met His Gln Met
                115                 120                 125 agt tct gac cta tca gtg ctt gct aac ttc agt caa cct gaa ata aca         491
Ser Ser Asp Leu Ser Val Leu Ala Asn Phe Ser Gln Pro Glu Ile Thr
            130                 135                 140 gta act tct aat aga aca gaa aat tct ggc atc ata aat ttg acc tgc         539
Val Thr Ser Asn Arg Thr Glu Asn Ser Gly Ile Ile Asn Leu Thr Cys
145                 150                 155 tca tct ata caa ggt tac cca gaa cct aag gag atg tat ttt cag cta         587
Ser Ser Ile Gln Gly Tyr Pro Glu Pro Lys Glu Met Tyr Phe Gln Leu
160                 165                 170                 175 aac act gag aat tca act act aag tat gat act gtc atg aag aaa tct         635
Asn Thr Glu Asn Ser Thr Thr Lys Tyr Asp Thr Val Met Lys Lys Ser
                180                 185                 190 caa aat aat gtg aca gaa ctg tac aac gtt tct atc agc ttg cct ttt         683
Gln Asn Asn Val Thr Glu Leu Tyr Asn Val Ser Ile Ser Leu Pro Phe
                195                 200                 205 tca gtc cct gaa gca cac aat gtg agc gtc ttt tgt gcc ctg aaa ctg         731
Ser Val Pro Glu Ala His Asn Val Ser Val Phe Cys Ala Leu Lys Leu
            210                 215                 220 gag aca ctg gag atg ctg ctc tcc cta cct ttc aat ata gat gca caa         779
Glu Thr Leu Glu Met Leu Leu Ser Leu Pro Phe Asn Ile Asp Ala Gln
225                 230                 235 cct aag gat aaa gac cct gaa caa ggc cac ttc ctc tgg att gcg gct         827
Pro Lys Asp Lys Asp Pro Glu Gln Gly His Phe Leu Trp Ile Ala Ala
240                 245                 250                 255 gta ctt gta atg ttt gtt gtt ttt tgt ggg atg gtg tcc ttt aaa aca         875
Val Leu Val Met Phe Val Val Phe Cys Gly Met Val Ser Phe Lys Thr
                260                 265                 270 cta agg aaa agg aag aag aag cag cct ggc ccc tct cat gaa tgt gaa         923
Leu Arg Lys Arg Lys Lys Lys Gln Pro Gly Pro Ser His Glu Cys Glu
                275                 280                 285 acc atc aaa agg gag aga aaa gag agc aaa cag acc aac gaa aga gta         971
Thr Ile Lys Arg Glu Arg Lys Glu Ser Lys Gln Thr Asn Glu Arg Val
                290                 295                 300 cca tac cac gta cct gag aga tct gat gaa gcc cag tgt gtt aac att        1019
Pro Tyr His Val Pro Glu Arg Ser Asp Glu Ala Gln Cys Val Asn Ile
```

```
Pro Tyr His Val Pro Glu Arg Ser Asp Glu Ala Gln Cys Val Asn Ile
        305             310             315 ttg aag aca gcc tca ggg gac aaa aat cag tag gaaaatggtg gcttggcgtg      1072
Leu Lys Thr Ala Ser Gly Asp Lys Asn Gln
320             325 ctgacaat                                                                1080

<210> SEQ ID NO 6
<211> LENGTH: 329
<212> TYPE: PRT
<213> ORGANISM: feline

<400> SEQUENCE: 6

Met Gly Ile Cys Asp Ser Thr Met Gly Leu Ser His Thr Leu Leu Val
1               5                   10                  15

Met Ala Leu Leu Leu Ser Gly Val Ser Ser Met Lys Ser Gln Ala Tyr
                20                  25                  30

Phe Asn Lys Thr Gly Glu Leu Pro Cys His Phe Thr Asn Ser Gln Asn
            35                  40                  45

Ile Ser Leu Asp Glu Leu Val Val Phe Trp Gln Asp Gln Asp Lys Leu
        50                  55                  60

Val Leu Tyr Glu Ile Phe Arg Gly Lys Glu Asn Pro Gln Asn Val His
65                  70                  75                  80

Leu Lys Tyr Lys Gly Arg Thr Ser Phe Asp Lys Asp Asn Trp Thr Leu
                85                  90                  95

Arg Leu His Asn Val Gln Ile Lys Asp Lys Gly Thr Tyr His Cys Phe
            100                 105                 110

Ile His Tyr Lys Gly Pro Lys Gly Leu Val Pro Met His Gln Met Ser
        115                 120                 125

Ser Asp Leu Ser Val Leu Ala Asn Phe Ser Gln Pro Glu Ile Thr Val
130                 135                 140

Thr Ser Asn Arg Thr Glu Asn Ser Gly Ile Ile Asn Leu Thr Cys Ser
145                 150                 155                 160

Ser Ile Gln Gly Tyr Pro Glu Pro Lys Glu Met Tyr Phe Gln Leu Asn
                165                 170                 175

Thr Glu Asn Ser Thr Thr Lys Tyr Asp Thr Val Met Lys Lys Ser Gln
            180                 185                 190

Asn Asn Val Thr Glu Leu Tyr Asn Val Ser Ile Ser Leu Pro Phe Ser
        195                 200                 205

Val Pro Glu Ala His Asn Val Ser Val Phe Cys Ala Leu Lys Leu Glu
210                 215                 220

Thr Leu Glu Met Leu Leu Ser Leu Pro Phe Asn Ile Asp Ala Gln Pro
225                 230                 235                 240

Lys Asp Lys Asp Pro Glu Gln Gly His Phe Leu Trp Ile Ala Ala Val
                245                 250                 255

Leu Val Met Phe Val Val Phe Cys Gly Met Val Ser Phe Lys Thr Leu
            260                 265                 270

Arg Lys Arg Lys Lys Lys Gln Pro Gly Pro Ser His Glu Cys Glu Thr
        275                 280                 285

Ile Lys Arg Glu Arg Lys Glu Ser Lys Gln Thr Asn Glu Arg Val Pro
        290                 295                 300

Tyr His Val Pro Glu Arg Ser Asp Glu Ala Gln Cys Val Asn Ile Leu
305                 310                 315                 320

Lys Thr Ala Ser Gly Asp Lys Asn Gln
                325
```

```
<210> SEQ ID NO 7
<211> LENGTH: 688
<212> TYPE: DNA
<213> ORGANISM: feline
<220> FEATURE:
<221> NAME/KEY: CDS
<222> LOCATION: (1)..(663)

<400> SEQUENCE: 7 atg atc ctc agg ctg ctt ctg gct ctc aac ttc ttc ccc tca att caa      48
Met Ile Leu Arg Leu Leu Leu Ala Leu Asn Phe Phe Pro Ser Ile Gln
1               5                   10                  15 gta aca gaa aac aag att ttg gtg aag cag ttg ccc agg ctt gtg gtg      96
Val Thr Glu Asn Lys Ile Leu Val Lys Gln Leu Pro Arg Leu Val Val
            20                  25                  30 tac aac aat gag gtc aac ctt agc tgc aag tac act cac aac ttc ttc     144
Tyr Asn Asn Glu Val Asn Leu Ser Cys Lys Tyr Thr His Asn Phe Phe
        35                  40                  45 tca aag gag ttc cgg gca tcc ctt tat aag gga gta gat agt gct gtg     192
Ser Lys Glu Phe Arg Ala Ser Leu Tyr Lys Gly Val Asp Ser Ala Val
    50                  55                  60 gaa gtc tgc gtt gtg aat gga aat tac tcc cat cag cct cag ttc tac     240
Glu Val Cys Val Val Asn Gly Asn Tyr Ser His Gln Pro Gln Phe Tyr
65                  70                  75                  80 tca agt aca gga ttc gac tgt gat ggg aaa ttg ggc aat gaa aca gtg     288
Ser Ser Thr Gly Phe Asp Cys Asp Gly Lys Leu Gly Asn Glu Thr Val
                85                  90                  95 aca ttc tac ctc cga aat ttg ttt gtt aac caa acg gat att tac ttc     336
Thr Phe Tyr Leu Arg Asn Leu Phe Val Asn Gln Thr Asp Ile Tyr Phe
            100                 105                 110 tgc aaa att gaa gtc atg tat cca cct cct tac ata gac aat gag aag     384
Cys Lys Ile Glu Val Met Tyr Pro Pro Pro Tyr Ile Asp Asn Glu Lys
        115                 120                 125 agc aat ggg acc att atc cac gtg aaa gag aaa cat ctt tgt cca gct     432
Ser Asn Gly Thr Ile Ile His Val Lys Glu Lys His Leu Cys Pro Ala
    130                 135                 140 cag ctg tct cct gaa tct tcc aag cca ttt tgg gca ctg gtg gtg gtt     480
Gln Leu Ser Pro Glu Ser Ser Lys Pro Phe Trp Ala Leu Val Val Val
145                 150                 155                 160 ggt gga atc cta ggt ttc tac agc ttg cta gca aca gtg gct ctt ggt     528
Gly Gly Ile Leu Gly Phe Tyr Ser Leu Leu Ala Thr Val Ala Leu Gly
                165                 170                 175 gct tgc tgg atg aag acc aag agg agt agg atc ctt cag agt gac tat     576
Ala Cys Trp Met Lys Thr Lys Arg Ser Arg Ile Leu Gln Ser Asp Tyr
            180                 185                 190 atg aac atg acc ccc cgg agg cca ggg ccc acc cga agg cac tac caa     624
Met Asn Met Thr Pro Arg Arg Pro Gly Pro Thr Arg Arg His Tyr Gln
        195                 200                 205 cct tac gcc cca gca cgc gac ttt gcg gca tac cgt tcc tgacatggac     673
Pro Tyr Ala Pro Ala Arg Asp Phe Ala Ala Tyr Arg Ser
    210                 215                 220 ccctatccag aagcc                                                    688

<210> SEQ ID NO 8
<211> LENGTH: 221
<212> TYPE: PRT
<213> ORGANISM: feline

<400> SEQUENCE: 8

Met Ile Leu Arg Leu Leu Leu Ala Leu Asn Phe Phe Pro Ser Ile Gln
1               5                   10                  15
```

-continued

```
Val Thr Glu Asn Lys Ile Leu Val Lys Gln Leu Pro Arg Leu Val Val
         20                  25                  30

Tyr Asn Asn Glu Val Asn Leu Ser Cys Lys Tyr Thr His Asn Phe Phe
             35                  40                  45

Ser Lys Glu Phe Arg Ala Ser Leu Tyr Lys Gly Val Asp Ser Ala Val
 50                  55                  60

Glu Val Cys Val Val Asn Gly Asn Tyr Ser His Gln Pro Gln Phe Tyr
 65                  70                  75                  80

Ser Ser Thr Gly Phe Asp Cys Asp Gly Lys Leu Gly Asn Glu Thr Val
                 85                  90                  95

Thr Phe Tyr Leu Arg Asn Leu Phe Val Asn Gln Thr Asp Ile Tyr Phe
            100                 105                 110

Cys Lys Ile Glu Val Met Tyr Pro Pro Tyr Ile Asp Asn Glu Lys
        115                 120                 125

Ser Asn Gly Thr Ile Ile His Val Lys Glu Lys His Leu Cys Pro Ala
130                 135                 140

Gln Leu Ser Pro Glu Ser Ser Lys Pro Phe Trp Ala Leu Val Val Val
145                 150                 155                 160

Gly Gly Ile Leu Gly Phe Tyr Ser Leu Leu Ala Thr Val Ala Leu Gly
                165                 170                 175

Ala Cys Trp Met Lys Thr Lys Arg Ser Arg Ile Leu Gln Ser Asp Tyr
            180                 185                 190

Met Asn Met Thr Pro Arg Arg Pro Gly Pro Thr Arg His Tyr Gln
        195                 200                 205

Pro Tyr Ala Pro Ala Arg Asp Phe Ala Ala Tyr Arg Ser
210                 215                 220
```

<210> SEQ ID NO 9
<211> LENGTH: 749
<212> TYPE: DNA
<213> ORGANISM: feline
<220> FEATURE:
<221> NAME/KEY: CDS
<222> LOCATION: (27)..(698)

<400> SEQUENCE: 9

```
aacctgaaca ctgctcccat aaagcc atg gct tgc ttt gga ttc cgg agg cat        53
                        Met Ala Cys Phe Gly Phe Arg Arg His
                         1               5 ggg gct cag ctg gac ctg gct tct agg acc tgg ccc tgc act gct ctg       101
Gly Ala Gln Leu Asp Leu Ala Ser Arg Thr Trp Pro Cys Thr Ala Leu
 10              15                  20                  25 ttt tct ctt ctc ttt atc ccc gtc ttc tcc aaa ggg atg cat gtg gcc       149
Phe Ser Leu Leu Phe Ile Pro Val Phe Ser Lys Gly Met His Val Ala
             30                  35                  40 cac cct gca gtg gtg ctg gcc agc agc cga ggt gtc gcc agc ttc gtg       197
His Pro Ala Val Val Leu Ala Ser Ser Arg Gly Val Ala Ser Phe Val
         45                  50                  55 tgt gaa tat ggg tct tca ggc aat gcc gcc aaa ttc cga gtg act gtg       245
Cys Glu Tyr Gly Ser Ser Gly Asn Ala Ala Lys Phe Arg Val Thr Val
     60                  65                  70 ctg agg caa act ggc agc caa atg act gaa gtc tgt gct gcg aca tac       293
Leu Arg Gln Thr Gly Ser Gln Met Thr Glu Val Cys Ala Ala Thr Tyr
 75                  80                  85 aca gtg gag aat gag ttg gcc ttc cta aat gat tcc acc tgc act ggc       341
Thr Val Glu Asn Glu Leu Ala Phe Leu Asn Asp Ser Thr Cys Thr Gly
 90                  95                 100                 105 atc tcc agc gga aac aaa gtg aac ctc acc atc caa ggg ttg agg gcc       389
Ile Ser Ser Gly Asn Lys Val Asn Leu Thr Ile Gln Gly Leu Arg Ala
```

```
                     110                 115                  120
atg gac acg gga ctc tac atc tgc aag gtg gag ctc atg tac cca cca         437
Met Asp Thr Gly Leu Tyr Ile Cys Lys Val Glu Leu Met Tyr Pro Pro
            125                 130                  135 ccc tac tat gca ggc atg ggc aat gga acc cag att tat gtc atc gat         485
Pro Tyr Tyr Ala Gly Met Gly Asn Gly Thr Gln Ile Tyr Val Ile Asp
            140                 145                  150 cct gaa cct tgc cca gat tct gac ttc ctc ctc tgg atc ctc gca gca         533
Pro Glu Pro Cys Pro Asp Ser Asp Phe Leu Leu Trp Ile Leu Ala Ala
    155                 160                  165 gtc agt tca gga ttg ttt ttt tat agc ttc ctt atc aca gct gtt tct         581
Val Ser Ser Gly Leu Phe Phe Tyr Ser Phe Leu Ile Thr Ala Val Ser
170                 175                  180                  185 ttg agc aaa atg cta aag aaa aga agc cct ctt act aca ggg gtc tat         629
Leu Ser Lys Met Leu Lys Lys Arg Ser Pro Leu Thr Thr Gly Val Tyr
                190                  195                  200 gtg aaa atg ccc cca aca gag cca gaa tgt gaa aag caa ttt cag cct         677
Val Lys Met Pro Pro Thr Glu Pro Glu Cys Glu Lys Gln Phe Gln Pro
            205                 210                  215 tat ttt att ccc atc aat tga cacaccgtta tgaagaagga agaacactgt            728
Tyr Phe Ile Pro Ile Asn
            220 ccaatttcta agagctgagg c                                                 749

<210> SEQ ID NO 10
<211> LENGTH: 223
<212> TYPE: PRT
<213> ORGANISM: feline

<400> SEQUENCE: 10

Met Ala Cys Phe Gly Phe Arg Arg His Gly Ala Gln Leu Asp Leu Ala
1               5                   10                  15

Ser Arg Thr Trp Pro Cys Thr Ala Leu Phe Ser Leu Leu Phe Ile Pro
            20                  25                  30

Val Phe Ser Lys Gly Met His Val Ala His Pro Ala Val Val Leu Ala
        35                  40                  45

Ser Ser Arg Gly Val Ala Ser Phe Val Cys Glu Tyr Gly Ser Ser Gly
    50                  55                  60

Asn Ala Ala Lys Phe Arg Val Thr Val Leu Arg Gln Thr Gly Ser Gln
65                  70                  75                  80

Met Thr Glu Val Cys Ala Ala Thr Tyr Thr Val Glu Asn Glu Leu Ala
                85                  90                  95

Phe Leu Asn Asp Ser Thr Cys Thr Gly Ile Ser Ser Gly Asn Lys Val
            100                 105                 110

Asn Leu Thr Ile Gln Gly Leu Arg Ala Met Asp Thr Gly Leu Tyr Ile
        115                 120                 125

Cys Lys Val Glu Leu Met Tyr Pro Pro Tyr Tyr Ala Gly Met Gly
    130                 135                 140

Asn Gly Thr Gln Ile Tyr Val Ile Asp Pro Glu Pro Cys Pro Asp Ser
145                 150                 155                 160

Asp Phe Leu Leu Trp Ile Leu Ala Ala Val Ser Ser Gly Leu Phe Phe
                165                 170                 175

Tyr Ser Phe Leu Ile Thr Ala Val Ser Leu Ser Lys Met Leu Lys Lys
            180                 185                 190

Arg Ser Pro Leu Thr Thr Gly Val Tyr Val Lys Met Pro Pro Thr Glu
        195                 200                 205

Pro Glu Cys Glu Lys Gln Phe Gln Pro Tyr Phe Ile Pro Ile Asn
```

<210> SEQ ID NO 11
<211> LENGTH: 40
<212> TYPE: DNA
<213> ORGANISM: feline

<400> SEQUENCE: 11
cgcggatccg caccatgggt cacgcagcaa agtggaaaac        40

<210> SEQ ID NO 12
<211> LENGTH: 25
<212> TYPE: DNA
<213> ORGANISM: feline

<400> SEQUENCE: 12
cctagtagag aagagctaaa gaggc        25

<210> SEQ ID NO 13
<211> LENGTH: 33
<212> TYPE: DNA
<213> ORGANISM: feline

<400> SEQUENCE: 13
cgcggatcca ccggtagcac aatgatcctc agg        33

<210> SEQ ID NO 14
<211> LENGTH: 31
<212> TYPE: DNA
<213> ORGANISM: feline

<400> SEQUENCE: 14
cgcggatcct ctggataggg gtccatgtca g        31

<210> SEQ ID NO 15
<211> LENGTH: 24
<212> TYPE: DNA
<213> ORGANISM: feline

<400> SEQUENCE: 15
atggctygcc ttggattyca gmgg        24

<210> SEQ ID NO 16
<211> LENGTH: 27
<212> TYPE: DNA
<213> ORGANISM: feline

<400> SEQUENCE: 16
tcaattratr ggataaaat aaggctg        27

<210> SEQ ID NO 17
<211> LENGTH: 24
<212> TYPE: DNA
<213> ORGANISM: feline

<400> SEQUENCE: 17
tgttgggttt yrctctrcty cctg        24

<210> SEQ ID NO 18
<211> LENGTH: 24
<212> TYPE: DNA
<213> ORGANISM: feline

<400> SEQUENCE: 18
gcatagtagg gtggtgggta catg                                          24

<210> SEQ ID NO 19
<211> LENGTH: 24
<212> TYPE: DNA
<213> ORGANISM: feline

<400> SEQUENCE: 19
tgttgggttt yrctctrcty cctg                                          24

<210> SEQ ID NO 20
<211> LENGTH: 20
<212> TYPE: DNA
<213> ORGANISM: feline

<400> SEQUENCE: 20
acatgagctc caccttgcag                                               20

<210> SEQ ID NO 21
<211> LENGTH: 27
<212> TYPE: DNA
<213> ORGANISM: feline

<400> SEQUENCE: 21
ccatcctaat acgactcact atagggc                                       27

<210> SEQ ID NO 22
<211> LENGTH: 24
<212> TYPE: DNA
<213> ORGANISM: feline

<400> SEQUENCE: 22
gtgaatatgg gtcttcaggc aatg                                          24

<210> SEQ ID NO 23
<211> LENGTH: 23
<212> TYPE: DNA
<213> ORGANISM: feline

<400> SEQUENCE: 23
actcactata gggctcgagc ggc                                           23

<210> SEQ ID NO 24
<211> LENGTH: 23
<212> TYPE: DNA
<213> ORGANISM: feline

<400> SEQUENCE: 24
gaaatccgag tgactgtgct gag                                           23

<210> SEQ ID NO 25
<211> LENGTH: 24
<212> TYPE: DNA
<213> ORGANISM: feline

<400> SEQUENCE: 25
aacctgaaca ctgctcccat aaag                                          24

<210> SEQ ID NO 26
<211> LENGTH: 25
<212> TYPE: DNA
<213> ORGANISM: feline

<400> SEQUENCE: 26
gcctcagctc ttagaaattg gacag                                    25

<210> SEQ ID NO 27
<211> LENGTH: 21
<212> TYPE: DNA
<213> ORGANISM: feline

<400> SEQUENCE: 27
tagtattttg gcaggaccag g                                        21

<210> SEQ ID NO 28
<211> LENGTH: 23
<212> TYPE: DNA
<213> ORGANISM: feline

<400> SEQUENCE: 28
ctgtgacatt atcttgagat ttc                                      23

<210> SEQ ID NO 29
<211> LENGTH: 20
<212> TYPE: DNA
<213> ORGANISM: feline

<400> SEQUENCE: 29
grcwgcacwa tgggactgag                                          20

<210> SEQ ID NO 30
<211> LENGTH: 23
<212> TYPE: DNA
<213> ORGANISM: feline

<400> SEQUENCE: 30
ctgtgacatt atcttgagat ttc                                      23

<210> SEQ ID NO 31
<211> LENGTH: 27
<212> TYPE: DNA
<213> ORGANISM: feline

<400> SEQUENCE: 31
ccatcctaat acgactcact atagggc                                  27

<210> SEQ ID NO 32
<211> LENGTH: 28
<212> TYPE: DNA
<213> ORGANISM: feline

<400> SEQUENCE: 32
tgggtaacct tgtatagatg agcaggtc                                 28

<210> SEQ ID NO 33
<211> LENGTH: 23
<212> TYPE: DNA
<213> ORGANISM: feline

<400> SEQUENCE: 33
actcactata gggctcgagc ggc                                      23

<210> SEQ ID NO 34
<211> LENGTH: 25
<212> TYPE: DNA
<213> ORGANISM: feline

<400> SEQUENCE: 34
caggttgact gaagttagca agcac                                         25

<210> SEQ ID NO 35
<211> LENGTH: 27
<212> TYPE: DNA
<213> ORGANISM: feline

<400> SEQUENCE: 35
ccatcctaat acgactcact atagggc                                       27

<210> SEQ ID NO 36
<211> LENGTH: 25
<212> TYPE: DNA
<213> ORGANISM: feline

<400> SEQUENCE: 36
ggacaagggc acatatcact gtttc                                         25

<210> SEQ ID NO 37
<211> LENGTH: 23
<212> TYPE: DNA
<213> ORGANISM: feline

<400> SEQUENCE: 37
actcactata gggctcgagc ggc                                           23

<210> SEQ ID NO 38
<211> LENGTH: 25
<212> TYPE: DNA
<213> ORGANISM: feline

<400> SEQUENCE: 38
cagtgcttgc taacttcagt caacc                                         25

<210> SEQ ID NO 39
<211> LENGTH: 23
<212> TYPE: DNA
<213> ORGANISM: feline

<400> SEQUENCE: 39
cgggaatgtc actgagctta tag                                           23

<210> SEQ ID NO 40
<211> LENGTH: 23
<212> TYPE: DNA
<213> ORGANISM: feline

<400> SEQUENCE: 40 gatcttttc aggttagcag ggg                                            23

<210> SEQ ID NO 41
<211> LENGTH: 20
<212> TYPE: DNA
<213> ORGANISM: feline

<400> SEQUENCE: 41
atgggtcacg cagcaaagtg                                               20

<210> SEQ ID NO 42
<211> LENGTH: 20
<212> TYPE: DNA
<213> ORGANISM: feline

<400> SEQUENCE: 42

```
ctatgtagac aggtgagatc                                               20
```

```
<210> SEQ ID NO 43
<211> LENGTH: 17
<212> TYPE: DNA
<213> ORGANISM: feline

<400> SEQUENCE: 43
caggaaacag ctatgac                                                  17

<210> SEQ ID NO 44
<211> LENGTH: 18
<212> TYPE: DNA
<213> ORGANISM: feline

<400> SEQUENCE: 44
aatacgactc actatagg                                                 18

<210> SEQ ID NO 45
<211> LENGTH: 21
<212> TYPE: DNA
<213> ORGANISM: feline

<400> SEQUENCE: 45
aacaccattt catcatcctt t                                             21

<210> SEQ ID NO 46
<211> LENGTH: 23
<212> TYPE: DNA
<213> ORGANISM: feline

<400> SEQUENCE: 46
atacaagtgt atttgccatt gtc                                           23

<210> SEQ ID NO 47
<211> LENGTH: 20
<212> TYPE: DNA
<213> ORGANISM: feline

<400> SEQUENCE: 47
agctctgacc aataacatca                                               20

<210> SEQ ID NO 48
<211> LENGTH: 22
<212> TYPE: DNA
<213> ORGANISM: feline

<400> SEQUENCE: 48
attagaaatc cagttcactg ct                                            22

<210> SEQ ID NO 49
<211> LENGTH: 21
<212> TYPE: DNA
<213> ORGANISM: feline

<400> SEQUENCE: 49
tcatgtctgg caaagtacaa g                                             21

<210> SEQ ID NO 50
<211> LENGTH: 18
<212> TYPE: DNA
<213> ORGANISM: feline

<400> SEQUENCE: 50
```
attcactgac gtcaccga                                                    18

<210> SEQ ID NO 51
<211> LENGTH: 16
<212> TYPE: DNA
<213> ORGANISM: feline

<400> SEQUENCE: 51
aaggctgtgg ctctga                                                      16

<210> SEQ ID NO 52
<211> LENGTH: 29
<212> TYPE: DNA
<213> ORGANISM: feline

<400> SEQUENCE: 52
tcgagaattc gggtcacgca gcaaagtgg                                        29

<210> SEQ ID NO 53
<211> LENGTH: 32
<212> TYPE: DNA
<213> ORGANISM: feline

<400> SEQUENCE: 53
gctaggatcc aatctatgta gacaggtgag at                                    32

<210> SEQ ID NO 54
<211> LENGTH: 32
<212> TYPE: DNA
<213> ORGANISM: feline

<400> SEQUENCE: 54
gatgaattcc atgatcctca ggctgggctt ct                                    32

<210> SEQ ID NO 55
<211> LENGTH: 29
<212> TYPE: DNA
<213> ORGANISM: feline

<400> SEQUENCE: 55
gatcagatct caggaacggt atgccgcaa                                        29

<210> SEQ ID NO 56
<211> LENGTH: 22
<212> TYPE: DNA
<213> ORGANISM: feline
<220> FEATURE:
<221> NAME/KEY: misc_feature
<223> OTHER INFORMATION: Synthetic primer

<400> SEQUENCE: 56
gggccgagta yaagaaccgg ac                                               22

<210> SEQ ID NO 57
<211> LENGTH: 24
<212> TYPE: DNA
<213> ORGANISM: feline
<220> FEATURE:
<221> NAME/KEY: misc_feature
<223> OTHER INFORMATION: Synthetic primer

<400> SEQUENCE: 57
cagwttcagg atcytgggaa aytg                                             24

<210> SEQ ID NO 58

```
<211> LENGTH: 20
<212> TYPE: DNA
<213> ORGANISM: feline
<220> FEATURE:
<221> NAME/KEY: misc_feature
<223> OTHER INFORMATION: Synthetic primer

<400> SEQUENCE: 58
ttatactagg gacagggaag                                              20

<210> SEQ ID NO 59
<211> LENGTH: 20
<212> TYPE: DNA
<213> ORGANISM: feline
<220> FEATURE:
<221> NAME/KEY: misc_feature
<223> OTHER INFORMATION: Synthetic primer

<400> SEQUENCE: 59
aagctttgga aaacctccag                                              20

<210> SEQ ID NO 60
<211> LENGTH: 21
<212> TYPE: DNA
<213> ORGANISM: feline
<220> FEATURE:
<221> NAME/KEY: misc_feature
<223> OTHER INFORMATION: Synthetic primer

<400> SEQUENCE: 60
ttgttatcgg tgacgtcagt g                                            21

<210> SEQ ID NO 61
<211> LENGTH: 22
<212> TYPE: DNA
<213> ORGANISM: feline
<220> FEATURE:
<221> NAME/KEY: misc_feature
<223> OTHER INFORMATION: Synthetic primer

<400> SEQUENCE: 61
caataacatc accgaagtca gg                                           22

<210> SEQ ID NO 62
<211> LENGTH: 22
<212> TYPE: DNA
<213> ORGANISM: feline
<220> FEATURE:
<221> NAME/KEY: misc_feature
<223> OTHER INFORMATION: Synthetic primer

<400> SEQUENCE: 62
gtcatgtctg gcaaagtacc ag                                           22

<210> SEQ ID NO 63
<211> LENGTH: 22
<212> TYPE: DNA
<213> ORGANISM: feline
<220> FEATURE:
<221> NAME/KEY: misc_feature
<223> OTHER INFORMATION: Synthetic primer

<400> SEQUENCE: 63
cactgacgtc accgataacc ac                                           22

<210> SEQ ID NO 64
<211> LENGTH: 22
<212> TYPE: DNA
```

```
<213> ORGANISM: feline
<220> FEATURE:
<221> NAME/KEY: misc_feature
<223> OTHER INFORMATION: Synthetic primer

<400> SEQUENCE: 64
ctgacttcgg tgatgttatt gg                                                22

<210> SEQ ID NO 65
<211> LENGTH: 21
<212> TYPE: DNA
<213> ORGANISM: feline
<220> FEATURE:
<221> NAME/KEY: misc_feature
<223> OTHER INFORMATION: Synthetic primer

<400> SEQUENCE: 65
gccatcaaca caacagtttc c                                                 21

<210> SEQ ID NO 66
<211> LENGTH: 22
<212> TYPE: DNA
<213> ORGANISM: feline
<220> FEATURE:
<221> NAME/KEY: misc_feature
<223> OTHER INFORMATION: Synthetic primer

<400> SEQUENCE: 66
tatgacaaac aaccatagct tc                                                22

<210> SEQ ID NO 67
<211> LENGTH: 20
<212> TYPE: DNA
<213> ORGANISM: feline
<220> FEATURE:
<221> NAME/KEY: misc_feature
<223> OTHER INFORMATION: Synthetic primer

<400> SEQUENCE: 67
graagawtgc ctcatgakcc                                                   20

<210> SEQ ID NO 68
<211> LENGTH: 17
<212> TYPE: DNA
<213> ORGANISM: feline
<220> FEATURE:
<221> NAME/KEY: misc_feature
<223> OTHER INFORMATION: Synthetic primer

<400> SEQUENCE: 68
cayratccaa cataggg                                                      17

<210> SEQ ID NO 69
<211> LENGTH: 21
<212> TYPE: DNA
<213> ORGANISM: feline
<220> FEATURE:
<221> NAME/KEY: misc_feature
<223> OTHER INFORMATION: Synthetic primer

<400> SEQUENCE: 69
atgggtcacg cagcaaagtg g                                                 21

<210> SEQ ID NO 70
<211> LENGTH: 21
<212> TYPE: DNA
<213> ORGANISM: feline
<220> FEATURE:
```

<221> NAME/KEY: misc_feature
<223> OTHER INFORMATION: Synthetic primer

<400> SEQUENCE: 70
caaccttagc tgcaagtaca c                                          21

<210> SEQ ID NO 71
<211> LENGTH: 20
<212> TYPE: DNA
<213> ORGANISM: feline
<220> FEATURE:
<221> NAME/KEY: misc_feature
<223> OTHER INFORMATION: Synthetic primer

<400> SEQUENCE: 71
ggcttctgga tagggatagg                                            20

<210> SEQ ID NO 72
<211> LENGTH: 22
<212> TYPE: DNA
<213> ORGANISM: feline
<220> FEATURE:
<221> NAME/KEY: misc_feature
<223> OTHER INFORMATION: Synthetic primer

<400> SEQUENCE: 72
cggaggtaga attgcactgt cc                                         22

<210> SEQ ID NO 73
<211> LENGTH: 21
<212> TYPE: DNA
<213> ORGANISM: feline
<220> FEATURE:
<221> NAME/KEY: misc_feature
<223> OTHER INFORMATION: Synthetic primer

<400> SEQUENCE: 73
attttgcaga agtaaatatc c                                          21

<210> SEQ ID NO 74
<211> LENGTH: 20
<212> TYPE: DNA
<213> ORGANISM: feline
<220> FEATURE:
<221> NAME/KEY: misc_feature
<223> OTHER INFORMATION: Synthetic primer

<400> SEQUENCE: 74
catgtctggc aaagtacaag                                            20

<210> SEQ ID NO 75
<211> LENGTH: 20
<212> TYPE: DNA
<213> ORGANISM: feline
<220> FEATURE:
<221> NAME/KEY: misc_feature
<223> OTHER INFORMATION: Synthetic primer

<400> SEQUENCE: 75
ttatactagg gacagggaag                                            20

<210> SEQ ID NO 76
<211> LENGTH: 22
<212> TYPE: DNA
<213> ORGANISM: feline
<220> FEATURE:
<221> NAME/KEY: misc_feature
<223> OTHER INFORMATION: Synthetic primer

```
<400> SEQUENCE: 76
ccttcattga cctcaactac at                                              22

<210> SEQ ID NO 77
<211> LENGTH: 21
<212> TYPE: DNA
<213> ORGANISM: feline
<220> FEATURE:
<221> NAME/KEY: misc_feature
<223> OTHER INFORMATION: Synthetic primer

<400> SEQUENCE: 77
ccaaagttgt catggatgac c                                               21

<210> SEQ ID NO 78
<211> LENGTH: 22
<212> TYPE: DNA
<213> ORGANISM: feline
<220> FEATURE:
<221> NAME/KEY: misc_feature
<223> OTHER INFORMATION: Synthetic primer

<400> SEQUENCE: 78
caaccccaaa ctctccagga tg                                              22

<210> SEQ ID NO 79
<211> LENGTH: 24
<212> TYPE: DNA
<213> ORGANISM: feline
<220> FEATURE:
<221> NAME/KEY: misc_feature
<223> OTHER INFORMATION: Synthetic primer

<400> SEQUENCE: 79
ggtcagcgtt gagaagatgc tttg                                            24

<210> SEQ ID NO 80
<211> LENGTH: 21
<212> TYPE: DNA
<213> ORGANISM: feline
<220> FEATURE:
<221> NAME/KEY: misc_feature
<223> OTHER INFORMATION: Synthetic primer

<400> SEQUENCE: 80
tattaatggg tctcacctac c                                               21

<210> SEQ ID NO 81
<211> LENGTH: 21
<212> TYPE: DNA
<213> ORGANISM: feline
<220> FEATURE:
<221> NAME/KEY: misc_feature
<223> OTHER INFORMATION: Synthetic primer

<400> SEQUENCE: 81
ttggcttcat tcacagaaca g                                               21

<210> SEQ ID NO 82
<211> LENGTH: 24
<212> TYPE: DNA
<213> ORGANISM: feline
<220> FEATURE:
<221> NAME/KEY: misc_feature
<223> OTHER INFORMATION: Synthetic primer

<400> SEQUENCE: 82
```

```
gggtcgcttt tcgtagacat tttg                                          24

<210> SEQ ID NO 83
<211> LENGTH: 22
<212> TYPE: DNA
<213> ORGANISM: feline
<220> FEATURE:
<221> NAME/KEY: misc_feature
<223> OTHER INFORMATION: Synthetic primer

<400> SEQUENCE: 83
caggcaggac aaccattatt tc                                            22
```